US011964104B2

(12) United States Patent
Chilcott et al.

(10) Patent No.: US 11,964,104 B2
(45) Date of Patent: Apr. 23, 2024

(54) BREATH SAMPLING INTERFACE

(71) Applicant: Fisher & Paykel Healthcare Limited, Auckland (NZ)

(72) Inventors: Kate Jayne Chilcott, Auckland (NZ); Alicia Jerram Hunter Evans, Auckland (NZ); Edward John Evans, Auckland (NZ); Samantha Dale Oldfield, Auckland (NZ); Nathan James Roa, Auckland (NZ); Craig Karl White, Auckland (NZ)

(73) Assignee: FISHER & PAYKEL HEALTHCARE LIMITED, Auckland (NZ)

( * ) Notice: Subject to any disclaimer, the term of this patent is extended or adjusted under 35 U.S.C. 154(b) by 1080 days.

(21) Appl. No.: 16/341,767

(22) PCT Filed: Oct. 16, 2017

(86) PCT No.: PCT/NZ2017/050134
§ 371 (c)(1),
(2) Date: Apr. 12, 2019

(87) PCT Pub. No.: WO2018/070885
PCT Pub. Date: Apr. 19, 2018

(65) Prior Publication Data
US 2021/0370006 A1 Dec. 2, 2021

Related U.S. Application Data

(60) Provisional application No. 62/492,783, filed on May 1, 2017, provisional application No. 62/408,480, filed on Oct. 14, 2016.

(51) Int. Cl.
*A61M 16/06* (2006.01)
*A61M 16/08* (2006.01)

(52) U.S. Cl.
CPC ...... *A61M 16/085* (2014.02); *A61M 16/0666* (2013.01); *A61M 2210/0618* (2013.01); *A61M 2240/00* (2013.01)

(58) Field of Classification Search
CPC ............... A61J 15/0003; A61J 15/0023; A61J 15/0073; A61M 15/08; A61M 16/0057;
(Continued)

(56) References Cited

U.S. PATENT DOCUMENTS 4,278,082 A * 7/1981 Blackmer ......... A61M 16/0672
128/207.18
5,046,491 A 9/1991 Derrick
(Continued)

FOREIGN PATENT DOCUMENTS

EP 1845841 12/2004
EP 2005789936 7/2007
(Continued)

OTHER PUBLICATIONS

International Search Report, Application No. PCT/NZ2017/050134, dated Feb. 15, 2018, in 8 pages.

*Primary Examiner* — Annette Dixon
(74) *Attorney, Agent, or Firm* — Knobbe Martens Olson & Bear LLP

(57) ABSTRACT

There is provided a a respiratory gas delivery and sampling system, a gas sampling system, a gas sampling interface and a gas sampling tip that may be used to sample exhaled and/or expired gases from a patient, particularly from a patient who is apnoeic and/or who is receiving high flow respiratory therapy. The gas sampling system comprises a respiratory gas monitor in fluid communication with the gas sampling interface, which comprises the gas sampling tip of the invention. The gas sampling interface comprises a gas sampling conduit and the gas sampling tip is located at a free end of the conduit. The gas sampling interface may be (Continued)

configured to allow the gas sampling tip to be selectively positioned at or in the mouth or a nare of the patient's nose.

31 Claims, 44 Drawing Sheets

(58) Field of Classification Search
CPC .......... A61M 16/0063; A61M 16/024; A61M 16/04; A61M 16/0415; A61M 16/0418; A61M 16/0434; A61M 16/0479; A61M 16/0486; A61M 16/0488; A61M 16/0493; A61M 16/0666; A61M 16/0672; A61M 16/0677; A61M 16/0833; A61M 16/0841; A61M 16/085; A61M 16/101; A61M 16/12; A61M 16/204; A61M 2016/0021; A61M 2016/0027; A61M 2016/0039; A61M 2016/0661; A61M 2202/0007; A61M 2202/0208; A61M 2202/03; A61M 2205/32; A61M 2205/3393; A61M 2205/42; A61M 2205/502; A61M 2205/8206; A61M 2209/084; A61M 2210/0625; A61M 2230/432; A61M 2230/435; Y10T 24/3444
See application file for complete search history.

(56) References Cited

U.S. PATENT DOCUMENTS

| | | | |
|---|---|---|---|
| 5,335,656 | A | 8/1994 | Bowe et al. |
| 6,319,244 | B2 | 11/2001 | Suresh et al. |
| 6,976,979 | B2 | 12/2005 | Lawrence et al. |
| 7,063,084 | B2 | 6/2006 | McDonald |
| 7,337,780 | B2 | 3/2008 | Curti et al. |
| 7,735,490 | B2 | 6/2010 | Rinaldi |
| 7,832,400 | B2 | 11/2010 | Curti et al. |
| 7,997,271 | B2 | 8/2011 | Hickle et al. |
| 8,074,652 | B2 | 12/2011 | Curti et al. |
| 8,333,200 | B2 | 12/2012 | Tero |
| 8,616,203 | B2 | 12/2013 | Jaffe et al. |
| 8,740,808 | B2 | 6/2014 | Curti et al. |
| 9,055,888 | B2 | 6/2015 | Levitsky et al. |
| 9,198,586 | B2 | 12/2015 | Melker |
| 9,440,039 | B2 | 9/2016 | Payton et al. |
| 9,604,024 | B2 | 3/2017 | Curti |
| 9,636,043 | B2 | 5/2017 | Levitsky et al. |
| 9,782,559 | B2 | 10/2017 | Farnan et al. |
| 9,808,182 | B2 | 11/2017 | Johnson et al. |
| 9,827,392 | B2 | 11/2017 | Lei |
| 9,867,554 | B2 | 1/2018 | Derrick |
| 9,925,348 | B2 | 3/2018 | Payton et al. |
| 9,993,607 | B2 | 6/2018 | Weaver et al. |
| 10,034,993 | B2 | 7/2018 | Simon |
| 10,137,287 | B2 | 11/2018 | Sansone et al. |
| 2001/0031929 | A1 | 10/2001 | O'Toole |
| 2002/0053346 | A1* | 5/2002 | Curti ............... A61M 16/085 128/207.18 |
| 2002/0112730 | A1* | 8/2002 | Dutkiewicz ....... A61M 16/0666 128/207.18 |
| 2006/0169281 | A1* | 8/2006 | Aylsworth ........ A61M 16/0666 128/204.26 |
| 2009/0125002 | A1* | 5/2009 | Totz ................ A61M 16/04 128/207.15 |
| 2009/0133699 | A1 | 5/2009 | Nalagatla et al. |
| 2009/0283097 | A1 | 11/2009 | Niklewski |
| 2012/0060845 | A1 | 3/2012 | McKinnon et al. |
| 2012/0123392 | A1 | 5/2012 | McKinnon et al. |
| 2012/0271187 | A1 | 10/2012 | Mcneill |
| 2013/0092165 | A1* | 4/2013 | Wondka ............ A61M 16/204 128/204.25 |
| 2014/0018691 | A1 | 1/2014 | Mcneill |
| 2015/0217075 | A1 | 8/2015 | Nair |
| 2016/0015296 | A1 | 1/2016 | Garaycochea |
| 2016/0058973 | A1 | 3/2016 | Farnan et al. |
| 2016/0220777 | A1 | 8/2016 | Weaver et al. |
| 2016/0270692 | A1 | 9/2016 | Johnson et al. |
| 2016/0345863 | A1 | 12/2016 | Johnson et al. |
| 2016/0345864 | A1 | 12/2016 | Johnson et al. |
| 2016/0345894 | A1 | 12/2016 | Johnson et al. |
| 2017/0014048 | A1 | 1/2017 | Wilke |
| 2017/0095630 | A1 | 4/2017 | Yeatts |
| 2017/0258614 | A1 | 9/2017 | Griffin |
| 2017/0360337 | A1 | 12/2017 | Sherwood et al. |
| 2018/0015253 | A1 | 1/2018 | Farnan et al. |
| 2018/0020949 | A1 | 1/2018 | Johnson et al. |
| 2018/0043123 | A1 | 2/2018 | Lei |
| 2018/0221617 | A1 | 8/2018 | Chaudhry |
| 2018/0236199 | A1 | 8/2018 | Lussier et al. |

FOREIGN PATENT DOCUMENTS

| | | |
|---|---|---|
| EP | 2204206 | 3/2016 |
| GB | 2509922 | 7/2014 |
| WO | WO 2012/037277 | 3/2012 |
| WO | WO 2017/101184 | 12/2015 |
| WO | WO 2016/035035 | 3/2016 |
| WO | WO 2018/085864 | 10/2017 |

* cited by examiner

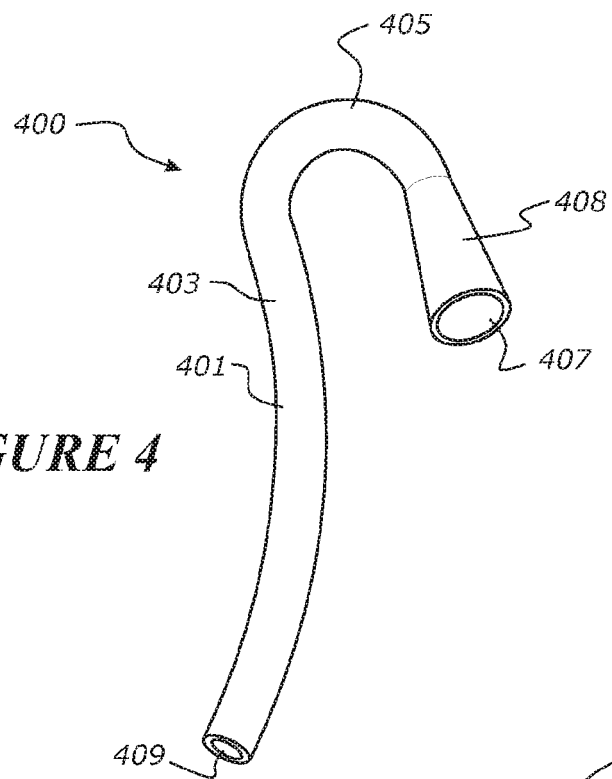
*FIGURE 4*
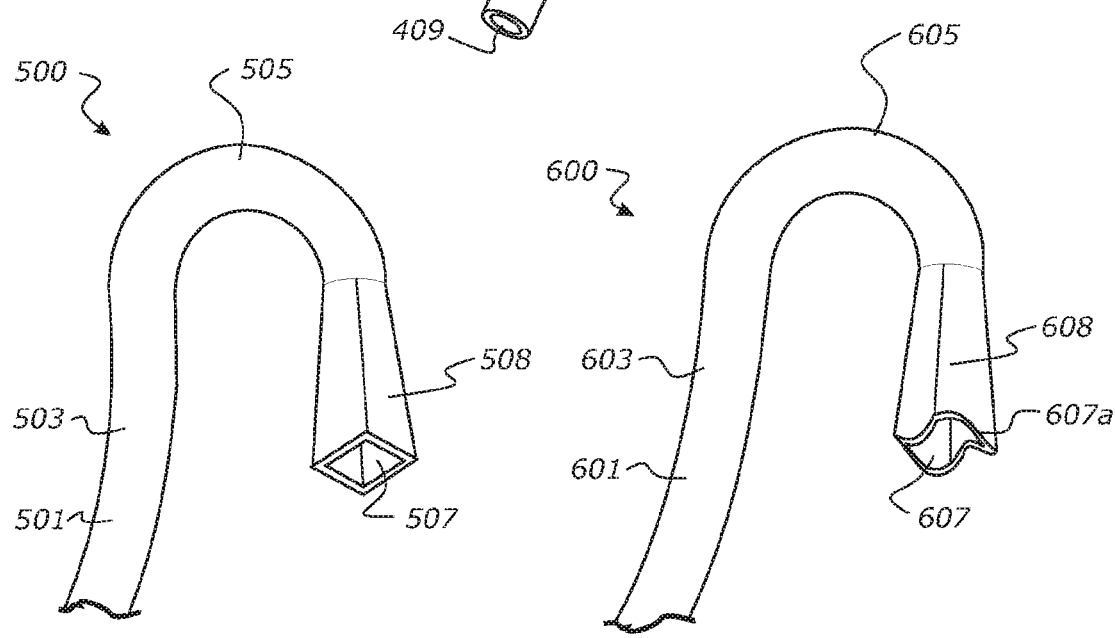
*FIGURE 5*  *FIGURE 6*

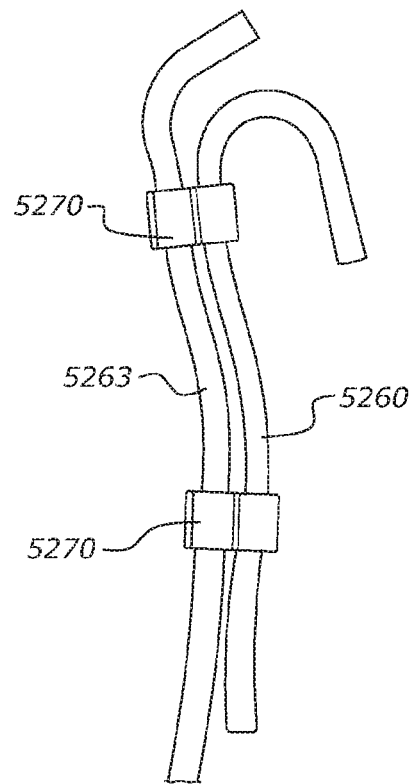
FIGURE 52
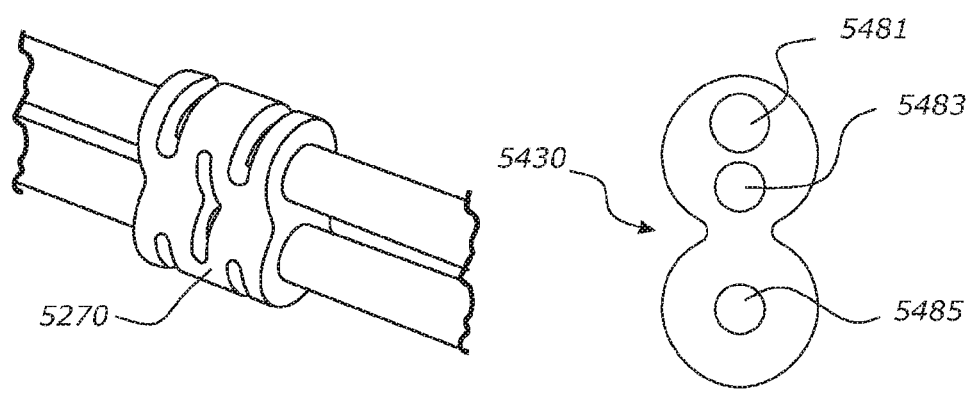
FIGURE 53
FIGURE 54

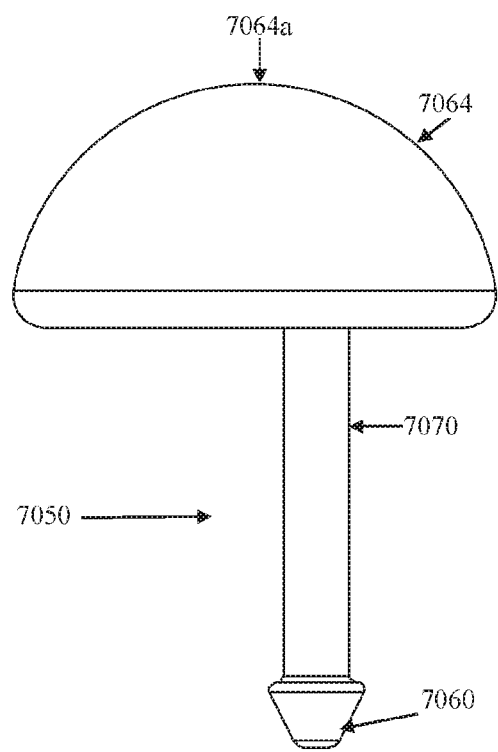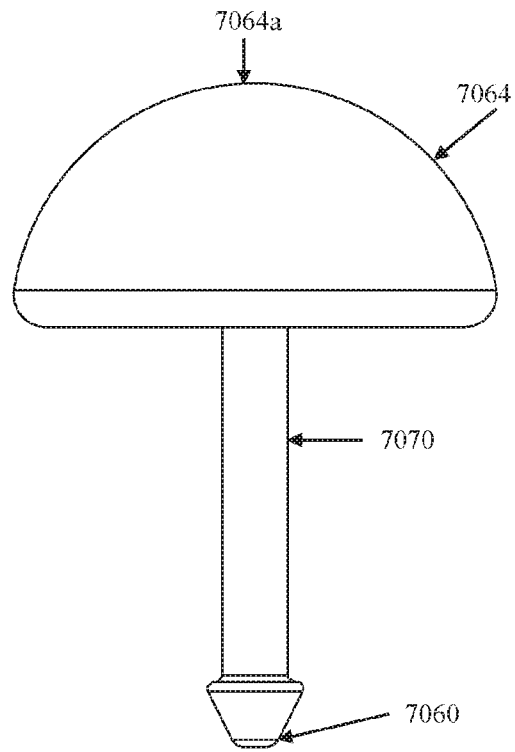
*FIGURE 68A*  *FIGURE 68B*

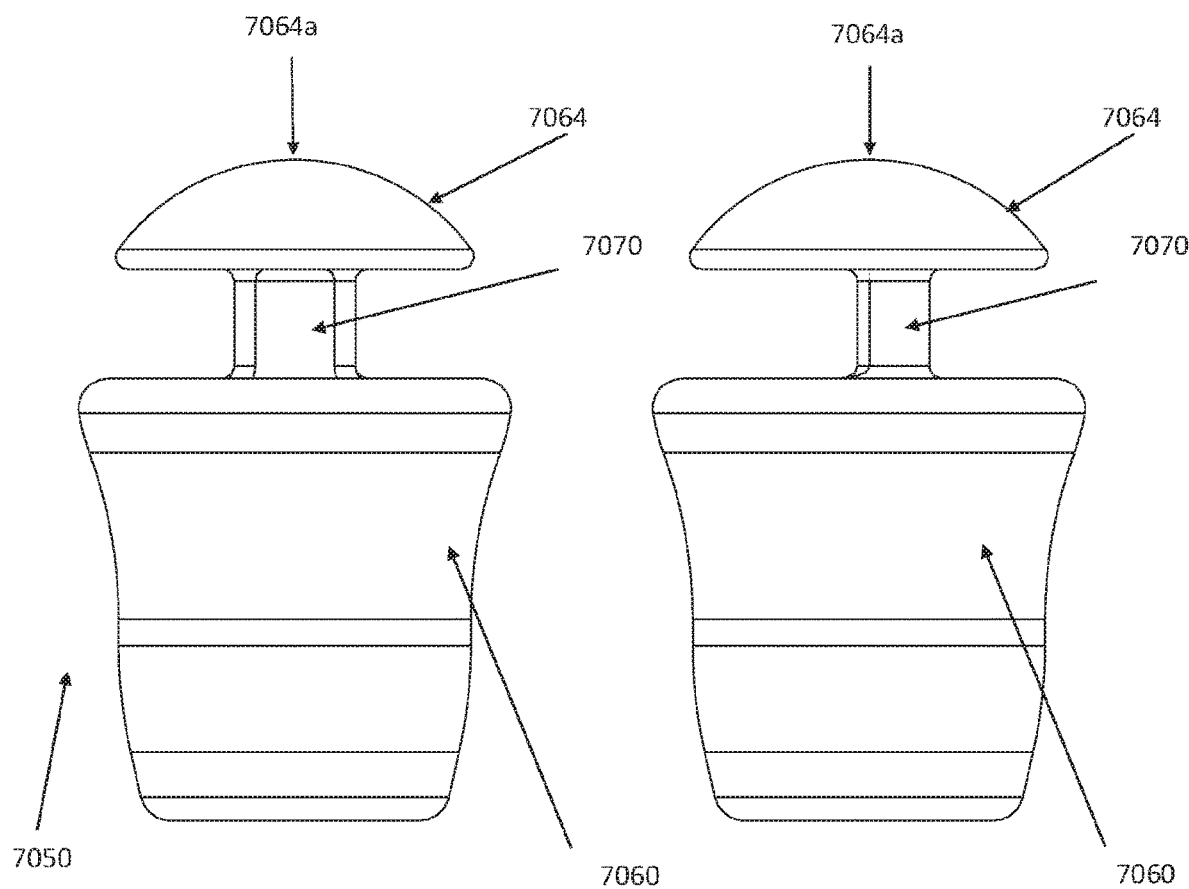
*FIGURE 69A*  *FIGURE 69B*

BREATH SAMPLING INTERFACE

TECHNICAL FIELD

The present disclosure generally relates to respiratory gas therapy. More particularly, the present disclosure relates to an interface for capturing exhaled and/or expired gases, such as $CO_2$, in proximity of a patient's nose or mouth while the patient is being supplied with respiratory gas by a breathing apparatus. In use, the interface comprises or is typically fluidly connected to a gas sampling conduit which is fluidly connected to a respiratory gas monitor. The interface may be particularly useful when measuring exhaled and/or expired gases from a patient receiving high flow respiratory gas.

DESCRIPTION OF THE RELATED ART

In medical environments, it is common practice to monitor the concentration of gases exhaled and/or expired by a patient using a gas sampling system comprising a respiratory gas monitor that connects to a gas sampling interface comprising a gas sampling conduit to transfer exhaled and/or expired gas from a patient to the respiratory gas monitor. Respiratory gas monitors are well known in the art, and range from more comprehensive monitors, which are capable of monitoring several different types of gases (such as Nitrogen, $O_2$, $CO_2$, anaesthetic gases, etc.), to more specialized monitors which may monitor only a single type of gas. One example of a more specialized respiratory gas monitor is a capnogram/capnograph, which monitors $CO_2$ by drawing exhaled and/or expired gas from a patient into a gas sampling interface connected to the capnogram/capnograph. An anaesthesia machine may also provide a respiratory gas monitor. The respiratory gas monitor may be completely or partially incorporated into an anaesthesia machine or may be independent thereof. The respiratory gas monitor may provide a small amount of suction in order to draw gases into the sampling conduit.

The respiratory gas monitor receives exhaled and/or expired gas via the sampling conduit of the gas sampling interface. For example, an inlet of the sampling conduit may be positioned near the patient's nose or mouth, such that the sampling conduit captures passing exhaled and/or expired gases, which then enter the conduit through the inlet. In some instances, the inlet may fluidly connect to or form part of a breathing apparatus, such as a mask or cannula. In some instances, the sampling conduit is independent of a patient interface and the terminal end of the sampling conduit may be held or taped in place on the patient's face.

Although gas sampling is commonly used with anaesthetised patient's, known gas sampling interfaces, gas sampling conduits, and processes for gas sampling are fraught with difficulties.

For example, the process of taping the sampling conduit to the patient's face requires some preparation time and skill on the part of the anaesthetist, anaesthetic technician, nurse, or other medical practitioner. Correct placement of the sampling conduit is also required in order to place the conduit/tube such that it reliably captures exhaled and/or expired gases.

The gas sampling interface or sampling conduit can also be dislodged if the patient moves their head or if instruments are used near or have to manoeuvre around the sampling interface or conduit.

Some gas sampling interfaces can also get in the way of instruments or equipment, such as bite blocks, endoscopes or laryngoscopes. Further, if a portion of the sampling conduit is positioned inside the patient's mouth, the end of the sampling conduit can become blocked by saliva or blood or can suction onto the inside of the patient's cheek or onto the patient's tongue.

Current methods do not allow for simple repositioning of the sampling interface when required. For example, reliable $CO_2$ sampling may be difficult when it is unclear in advance of a procedure whether a patient will breathe predominantly from the nose or mouth. For example, if a sampling conduit is taped in place at the nose of a patient and it subsequently becomes apparent that the patient is breathing predominantly from the mouth, it will be necessary to remove and then tape the conduit in position at the patient's mouth. Repositioning of the sampling conduit in this manner requires the sampling conduit attachment procedure to be repeated, which is time consuming.

Therefore, it is desirable to provide a sampling interface that facilitates engagement of a sampling conduit with a patient such that engagement is rapid, and the placement of the conduit reliably captures $CO_2$ in exhaled and/or expired breath.

Gas sampling is particularly difficult when a patient is apnoeic because the amount of gas exiting or expired out of the lungs of an apnoeic patient is very low. Expired $CO_2$ (which may simply diffuse from an apnoeic patient's airways) cannot accurately be detected in the nose or mouth because there is no patient ventilation to effectively expel the gas that far from the lungs and any gas that exits at the nose or mouth is significantly diluted. It may be possible to sample exiting gas anywhere in the trachea (i.e. from the back of the throat to the carina) where the exiting gas is less diluted. However, sampling at the back of the throat creates difficulties during procedures that require access to the patient's airways, such as during oral procedures where the sampling interface may interfere with a surgeon's tools. It is also difficult and sometimes impossible to intubate a patient undergoing an oral surgical procedure. For this reason, high flow respiratory therapy may sometimes be used to provide breathing gas to patients undergoing oral surgery or surgery at a site that is accessed via the mouth, although high flow therapy may be used in many other medical procedures too. High flow therapy refers to the supply of breathing gas to an adult patient at high flow rates (typically between about 15 L/min and about 150 L/min. and preferably between about 30 L/min and about 120 L/min) through a breathing apparatus. However, flow rates that are defined as high flow may vary depending on the patient. For example, in high flow therapy of a neonatal infant, breathing gas is typically supplied at a flow rate of about 2 L/min/kg. Low flow cannulas typically cannot provide breathing gas at flow rates above 15 L/min.

The nature of high flow therapy creates significant dilution of the expired gas from the patient, making it difficult to accurately measure $CO_2$ and other expired gases.

More particularly, anatomic dead space is the total volume of the conducting airways of a patient, from the nose and mouth through to the terminal bronchioles. During normal expiration, this dead space is filled uniformly with $CO_2$-rich gas from the lungs. At the transition point from expiration to inspiration, the $CO_2$-rich gas remaining in the dead space is rebreathed back into the lungs as part of inspiration. When using $CO_2$ monitoring in this state (i.e. normal unassisted breathing by the patient), the $CO_2$-rich gas that fills the dead space during expiration is what is measured by a gas sampling system. Due to the uniform gas distribution. $CO_2$ sampling interfaces can be made to sample nasally or orally, to take a sample measurement that is roughly equivalent to the $CO_2$ levels found in the lungs, allowing inferences to be made about the measurement. However, monitoring $CO_2$ or other expired and/or exhaled gases whilst also supplying high flow therapy (supplying breathing gas to a patient at high flow rates though a breathing apparatus) is difficult. This is due to the flushing mechanism provided by high flow therapy that alters the flow pattern within the anatomical dead space, causing a non-uniform distribution of expired gas. The $CO_2$-rich gas flow from the lungs is displaced or 'flushed' from the dead space by fresh gas from the breathing apparatus and also (to a much lesser extent) by cardiogenic pulses. As a consequence, high flow therapy creates a turbulent flow pattern of gas movement, with recirculation features, resulting in less $CO_2$ being rebreathed. When the non-uniform gas distribution is sampled from the nose and/or mouth, an invalid quantitative measurement is made by a standard respiratory gas monitor in a gas sampling system. Compensation algorithms may be implemented to help account for the incorrect measurement and qualitative interpretation of the gas sample is still possible provided that sufficient $CO_2$ is sampled.

U.S. Pat. No. 7,337,780 discloses a combined gas delivery and gas sampling interface. The interface comprises a nasal cannula with a mouth trunk, where the gas is delivered through one of the nasal prongs of a cannula and sampled through both the other prong and the mouth trunk. The mouth trunk includes a wire spine that allows the mouth trunk to be bent to a desired position to sample exhaled gases from a patient's mouth. However, the cannula is not suitable for delivering high flow therapy, for delivery therapy through both nares of a patient's nose, or for allowing selective gas sampling from the nose or the mouth.

It would therefore be useful to provide a gas sampling interface that can be used to sample expired and/or exhaled gases selectively from the mouth or nose, even when gas is supplied to an apnoeic patient under high flow therapy.

Following the use of a sampling conduit, disposal and replacement or sanitisation of the sampling conduit is typically required prior to the next patient in order to prevent contamination.

Therefore, it is also desirable to facilitate case of disposal or sanitisation of the sampling conduit or associated components.

SUMMARY

In accordance with a first aspect, there is provided a gas sampling interface comprising: a conduit having a body with a hook portion for engaging with part of a patient's face, the body defining a lumen having an inlet for receiving gases exhaled and/or expired by a patient and an outlet for delivering the exhaled and/or expired gases to a gas measurement device.

In one form, the hook portion is adapted to engage a patient's face at or near an orifice of the patient's face. Preferably, the hook portion is adapted to engage with a patient's mouth or part of the patient's mouth. The hook portion may be adapted to engage with the patient's nose or part of the patient's nose. Preferably, the shape of the hook portion is adjustable. In one form, the hook portion comprises a generally convex portion. Preferably, the body further comprises a generally concave portion that leads into the generally convex hook portion that leads into another generally concave portion.

Preferably, the interface is disposable.

In one form, the conduit is a dual conduit lumen. In one form, the gas sampling interface further comprises a length of malleable wire occupying one of the lumens.

In another form, the conduit is a single lumen conduit.

Preferably, the conduit is or comprises a polymeric material.

The conduit may be connectable to a sampling tube via a luer.

Preferably, the inlet has a mouth that has a cross-sectional area that is greater than a cross-sectional area of the conduit or lumen.

In one form, the conduit has a tip with an alternating or varying depth, when viewed in cross-section.

Optionally, the conduit comprises multiple gas receiving apertures or openings about the periphery of the tip and/or along a distance of the conduit from the tip. Preferably, the conduit comprises one or more non-circular openings about the periphery of the tip and/or along a distance of the conduit from the tip.

Preferably, the tip of the interface comprises a filter or tip structure adapted to substantially inhibit the ingress of liquid. The tip structure may comprise an absorbent porous sponge or foam which at least partially surrounds the tip of the interface.

Preferably, the tip structure comprises a shield, cage, drum, or spacer that surrounds the tip of the interface. In one form, the shield comprises a substantially cylindrical component. In another form, the shield comprises an elongate component having a generally C-shaped cross-section. In yet another form, the shield comprises an elongate component having a generally square cross-section. Optionally, the shield has one or more openings or cut-outs. For example, the shield may comprise a castellated component. Alternatively, the shield may comprise a sinuous component. In one form, the shield comprises a generally V-shaped component. In another form, the shield comprises a planar component.

In accordance with a second aspect, there is provided a gas sampling interface comprising a hook for engaging with part of a patient's face and an attachment member for securing a gas sampling conduit relative to the hook such that the inlet receives gases exhaled or expired by the patient.

Preferably, the hook is rigid. Alternatively, the hook is flexible. In one form, the position of the gas sampling conduit is adjustable relative to the hook.

Preferably, the attachment member removably attaches to the gas sampling conduit. In one form, the attachment member consists of or comprises a channel. In another form, the attachment member consists of or comprises a clip or a pair of clips. In one form, the attachment member consists of or comprises an elastomeric material. The attachment member may optionally be integral with the hook. Alternatively, the attachment member is a separate component to the hook.

In accordance with a third aspect, there is provided a gas sampling interface comprising: a nasal cannula having a manifold and at least one nasal prong or outlet extending from the manifold to be received in a patient's nare, and an attachment member for securing a gas sampling conduit relative to the nasal cannula such that the inlet receives gases exhaled or expired by the patient.

Preferably, the attachment member removably attaches to the gas sampling conduit. In one form, the attachment member consists of or comprises a clip or a pair of clips. In another form, the attachment member consists of or comprises a band or sleeve. Optionally, the attachment member consists of or comprises an elastomeric material. In one form, the attachment member is integral with the manifold and/or at least one nasal prong or outlet. In another form, the attachment member is a separate component to the manifold and/or at least one nasal prong or outlet. Preferably, the position of the gas sampling conduit is adjustable relative to the attachment member.

In accordance with a fourth aspect, there is provided an assembly comprising a gas sampling conduit and an attachment member for securing the gas sampling conduit to a nasal cannula, wherein the attachment member is attachable to the nasal cannula, the attachment member comprising at least two offset clips attachable to the gas sampling conduit to cause the gas sampling conduit, when attached, to follow a tortuous path.

Preferably, the attachment member removably attaches to the gas sampling conduit. In one form, each clip comprises a tube receiving region within which a portion of the gas sampling conduit may be held.

In one form, the attachment member comprises a sleeve comprising a body and a pair of spaced apart arms projecting from the body, wherein the sleeve further comprises an interior region, located between the arms, and an opening to the interior region, wherein the opening is formed along the length of the sleeve and is defined by side edges of the arms, and wherein the interior region is configured to receive a portion of a breathing apparatus. Optionally, the body of the attachment member comprises a sleeve comprising an interior region and an opening to the interior region, wherein the opening is formed along the length of the sleeve and is defined by side edges of the sleeve, and wherein the interior region is configured to receive a portion of a breathing apparatus. Preferably, the interior region comprises a substantially arcuate inner surface. For example, the sleeve may comprise a substantially C-shaped cross section. In another form, the sleeve comprises a substantially U-shaped cross section. Optionally, the substantially arcuate inner surface is formed from a plurality of substantially planar surfaces connected in series to form a substantially arcuate shape. In this form, the sleeve may comprise a substantially C-shaped cross section. Alternatively, the sleeve may comprise a substantially U-shaped cross section. Preferably, the sleeve is formed from a substantially flexible, resilient material. For example, the sleeve may comprise a polymeric material. Preferably, the interior region of the sleeve is substantially curved and is dimensioned to receive a portion of a gas delivery tube of the nasal cannula, and the width of the opening between the side edges is less than the diameter of the portion of the gas delivery tube to be held by the attachment member. In one form, the arms of the sleeve are biased toward each other. Each clip may form a hook comprising a curved arm extending from the body and terminating in a distal end, wherein the arm may comprise an inner surface that forms a substantially concave receiving region. Preferably, the diameter of the substantially concave receiving region is at least as large as the diameter of the gas sampling lumen. In one form, the distance between a distal end portion of the hook and the body is less than the diameter of the gas sampling conduit.

Preferably, the attachment member is configured to attach to side arms of a cannula, such as a nasal cannula. Optionally, the concave receiving region of the clip is dimensioned or shaped to match the shape of a cannula side arm. In one form, the concave receiving region of the clip includes a plurality of planar surfaces that are shaped to accommodate a cannula side arm.

In accordance with a fifth aspect, there is provided a gas sampling tip to removably connect to an inlet of a gas sampling conduit, wherein the sampling tip comprises a body comprising a substantially hollow interior region configured to be in fluid communication with the inlet of the gas sampling conduit when connected to the gas sampling conduit, and wherein the body also comprises a distal end portion comprising a distal end surface and an outer side surface, wherein the gas sampling tip further comprises at least one gas receiving aperture to receive gases exhaled or expired by a patient, and wherein the gas receiving aperture is in fluid communication with the substantially hollow interior region of the body.

Preferably, at least one gas receiving aperture is formed both in the distal end surface and outer circumferential side surface such that the gas receiving aperture extends from the distal end surface and along the outer side surface. In one form, at least one gas receiving aperture forms an elongate opening in the distal end portion of the gas sampling tip. The distal end of the gas sampling lip may be outwardly curved. For example, the distal end portion of the gas sampling tip may be substantially bulbous.

Preferably, the gas sampling tip comprises three gas receiving apertures evenly spaced around the distal end of the sampling tip. Preferably, the distal end of the gas receiving aperture(s) is/are narrower than an opposing end of the gas receiving aperture(s).

In one form, the gas sampling tip has a substantially cylindrical shape and forms a substantially circumferential outer side surface. Preferably, each portion of the body located between the gas receiving apertures forms a flute, wherein the flutes are substantially evenly spaced around the circumference of the distal end portion of the gas sampling tip.

In accordance with a sixth aspect, there is provided a gas sampling interface comprising: a gas sampling conduit comprising an inlet to receive gases exhaled or expired by a patient, and an outlet to connect to a respiratory gas monitor; and a removable sampling tip located at the inlet of the conduit, wherein the sampling tip comprises a body comprising a substantially hollow interior region configured to be in fluid communication with the inlet of the gas sampling conduit when connected to the gas sampling conduit, and wherein the body also comprises a distal end portion comprising a distal end surface and an outer side surface, wherein the gas sampling tip further comprises at least one gas receiving aperture to receive gases exhaled or expired by a patient, and wherein the gas receiving aperture is in fluid communication with the substantially hollow interior region of the body.

Preferably, at least one gas receiving aperture is formed both in the distal end surface and outer side surface such that the gas receiving aperture extends from the distal end surface and along the side surface. The gas receiving aperture may form an elongate opening in the distal end portion of the gas sampling tip. In one form, the distal end of the gas sampling tip is outwardly curved. For example, the distal end portion of the gas sampling tip may be substantially bulbous.

Preferably, the gas sampling tip comprises three gas receiving apertures evenly spaced around the distal end of the sampling tip. The distal end of the gas receiving aperture (s) may be narrower than an opposing end of the gas receiving aperture(s). In one form, the gas sampling tip has a substantially cylindrical shape. The gas sampling tip may comprise three gas receiving apertures evenly spaced around the distal end of the sampling tip. Preferably, each portion of the body located between the gas receiving apertures forms a flute, wherein the flutes are substantially evenly spaced around the circumference of the distal end portion of the gas sampling tip.

The gas sampling conduit may comprise a first lumen through which gas may flow and a second lumen in which a flexible, resilient structural support member is located to allow the gas sampling conduit to be bent to a desired shape and to substantially retain the desired shape. Alternatively, the gas sampling conduit comprises a tube wall in which a flexible, resilient structural member is located. The gas sampling conduit may be co-extruded with the structural member to encase the structural member within the wall of the conduit. The structural support member may comprise a metal filament. For example, the structural support member may comprise a wire. The wire may be at least partially formed from stainless steel, aluminium or nickel titanium.

In accordance with a seventh aspect, there is provided a gas sampling interface comprising a gas sampling conduit comprising a gas inlet, a gas outlet, and a malleable spine that allows the gas sampling tube to be bent to a desired shape; wherein the gas sampling interface further comprises a removable gas sampling tip comprising at least one gas receiving aperture in fluid communication with the gas inlet of the gas sampling conduit.

Preferably, the malleable spine is semi-rigid to allow the gas sampling conduit to be bent to a desired shape and to substantially hold that shape. In one form, the malleable spine comprises a wire. The wire may at least partially formed from stainless steel, aluminium or nickel titanium.

Preferably, the gas sampling tip comprises a body comprising a substantially circular cross-section and further comprising at least three gas receiving apertures formed in the body, wherein each gas receiving aperture extends from a distal end of the body and along a side surface of the body, and wherein the gas receiving apertures are evenly spaced circumferentially around the body to form a flute between adjacent gas receiving apertures.

In accordance with an eighth aspect, the invention provides a gas sampling tip to connect to an inlet of a gas sampling conduit, wherein the sampling tip comprises a body comprising a substantially hollow interior region configured to be in fluid communication with the inlet of the gas sampling conduit when connected to the gas sampling conduit, and wherein the body also comprises a distal end portion comprising a distal end wall and an outer side surface, wherein the gas sampling tip further comprises a gas receiving aperture connected to the interior region and configured to receive gases exhaled or expired by a patient, and wherein the gas receiving aperture extends around substantially the entire outer periphery of the outer side surface.

Preferably, the gas sampling tip end wall is supported by a centrally disposed support member connected to at least one interior wall of the body and wherein the gas receiving aperture extends around the entire outer periphery of the outer side surface. The body of the sampling tip may be substantially cylindrical and the gas receiving aperture forms a ring-like aperture around the outer side surface of the body. In one form, the body of the sampling tip is substantially cylindrical and the gas receiving aperture forms a helical-like aperture around the outer side surface of the body.

In accordance with a ninth aspect, the invention provides a gas sampling tip comprising a body comprising a substantially hollow interior region, wherein the body comprises one or more side walls forming an outer side surface of the body, a proximal end configured to connect to a gas sampling conduit such that the hollow interior region is in fluid communication with the gas sampling conduit, and a distal end defined by an end wall, and wherein the body further comprises a gas receiving aperture forming an opening to the hollow interior region of the body, wherein the gas receiving aperture extends substantially around the entire outer periphery of the outer side surface of the body.

In one form, the end wall is substantially transverse to and offset from the gas receiving aperture. Optionally, the end wall is integrally formed with the body. The cross-section of the wall may be the same as, or greater than, the cross-section of the gas receiving aperture. In one form, the end wall is longitudinally offset at a distance equal to, or greater than, the width of the gas receiving aperture. Optionally, the end wall is cantilevered from a portion of the body by a support member, which may comprise a strut, pole, arm or elongate extension. In one form, the body is substantially cylindrical and the gas receiving aperture forms an annular ring around the body. Alternatively, the body is substantially cylindrical and the gas receiving aperture forms a helical arrangement around the body.

In accordance with a tenth aspect, the invention provides a respiratory therapy system for delivery high flow respiratory therapy to a patient and sampling exhaled or expired gases from the patient, wherein the system comprises: a breathing apparatus comprising a patient interface and a breathing gas delivery tube connected to a gas source to deliver high flow breathing gas from the gas source via the breathing gas delivery tube to the patient through the patient interface; and a gas sampling interface comprising a conduit comprising a first end in fluid communication with a respiratory gas monitor and a second, distal end comprising at least one inlet for receiving exhaled or expired breathing gases from the patient. In some forms, the breathing apparatus provides breathing gas to the patient at a flow rate of between about 15 to about 150 L/min. Optionally, the breathing apparatus provides breathing gas to the patient at a flow rate of between about 30 to about 120 IL/min, or between about 60 to about 110 IL/min. or between about 50 to about 150 L/min, or between about 60 to about 100 L/min. In some forms, the breathing apparatus provides high flow breathing gas to the patient at a flow rate of greater than about 30 L/min, greater than about 40 L/min, greater than about 50 L/min. greater than about 60 L/min, or greater than about 70 L/min. Optionally, the system is configured to delivery breathing gas to a neonatal infant patient at a flow rate of about 2 L/min/kg.

In one form, the conduit comprises a flexible resilient support structure that allows the distal end portion to be manipulated to a desired shape and to be selectively directed toward the patient's nose or mouth. The flexible resilient support structure may comprise a wire located within the conduit that allows at least a portion of the conduit to be bent to form a hook-like shape. Optionally, the wire has a smaller diameter than an internal diameter of the conduit and wherein a gap is formed between the wire and an internal wall of the conduit to allow gas to flow along the conduit. In one form, the conduit comprises a first, gas receiving lumen and a second, support lumen. In this form, the wire is located in at least a portion of the support lumen. Optionally, the wire is co-extruded with the gas sampling conduit. In one form, the wire is located in the distal end portion of the conduit to allow the distal end portion to be bent to form a hook-like shape.

In one form, the system also comprises an attachment member to attach the gas sampling interface to the breathing apparatus. Optionally, the attachment member is integral with or attached to the breathing gas delivery tube and comprises: a sleeve that at least partially encloses a portion of the breathing gas delivery tube; wherein the sleeve comprises at least one clip located on an outer surface of the sleeve for receiving a portion of the conduit to attach the conduit to the breathing apparatus. In one form, the sleeve comprises a pair of clips that are offset from each other. Each clip may comprise a hook comprising a tube receiving region within which a portion of the conduit may be located to follow a tortuous path. Preferably, the hooks face in opposite directions to each other.

In one form, the gas sampling interface further comprises a tip located at the distal end of the conduit, wherein the tip comprises a substantially hollow body comprising at least one gas receiving aperture to receive gases exhaled or expired by a patient, wherein the gas receiving aperture is in fluid communication with the at least one inlet of the conduit, and wherein the body of the tip further comprises a distal end portion comprising a distal end surface and an outer side surface. At least one gas receiving aperture may be formed both in the distal end surface and outer circumferential side surface such that the gas receiving aperture extends from the distal end surface and along the outer side surface. In one form, at least one gas receiving aperture forms an elongate opening in the distal end portion of the gas sampling tip.

In one form, the body of the tip comprises a substantially cylindrical shape. Optionally, the distal end of the gas sampling tip is outwardly curved. Preferably, the distal end portion of the gas sampling tip is substantially bulbous.

In one form, the gas sampling tip comprises at least three gas receiving apertures evenly spaced around the distal end of the sampling tip. Optionally, each portion of the body located between the gas receiving apertures forms a flute, wherein the flutes are substantially evenly spaced around the circumference of the distal end portion of the gas sampling tip.

Preferably, the breathing apparatus is a nasal cannula.

Optionally, the patient receiving therapy from the breathing apparatus is apnoeic.

In accordance with an eleventh aspect, the invention provides a gas sampling interface for use with a high flow respiratory gas delivery system, the gas sampling interface comprising: a conduit comprising: a first end in fluid communication with a respiratory gas monitor; and a second, distal end comprising at least one inlet for receiving exhaled or expired breathing gases from the patient; a gas sampling tip located at the distal end of the conduit and comprising a substantially hollow body comprising at least one gas receiving aperture to receive gases exhaled or expired by a patient, wherein the gas receiving aperture is in fluid communication with the at least one inlet of the conduit, and wherein the body of the tip further comprises a distal end portion comprising a distal end surface and an outer side surface. Preferably, at least one gas receiving aperture is formed both in the distal end surface and outer circumferential side surface such that the gas receiving aperture extends from the distal end surface and along the outer side surface to form an elongate opening in the distal end portion of the gas sampling tip.

Optionally, the distal end portion of the gas sampling tip is substantially bulbous.

In one form, the gas sampling tip comprises three gas receiving apertures evenly spaced around the distal end of the sampling tip. Optionally, each portion of the body located between the gas receiving apertures forms a flute, wherein the flutes are substantially evenly spaced around the circumference of the distal end portion of the gas sampling tip.

In one form, the gas sampling conduit connects to a gas sampling tube of the respiratory gas monitor via a luer.

In another form, the gas sampling conduit connects directly to an inlet of the respiratory gas monitor.

In one form, the gas sampling interface is configured to receive exhaled or expired gas of a patient who is receiving breathing gas, from a breathing apparatus, at a flow rate of between about 15 to about 150 L/min. Optionally, the gas sampling interface is configured to receive exhaled or expired gas of a patient who is receiving breathing gas, from a breathing apparatus, at a flow rate of between about 30 to about 120 L/min. or between about 60 to about 110 L/min, or between about 50 to about 150 L/min, or between about 60 to about 100 L/min. In some forms, the gas sampling interface is configured to receive exhaled or expired gas of a patient who is receiving high flow breathing gas, from a breathing apparatus, at a flow rate of greater than about 30 L/min, greater than about 40 L/min, greater than about 50 L/min, greater than about 60 L/min, or greater than about 70 L/min.

Optionally, the gas sampling interface is configured to receive breathing gas of a neonatal infant patient who is receiving breathing gas, from a breathing apparatus, at a flow rate of about 2 L/min/kg.

In accordance with a twelfth aspect, the invention provides a breathing apparatus comprising: a nasal cannula having a manifold for supporting at least one nasal prong or outlet that extends from the manifold and that is to be received in a user's nare; a gas delivery tube in fluid communication with the at least one nasal prong or outlet for supplying breathing gas through the at least one nasal prong or outlet; and an attachment member for attaching a gas sampling interface to the nasal cannula, wherein the attachment member is integral with or attached to the breathing gas delivery tube or manifold and comprises: a sleeve that at least partially encloses a portion of the breathing gas delivery tube or manifold; wherein the sleeve comprises at least one clip for receiving a portion of a gas sampling conduit to attach the conduit to the breathing apparatus. Optionally, the sleeve comprises a substantially arcuate inner surface to enclose a portion of the breathing gas delivery tube. The clip may be located on an outer surface of the sleeve. Preferably, the sleeve comprises a pair of clips that are offset from each other. Each clip optionally comprises a hook comprising a receiving region within which a portion of the conduit may be located to follow a tortuous path. Preferably, the hooks face in opposite directions to each other. In one form, the conduit is substantially loosely held within each clip, so that disconnection of the conduit from one clip allows the conduit to be slid through the other clip to adjust the length of the free end portion of the conduit that extends between the distal end of the conduit and the sleeve. Optionally, the sleeve comprises a substantially C-shaped cross section.

In one form, the gas delivery tube supplies breathing gas to a patient at a flow rate of between about 15 to about 150 L/min. Optionally, the gas delivery tube supplies breathing gas to the patient at a flow rate of between about 30 to about 120 L/min. or between about 60 to about 110 L/min, or between about 50 to about 150 L/min, or between about 60 to about 100 L/min. In some forms, the gas delivery tube provides high flow breathing gas to the patient at a flow rate of greater than about 30 L/min. greater than about 40 L/min, greater than about 50 L/min, greater than about 60 L/min, or greater than about 70 L/min.

Optionally, the gas delivery tube supplies breathing gas to a neonatal infant patient at a flow rate of about 2 L/min/kg.

In accordance with a thirteenth aspect, the invention provides a gas sampling tip to removably connect to a distal end of a gas sampling conduit, wherein the sampling tip comprises a body comprising a substantially hollow interior region configured to be in fluid communication with the inlet of the gas sampling conduit when connected to the gas sampling conduit, and wherein the body also comprises a distal end portion comprising a distal end surface and an outer side surface, wherein the gas sampling tip further comprises at least one gas receiving aperture connected to the hollow interior region to receive gases exhaled or expired by a patient, and wherein the gas receiving aperture is in fluid communication with the substantially hollow interior region of the body. At least one gas receiving aperture may be formed both in the distal end surface and outer circumferential side surface such that the gas receiving aperture extends from the distal end surface and along the outer side surface. Optionally, at least one gas receiving aperture forms an elongate opening in the distal end portion of the gas sampling tip.

In one form, the distal end of the gas sampling tip is outwardly curved. Optionally, the distal end portion of the gas sampling tip is substantially bulbous. In one form, the gas sampling tip has a substantially cylindrical shape. In one form, the gas sampling tip comprises a body having a substantially cylindrical shape and a substantially bulbous distal end.

In one form, the gas sampling tip comprises three gas receiving apertures evenly spaced around the distal end of the sampling tip 50. The gas sampling tip according to claim 49, wherein each portion of the body located between the gas receiving apertures forms a flute, wherein the flutes are substantially evenly spaced around the circumference of the distal end portion of the gas sampling tip.

Optionally, the gas sampling tip is configured to receive expired or exhaled gas from a patient that is supplied with breathing gas, by a breathing apparatus, at a flow rate of between about 15 to about 150 L/min. Optionally, gas sampling tip is configured to receive expired or exhaled gas from a patient that is supplied with breathing gas, by a breathing apparatus, at a flow rate of between about 30 to about 120 L/min, or between about 60 to about 110 L/min. or between about 50 to about 150 L/min, or between about 60 to about 100 L/min. In some forms, the breathing apparatus provides high flow breathing gas to the patient at a flow rate of greater than about 30 L/min, greater than about 40 L/min, greater than about 50 L/min. greater than about 60 L/min. or greater than about 70 L/min.

Optionally, the gas sampling tip is configured to receive expired or exhaled gas from a neonatal infant patient that is supplied with breathing gas, by a breathing apparatus, at a flow rate of about 2 L/min/kg.

In accordance with a thirteenth aspect, the invention provides a method of producing a dual lumen gas sampling conduit comprising a body comprising a gas lumen and a wire lumen, wherein the conduit is produced by co-extruding a wire with the conduit body to locate the wire within the wire conduit.

In accordance with a fourteenth aspect, the invention provides a method of producing a dual lumen gas sampling conduit comprising a body comprising a gas lumen and a wire lumen, wherein the conduit is produced by over-moulding the conduit around the wire to located the wire within the wire conduit.

In accordance with a fifteenth aspect, the invention provides a method of sampling breathing gas from an apnoeic patient receiving high flow respiratory therapy using the respiratory therapy system of the tenth aspect of the invention, wherein the method comprises the steps of: locating an inlet of a gas sampling interface proximate to the patient's airway, receiving a sample of breathing gas through the inlet, and using the respiratory gas monitor to determine whether the patient's airway(s) are patent.

Optionally, the respiratory gas monitor may also measure the volume or one or more constituents of the breathing gas.

The invention consists in the foregoing and also envisages constructions of which the following gives examples only.

BRIEF DESCRIPTION OF THE DRAWINGS

Specific embodiments and modifications thereof will become apparent to those skilled in the art from the detailed description herein having reference to the figures that follow, of which:

FIG. 4 shows an alternative embodiment of a gas sampling interface.

FIG. 5 shows an alternative embodiment of a gas sampling interface.

FIG. 6 shows an alternative embodiment of a gas sampling interface.

FIG. 53 shows an alternative embodiment of a clip for a gas sampling interface.

FIG. 54 shows an end view of an alternative embodiment of a clip for a gas sampling interface.

FIGS. 68A and 68B are side views of another form of gas sampling tip.

FIGS. 69A and 69B are side views of another form of gas sampling tip.

DETAILED DESCRIPTION

Figure 1:
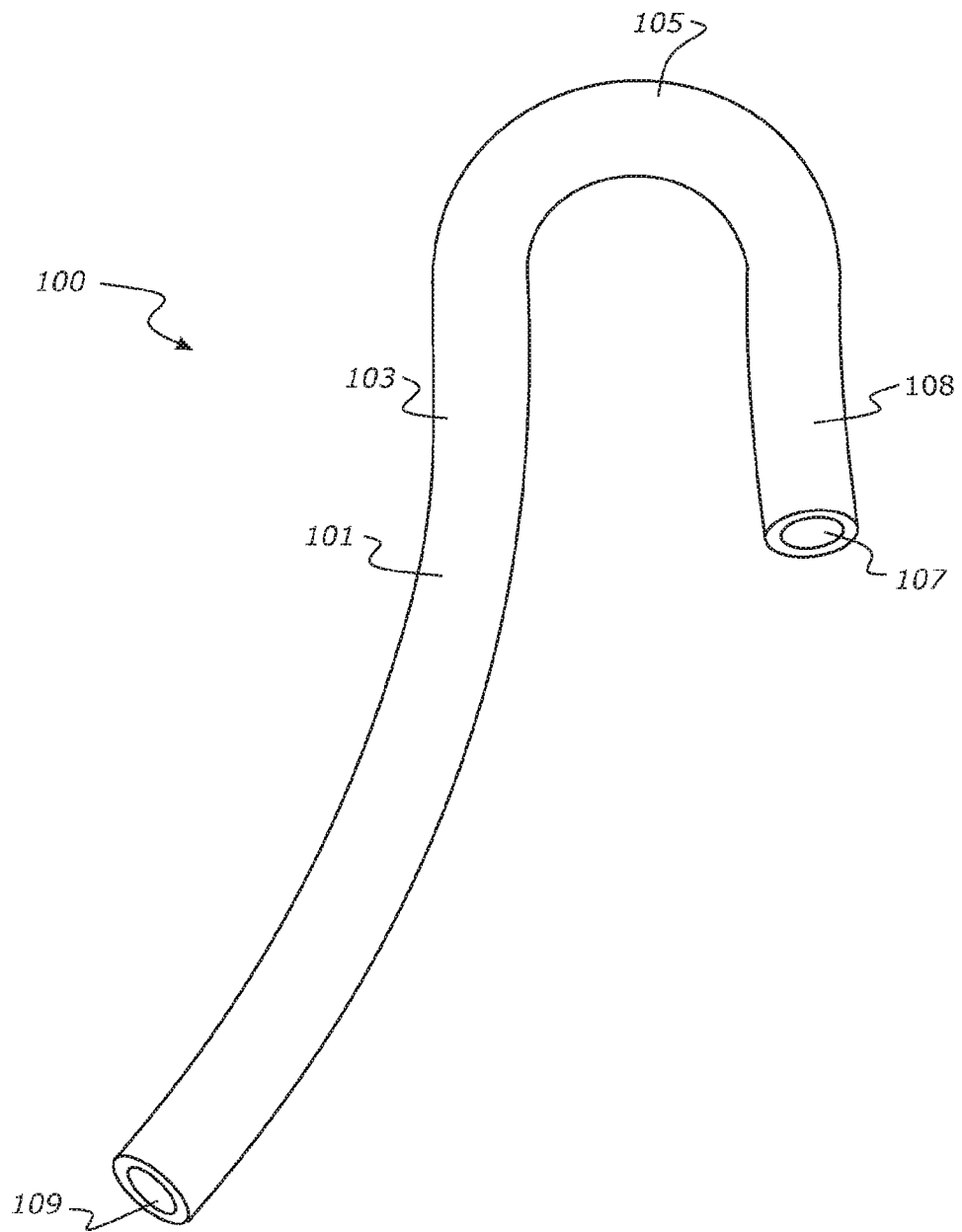
FIG. 1 shows one embodiment of a gas sampling interface.

In general, the invention relates to a respiratory gas delivery and sampling system, a gas sampling system, a gas sampling interface and a gas sampling tip that may be used to sample exhaled and/or expired gases from a patient. The gas sampling system comprises a respiratory gas monitor in fluid communication with the gas sampling interface, which comprises the gas sampling tip of the invention. The gas sampling interface comprises a gas sampling conduit and the gas sampling tip is located at a free end of the conduit. The gas sampling interface may be configured to allow the gas sampling tip to be selectively positioned at or in the mouth or a nare of the patient's nose. The sampling tip comprises at least one inlet to receive exhaled or expired gas from a patient. The sampling tip may also be configured to comprise a shield or structure that helps prevent fluid, such as moisture or bodily fluids from entering into the sampling tip. Additionally or alternatively, the sampling tip may be configured to prevent or reduce the likelihood that the tip will suction onto the patient, such as the patient's tongue or cheek. In some forms, the shield or structure of the sampling tip may help prevent fluid ingress and may also help prevent suctioning on the patient. The gas sampling interface may include a filter located at the tip or at any other location along the gas sampling lumen of the sampling interface to prevent fluid, such as moisture or bodily fluids from entering into or moving along the gas sampling lumen and into the respiratory gas monitor.

Various gas sampling interfaces/breath sampling interfaces for use with a respiratory gas monitor of a gas sampling system will now be described. It should be appreciated that any of these interfaces may be used in combination with (or may be attached to) a respiratory gas delivery and sampling system comprising a breathing apparatus for delivering breathing gas to a patient. Each gas sampling interface may sample exhaled and/or expired gases from a patient. Each interface may be used to sample Nitrogen, $O_2$, anaesthetic gases and/or $CO_2$. Alternatively, two sampling interfaces may be used, one for sampling nitrogen and one for sampling $CO_2$. The interfaces will sample exhaled and/or expired gases and could be fluidly connected to separate gas analysers to identify $CO_2$ and Nitrogen in the exhaled and/or expired gases. It will be understood that expired gases are gases that exit the patient's lungs due to gases exchange in the lungs. Expired gases are gases that exit from (such as gases that are diffused from) the lungs when the patient is not spontaneously breathing, such as when the patient is apnoeic. Exhaled gases are gases that are pushed up from the patient's lungs due to spontaneous breathing by the patient.

The gas sampling interfaces of the invention that are disclosed herein may be disposable or re-usable. A filter may be attached to the end of the sampling interface, between the inlet to the interface and sampling conduit, to allow the sampling conduit to be reused. The gas sampling interface 100 and/or the filter may be changed for each patient. The gas sampling interfaces and gas sampling conduits disclosed may be used alone to engage with a part of a patient's face or may be attachable to a breathing apparatus, such as a nasal cannula, nasal mask, oral mask, or other form of patient interface for delivering breathing gas to a patient.

The gas sampling interface of the invention may be used with a breathing apparatus that provides high flow breathing gas to a patient. Typically, the breathing apparatus provides high flow breathing gas to an apnoeic patient, such as during anaesthesia, but the apparatus and interface may also be used to measure breathing gas of a spontaneously breathing patient. To provide breathing gas at high flow, the gas may typically flow at between about 15 L/min to about 150 L/min for an adult patient. Example flow rates of breathing gas supplied to a patient by the patient interface are between about 15 to about 150 L/min; about 30 to about 120 L/min; about 40 to about 100 L/min; about 50 to about 80 L/min; about 60 to about 100 L/min; and about 35 to about 75 L/min. In other examples, high flow breathing gas may be supplied to a patient at a flow rate of between about 30 to about 120 L/min, or between about 60 to about 110 L/min, or between about 50 to about 150 L/min, or between about 60 to about 100 L/min. In some forms, high flow breathing gas may be supplied to the patient at a flow rate of greater than about 30 L/min, greater than about 40 L/min. greater than about 50 L/min, greater than about 60 L/min. or greater than about 70 L/min. Flow rates that may be considered to be 'high flow' may vary somewhat depending on the size of the patient. For example a neonatal infant patient may be supplied with high flow breathing gas at a flow rate of about 2 L/min/kg. In some forms, the gas sampling interface is configured to have an adaptable shape and/or position relative to the breathing apparatus. By providing the interface with an adaptable shape, it is possible to manipulate the interface to best engage with the patient, such as by hooking onto a patient's lip, cheek, or nare. It is also possible to adjust the direction and location of the interface by manipulating the interface to be directed in the proximity of the patient's mouth or nose. This allows a clinician to select the best location for the interface and to easily change that location, if required. By providing an interface with an adjustable position in relation to the breathing apparatus, it is possible to direct the interface toward a patient's mouth or nose, as described above, and it may also be possible to readily adjust the length of the free end portion of the interface in relation to the breathing apparatus. An interface with a free end portion having an easily adjustable length allows the interface to be used for patients having different sized faces. For example, a gas sampling interface of the invention would need a shorter free end portion when used for a small child than when used for a large adult. Where the sampling interface of the invention is adjustable in shape and/or position, the interface is particularly versatile and is useful for a wide range of patients and medical procedures. For example, the sampling interface provides a selectively positionable device that is able to be moved between the mouth and narc depending on whether the patient's mouth is open and the type of medical procedure being undertaken.

FIG. 1 shows one embodiment of a gas sampling interface 100. The gas sampling interface 100 comprises a gas sampling conduit 101 having a body 103, which is preferably formed partially or entirely from a substantially cylindrical wall, as shown in FIG. 1 to provide the body 103 with a substantially circular cross-section along its length. The conduit shown in FIG. 1 has a single lumen extending along the length of the conduit and is therefore referred to in this specification as a single lumen conduit. However, the gas sampling conduit may comprise one, two or more lumens within the conduit. Gas sampling conduits that comprise two lumens within the conduit are referred to in this specification as dual lumen conduits. The two lumens of a dual lumen conduit may both extend substantially along the entire length of the conduit or the first, support lumen, may extend only partially along the length of the conduit, as will be described in further detail later in this specification, and the second, gas lumen, may extend substantially along the entire length of the conduit.

The size of the conduit and its lumen(s) is important to its operability. It will be appreciated that the external diameter of the conduit will be determined by the required inner or internal diameter of the lumen(s) and the materials from which the conduit is made. It is important that the internal diameter(s) of the lumen(s) is/are not so large that the conduit is too big for a patient to use comfortably and to be easily manipulated to a desired shape and position. It is also important that the internal diameter(s) of the lumen(s) is/are not so small in relation to the external diameter of the conduit that the gas flow through the conduit is unduly impeded or the walls of the conduit are so thick that it becomes difficult to manipulate the conduit to a desired shape and to substantially retain the conduit in that shape.

Preferably, the body of the gas sampling conduit 101 has an external (or outer) diameter that is between about 2.5 mm and about 5.0 mm. The diameter may be about 3.5 mm to about 4 mm, or about 3.0 mm to about 3.5 mm, or about 3.1 mm to about 3.4 mm, or about 3.2 mm to about 3.3 mm. Preferably, the body of the gas sampling conduit has an external diameter of about 3.8 mm. The internal diameter of the gas sampling conduit (where the conduit has a single lumen) is preferably between about 0.5 mm to about 2 mm to correspond to the internal diameter of the main sampling line or gas sampling tube of a respiratory gas monitor without causing additional resistance to flow. For example, the internal diameter of the conduit may be about 1.2 mm to 1.4 mm. Preferably, the internal diameter is about 1.4 mm.

In one form, the tubular body of the gas sampling conduit 101 has a wall thickness of about 0.9 mm. In this form, the body 103 of the conduit may have an external diameter of about 3.0 mm and an internal diameter of about 1.2 mm. The gas sampling conduit of this form preferably comprises a single gas lumen within the conduit.

In one form, the external diameter of a dual lumen conduit is between about 2.5 mm and about 5.0 mm. In one form, the external diameter may be about 3.2 mm. The diameter may be about 3.5 mm to about 4 mm, or about 3.0 mm to about 3.5 mm, or about 3.1 mm to about 3.4 mm, or about 3.2 mm to about 3.3 mm. Preferably, the body of the gas sampling conduit has an external diameter of about 3.8 mm. In another form, the external diameter is about 4.0 mm. The lumens within the conduit may have the same diameter or differing diameters. For example, the lumens may each have an internal diameter of about 1.2 mm. In one form, a dual lumen conduit has an external diameter of about 3.8 mm and each lumen has an internal diameter of about 1.4 mm. Alternatively, the first lumen may have a diameter of about 1.0 mm and the second lumen may have a diameter of about 1.3 mm, for example. In yet another form of dual lumen conduit, the conduit may have an external diameter of about 3.8 mm. In this form, the first lumen may have an internal diameter of about 0.6 mm and the second lumen may have an internal diameter of about 1.4 mm.

It is desirable that the external diameter of the conduit is relatively small so as to take up less room in the patient's mouth.

Figure 2:
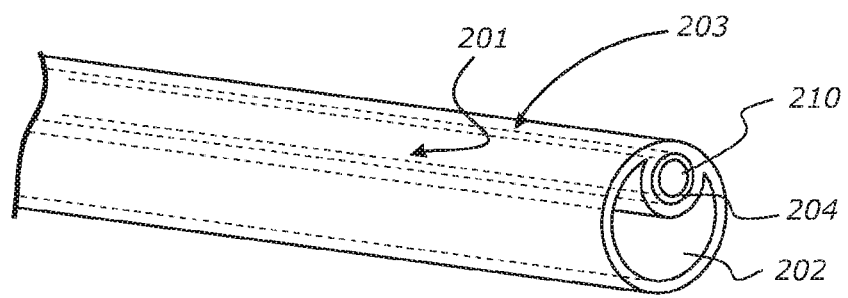
FIG. 2 shows an alternative embodiment of a gas sampling interface.

In one embodiment, as shown in FIG. 2, the gas sampling interface comprises a dual lumen conduit 201. This conduit is similar to the conduit shown in FIG. 1 and like numbers are used to indicate like parts with the addition of 100. In the embodiment shown in FIG. 2, the conduit body 203 has a circular cross-section along its entire length. The conduit comprises a flexibly resilient support structure that allows the conduit to be manipulated to a desired shape, such as a hook-like shape. The support structure may take many different forms. For example, the support structure may comprise a wire, rod, or strip of flexible resilient material (such as a metallic material) that extends along at least a portion of the conduit, preferably at the free end portion of the conduit. In one form, the conduit comprises a first, support lumen in which the support structure, such as a wire, may be located. The wire may be inserted into the lumen or co-extruded with the conduit or a portion of the conduit may be over-moulded around the wire. In other forms, the support structure may be formed around the external wall of the conduit or the external wall may be made from a suitable material that provides a support structure.

Figure 9:
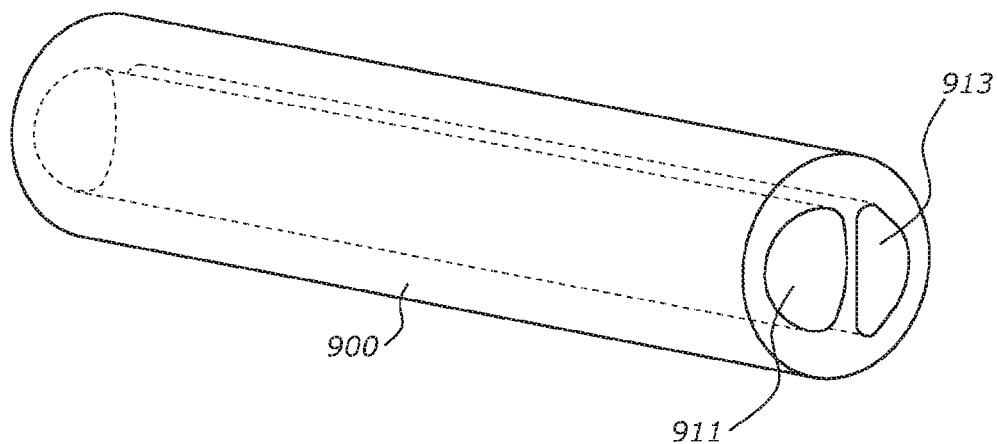
FIG. 9 shows an alternative embodiment of a gas sampling interface.
Figure 13:
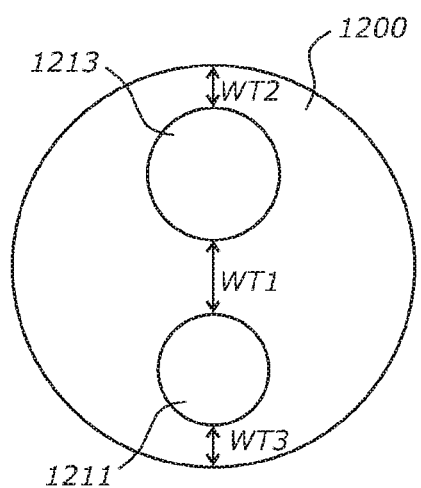
FIG. 13 shows a horizontal cross section of an alternative embodiment of a gas sampling interface.

In the embodiment shown in FIG. 2, the conduit comprises a first support lumen 204, for housing a support structure in the form of a wire within the first lumen. The first, support lumen or wire lumen has a substantially circular cross-section along its entire length. A second, gas lumen 202 for receiving expired and/or exhaled gas, has a substantially crescent-shaped cross-section along its entire length. The first support lumen 204 lies within and at one side of the second lumen 202, such that the crescent shaped cross-section of the second, gas lumen is formed by the shape of the open space around the first support lumen 204. In alternative embodiments of dual lumen conduits, each lumen may have a substantially D-shaped cross-section (as shown in FIG. 9), or a substantially semi-circular cross-section, or a substantially circular cross-section along its entire length. Preferably, the cross-sectional area of the gas lumen, is greater than about 1.3 mm2. Preferably, the height of the gas lumen is greater than about 1.5 mm. Preferably, the width of the gas lumen is greater than about 1.5 mm. FIG. 13 shows a dual lumen conduit in which each lumen comprises a substantially circular cross-section along its length.

The gas sampling conduit 101 may consist of or comprise a polymeric material. The material may be any suitable medical material, such as PVC, TPU, or silicone. The hardness of the material is preferably about 30 to about 85 on the shore A hardness scale. The material is preferably clear so that the interior of the conduit is visible, for example, to see if saliva, blood, or other bodily fluids that may be present, have been drawn into the conduit. The sampling conduit material may comprise a hardness of less than 90 on the Shore A hardness scale. This reduces the torque of the conduit on the patient end of the interface (compared with a stiffer conduit) and so reduces the chance of the sampling conduit falling out of the patient's mouth or nare. A softer material is also more comfortable on the patient's face. The material may comprise polyurethane or silicone. Alternatively, the material may comprise PVC.

The gas sampling conduit 101 has at least one inlet or gas receiving aperture or opening 107 for receiving gases exhaled and/or expired by a patient. The inlet 107 may be formed in the distal end portion of the conduit, such as in the external wall of the conduit or at the distal end of the conduit. In the embodiment shown in FIG. 1, the inlet is located at the distal end 108 of the body 103 of the conduit. The conduit also has an outlet 109 for delivering the exhaled and/or expired gases to a respiratory gas monitor, which may be a capnogram/capnograph or other form of gas monitor, to monitor $CO_2$ levels and/or levels of other respiratory gases. The outlet 109 may be in fluid communication with a gas sampling tube or gas sampling line that is fluidly connected to a respiratory gas monitor. In another form, the outlet of the gas sampling conduit may directly attach to a respiratory gas monitor.

The conduit is preferably at least 30 cm long. This means if the patient lies on the conduit, any connector/luer that connects the conduit to a gas sampling tube of a respiratory gas monitor is not positioned under the patient's head, which may be uncomfortable.

The conduit 101 may be configured to adopt a desired shape to engage with a patient's face so that the conduit can be easily attached to/engaged with and detached from/ disengaged with the patient's face. In a preferred form, the conduit may be shaped into a hook-like shape to hook over a patient's lip or teeth or around a patient's cheek or nare. In this form, it may be unnecessary to tape the conduit to a patient's face so that the conduit may be quickly and easily located at the desired position and then quickly and easy removed after use.

In one form, as shown in FIGS. 1 and 3 to 6.10 to 12, 14 to 26.37 to 46.48, 52, 55, 70 and 71 for example, the conduit 101 comprises a hook portion 105, which is preferably located at the distal end portion of the conduit. In one form, the tubular structure of the conduit may comprise a flexible, resilient support structure that allows a portion of the conduit to be formed into a hook-like shape and to substantially maintain that position. In another form, the tubular structure of the conduit may be attached to a rigid or semi-rigid hook to form a conduit having a hook portion. In yet another form, the conduit may be manufactured in such a way as to include a hook portion such as an end portion formed in a hook-like shape. The hook portion 105 forms a hook-like shape for engaging with part of a patient's face.

The hook portion 105 of the conduit 101 is adapted to engage a patient's face at or near an orifice of the patient's face. In one embodiment, the hook portion 105 is adapted to engage with a patient's mouth or part of the patient's mouth. In use, the hook portion 105 passes around the patient's cheek and into the patient's mouth. The hook portion 105 enables the tip 108 and the inlet 107 of the conduit 101 to be suspended inside the patient's mouth, if desired. In another embodiment, the hook portion 105 is adapted to engage with the patient's nose or part of the patient's nose, such as their nostril or nare. In this embodiment the tip 108 or inlet end of the conduit may be suspended or positioned at least partially inside the patient's nostril or nare or proximate to the nostril/nare.

The hook portion of the conduit may comprise a semi-rigid or rigid material that forms a flexible, resilient support structure or spine that allows the conduit to be bent or manipulated to a desired shape. In some forms, the conduit may be configured to substantially maintain that desired shape indefinitely. In other forms, the conduit may be configured to substantially maintain the desired shape until it is manipulated by a user to form a different shape.

In one form, the flexible, resilient support structure may comprise a length of malleable wire, such as a cable or rod for example, that is located within the conduit. The wire is preferably a metallic wire. The wire may extend along one or more portions of the conduit or the wire may extend along substantially the entire length of the conduit. A distal end or patient end of the wire may be coated in a soft material so as to not graze or scratch the patient's face. Alternatively, the patient end of the wire may be positioned sufficiently far back in the conduit so that it does not extend beyond the distal end of the conduit. In a further alternative, the end of the wire may be sealed inside the conduit wall. In a further alternative, the wire may be located within the support lumen/wire lumen of a dual lumen conduit and the patient end of the wire may be fixed at one or more points along the inner wall of the wire lumen to hold the wire in place and prevent the wire from moving out of the lumen.

In another form, the conduit may comprise at least one lumen that acts as both a wire/support lumen and a gas lumen. In this form, the conduit may comprise a wire having a smaller diameter than the internal diameter of the lumen. The wire may be held inside the lumen at one or more locations. In this arrangement, the conduit may bend around the wire, but one or more gaps are provided between the wire and the internal wall of the lumen so that gas can pass along the lumen to be sampled by the respiratory gas monitor. The lumen cannot completely seal around the wire, which is non-compressible, preventing full obstruction.

A length of malleable wire may occupy at least the hook portion of the conduit or the wire may extend along substantially the entire length of the conduit. For example, in the dual lumen conduit shown in FIG. 2, the wire 210 may occupy one or more portions of the first support lumen 204 of the dual lumen conduit 201, or the wire may extend along substantially the entire length of the first support lumen 204. The presence of the wire 210 provides rigidity to the dual lumen conduit 201 and gas sampling interface 200. The wire 210 is also flexible to allow the first support lumen 204, and therefore the conduit 201, some degree of adjustment to further customise the shape of the interface to the patient's face. In particular, the shape of the hook portion is adjustable by flexing the wire 210 to form a desired hook shape for engaging with the patient's face.

The wire may comprise a stainless steel wire that can be bent/reshaped multiple times without breaking. The wire may be between about 0.4 mm to 1.0 mm in diameter and is preferably about 0.6 mm or 0.7 mm in diameter. Preferably, the wire is grade 304. These properties create suitable malleability to allow the user to reshape/bend the conduit by hand easily. In another form, the wire comprises aluminium wire. In another form, the wire comprises nickel titanium wire.

In one form, the wire 210 is positioned on the inside curve of the hook portion. This is to reduce the risk of kinking the gas sampling conduit when bent. Alternatively, the wire 210 may be positioned on the outside curve of the hook portion or along the side or at any other orientation or position about the length of the conduit.

Figure 12:
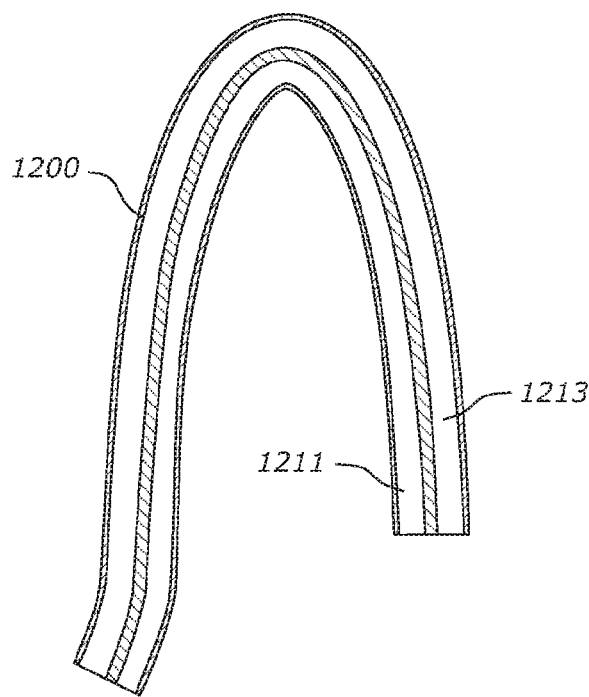
FIG. 12 shows a vertical cross section of an alternative embodiment of a gas sampling interface.

FIGS. 12 and 13 show another form of dual lumen conduit 1200. A first, wire/support lumen 1211 contains a wire to create a malleable shape. A second, gas lumen 1213 is connectable to be in fluid communication with the gas sampling tube in fluid communication with the respiratory gas monitor, or to be directly in fluid communication with the respiratory gas monitor (where the sampling system does not include a sampling tube between the monitor and sampling conduit). In this dual lumen conduit, the conduit is preferably bent or formed with one conduit located on the inside of the curved of the hook portion, and one conduit located on the outside of the curve. This arrangement creates a lower resistance to flow than if the lumens are positioned side by side around the curve. The wire is fed through the first lumen 1211, which is located on the inside curve of the hooked portion of the conduit. This reduces the risk of the wire piercing the conduit wall and also reduces the risk of the wire kinking the conduit as it is bent.

FIG. 13 shows a cross section of a dual lumen conduit, comprising a first, wire lumen 1211 and a second gas lumen 1213. In one form, the gas lumen 1213 may comprise an internal diameter of about 1.2 mm to correspond with the internal diameter of a gas sampling tube from an anaesthesia machine or other form of respiratory gas monitor or to corresponding with the inlet of a respiratory gas monitor. In another form, the gas lumen 1213 may have an internal diameter of about 1.4 mm and the wire lumen may have an internal diameter of about 0.6 mm. A smaller internal diameter will increase the resistance to flow and may increase the chance of a blockage occurring in the gas sampling conduit and causing an alarm. It will be appreciated that the internal diameter may optionally be chosen or designed to correspond with the internal diameter of the gas sampling tube from an anaesthesia machine or respiratory gas monitor or to correspond with the inlet of a respiratory gas monitor. However, the internal diameters of the lumen and external diameter of the conduit may vary, as described above.

The wire lumen 1211 may comprise an internal diameter of about 1.0 mm. This diameter is to fit the 0.7 mm wire. It will be appreciated that the internal diameter will be chosen or designed to accommodate the wire.

The outer diameter of the conduit may be about 3.1 mm. This diameter is chosen because it allows the conduit to comprise conduits having an internal diameter of 1.2 mm and 1.0 mm, as mentioned above, with adequate wall thicknesses. A conduit comprising a small outer diameter is desirable to reduce the size of the interface in the patient's mouth to improve patient comfort and allow the clinician greater accessibility in the mouth. A smaller diameter conduit also allows the interface to fit under a bite block.

As shown in FIG. 13, the lumens of the conduit may be preferably, but not necessarily, round or circular. Round lumens and lumens have a greater resistance to kinking. In one form, the wall thickness between the lumens WT1 may be greater than the exterior wall thickness WT2, WT3 of the lumens (the wall thickness of the conduit). This wall structure also reduces the risk of the kinks forming in the conduit when the conduit is bent, for example if the user reshapes the conduit to form a tighter bend in the hooked portion. In a preferred form, the gas sampling interface and gas sampling conduit comprises a dual lumen conduit having an external diameter of about 3.8 mm. The conduit includes a first, wire lumen having an internal diameter of about 0.6 mm (for receiving a wire having an external diameter of about 0.6 mm), and a second, gas lumen having an internal diameter of about 1.4 mm. Both lumens have a substantially circular cross-section.

In a dual lumen conduit, the wire preferably extends down the first, wire lumen within the conduit. In one form, the wire terminates part way along the lumen or conduit. For example, the wire may extend to about 60 mm from the free end of the conduit. In another form, the wire may extend substantially along the entire length of the conduit. Optionally, the wire is co-extruded with the tubular material of the conduit. When the conduit is bent, the free end of the wire may substantially align with the free end of the conduit (or may be slightly retracted from the free end of the conduit). Optionally, the free end of the wire in the bent conduit may also substantially align with the other end of the wire. This allows the maximum clamping force of the hooked portion of the conduit on the cheek. This design also minimises the rigid length that extends past the clamping point and so reduces the torque acting on the clamping point, which may dislodge the interface.

In one embodiment, the conduit is manufactured to include a hook portion. For example, during manufacture, the conduit may begin in a straight condition and may then be bent or formed into a hook shape using a jig. Heat may also be applied to the conduit for a period of time to set the conduit in shape. In another form, the conduit may be a thermoplastic tube. During manufacture, the conduit may be formed into a hooked shaped by beginning in a straight condition and before being bent or formed into a permanent modified hook shape using a jig and a short period of heat to set the conduit in shape.

In the embodiment shown in FIG. 1, the gas sampling interface 100 consists of the gas sampling conduit 101, which comprises a length of tube, in which the interface end of the sampling conduit is formed into the hooked shape shown in FIG. 1. This embodiment may be a single lumen conduit 1 interface or a dual lumen conduit interface. In other forms, the gas sampling conduit 101 may comprise a sampling tip, such as those described later in this specification, such that the conduit and tip in combination form the gas sampling interface.

Figure 3:
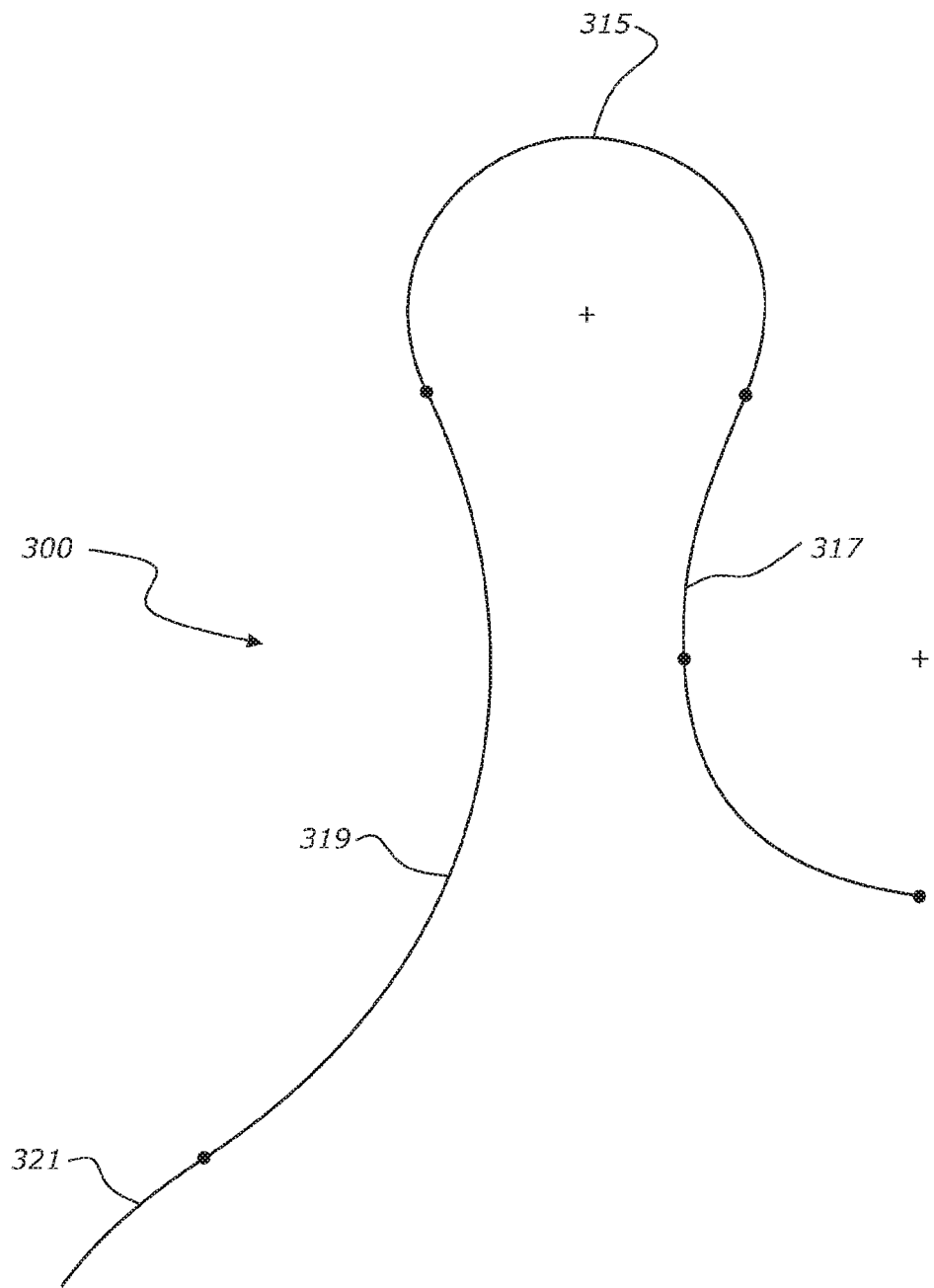
FIG. 3 shows a spline representative of the series of curves applied to the conduit of the interface.

FIG. 3 shows a spline representative of the series of curves applied to one embodiment of the conduit of the interface. The conduit may include additional curved portions immediately adjacent the hook, which bow toward the interior of the hook curve. That is, when viewed from the outside, the conduit has a generally concave portion 317 that leads into the generally curved or convex hook portion 315 that leads into another generally concave portion 319. The concave portions 317, 319 may have the same or different curvatures. The resulting combined shapes provide a central pinch area. A narrow pinch point may improve patient comfort by minimising the pinch point area. In use, the pinch area may contact the inside and outside of a patient's cheek or nostril and aid in retaining the interface. The additional curved portions and hook portion additionally provide some resistance to deformation of the conduit, which may apply a small reaction force to the inside and outside of a patient's cheek to aid in retention of the interface.

In one embodiment, the gas sampling interface or conduit may be hooked around cannula prongs to sample exhaled and/or expired gas from the patient's nares.

Figure 7:
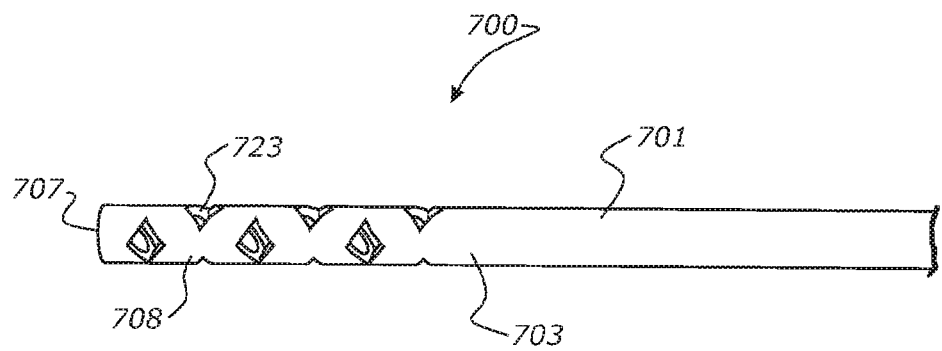
FIG. 7 shows an alternative embodiment of a gas sampling interface.
Figure 8:
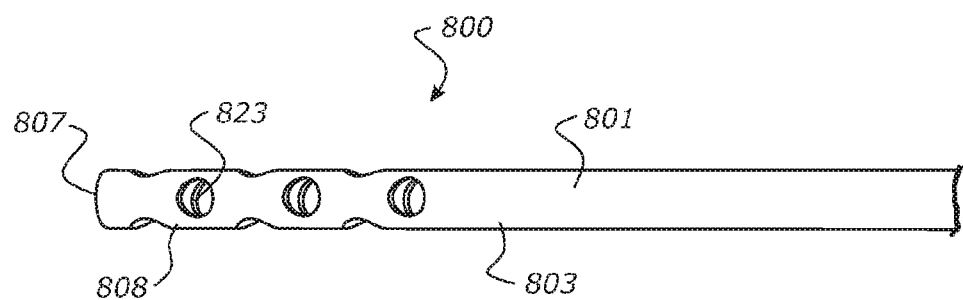
FIG. 8 shows an alternative embodiment of a gas sampling interface.

The embodiments shown in FIGS. 7 and 8 would be advantageous in this configuration because the openings would capture gases that are expired and/or exhaled from the patient's nares.

One of the additional concave portions 319 may extend between the curved or convex hook portion 315 and the distal end of the conduit. In use, this additional concave curved portions may displace the sampling conduit away from contact with the face of the patient. A further, convex curve portion 321 may optionally be provided between the additional concave curved portions and the distal end of the conduit. This further convex curve 321 may orientate the distal end of the conduit such that, in use, the sampling conduit extends approximately parallel to, and offset from, the cheek of the patient. This reduces the torque of the sampling conduit on the hook on the patient's face reducing or preventing the risk of dislodgement.

The other additional concave curved portion 317 may extend between the curved or convex hook portion 315 and the inlet of the conduit. This additional curved portion 317 may displace the inlet of the conduit away from contact with the interior of the patient's cheek. It is desirable to displace the inlet of the conduit away from the interior cheek of the patient in order to avoid, or at least substantially inhibit, full or partial clogging of the conduit and/or the sampling conduit with saliva or other bodily fluids that may be present, such as blood.

The hook shape may comprise a series of curves in a substantially 2-dimensional plane and include at least one curve or bend which curves substantially inwardly to form a hook. A hook shape may include a 'J', 'L', 'U', 'V', 'Ω', or 'hairpin' shaped conduit, or any combination thereof. That is, the hook portion may have one or more curved portions, one or more straight portions that extend at an angle relatively to an adjacent curved portion, or a combination of straight and curved portions to form a hook. In one embodiment, the hook may comprises two generally parallel portions with a curved or angled portion between the parallel portions to form the hook. This could increase the surface area of the narrow pinch point contacting the cheek, increasing stability on the face.

In order to avoid obstructing or clogging the inlet 107, a number of embodiments of the tip are envisaged, as will be described below. It should be appreciated that the conduit may comprise any suitable tip for receiving expired and/or exhaled gases.

In one embodiment, shown in FIGS. 4 to 6, the inlet 408 may have a mouth 407 that has a cross-sectional area that is greater than the adjacent portion of the body of the conduit. This interface is similar to the interface shown in FIG. 1 and like numbers are used to indicate like parts with the addition of 300 units (i.e., 103 vs. 403). The mouth 407 preferably has a shape that diverges outwardly from the lumen. Consequently, the tip of the inlet 408 has an exterior shape that diverges outwardly from the body 403. The mouth 407 may be frustoconical, pyramidal, flared, bell, or the like, in shape. Such a shape increases the opening area over which a liquid saliva meniscus may form. As a result, surface tension in the liquid saliva is reduced and is less likely to form an obstruction in the conduit.

In one embodiment, shown in FIG. 6, the tip 608 may have an alternating or varying depth, when viewed in cross-section. This interface is similar to the interface shown in FIG. 1 and like numbers are used to indicate like parts with the addition of 500 units. For example, when viewed in cross section, an undulating wave shape 607 or cut-outs may be apparent about the periphery of the tip. Such a shape disrupts the area over which a liquid saliva or other bodily fluid meniscus may form. As a result, the stability of the meniscus may be reduced and the possibility of a saliva obstruction in the conduit may also be reduced. Such a shape also prevents complete obstruction by internal tissues of the mouth (or nose). The tip shown and described in relation to FIG. 6 may be used with single or dual lumen conduit interfaces.

In another embodiment, shown in FIG. 7 for example, the conduit 701 may comprise multiple inlets/openings 723 about the periphery of the tip and/or along a distance of the conduit from the tip. This interface is similar to the interface shown in FIG. 1 and like numbers are used to indicate like parts with the addition of 600 units. In the event that one opening 723 is blocked, multiple openings 723 provide alternate entry points for receiving exhaled and/or expired gases. The multiple openings 723 may be substantially the same size or vary in size. The multiple openings 723 may be provided along a particular side, or there may be a greater distribution of openings 723 toward a particular side of the tip 708 than another. The shape of openings 723 may vary. The distribution, size and/or shape of openings 723 may vary in combination. FIG. 7 shows a portion of this alternative embodiment having diamond shaped openings. Liquids have a tendency to wick into corners. The diamond shaped openings will help to draw the saliva or other fluid such as blood from the centre of the occluded hole and also help to break the meniscus. FIG. 8 shows a portion of a similar embodiment. FIG. 8 has circular openings 823. It will be appreciated that the tip shown in FIG. 7 and the tip shown in FIG. 8 may be substantially straight as shown in those figures or may be curved following a spline as shown and described in relation to FIG. 3. The tip shown and described in relation to FIG. 7 may be used with single or dual lumen interfaces.

The diameter or width of the openings may be greater than the inner diameter of the gas lumen. This means that the resistance to flow of each of the openings is not greater than the resistance to flow of the gas lumen. So if only one opening is exposed, the respiratory gas monitor, such as an anesthesia machine will not have to draw against a greater resistance to flow which may cause a blockage and cause an alarm. Any suitable inlet/opening will be successful so long as the opening has the same or a greater pressure drop as the gas lumen itself (i.e. the same or less resistance to flow).

In one form, the inlets/openings 723, 823 only pierce the external wall of the gas lumen within the conduit so as to keep the wire fully enclosed within the wire conduit/support lumen of the conduit. The openings are preferably not located on the side of the conduit that contacts the inside of the patient's cheek to prevent the conduit sucking onto the cheek.

The openings may be located in a portion of the conduit that extends from the distal end of the conduit to the length of the conduit that marks the maximum insertion depth. This ensures that the openings only entrain air from inside the mouth and do not entrain any ambient air which may dilute the gas reading.

The openings may increase in size towards the end of the conduit. The opening size is chosen such that the resistance to flow through each opening is equal.

The tip of the interface may alternatively and/or additionally comprise a tip structure which further avoids the ingress of saliva or other bodily fluid that may be present, such as blood, as will be described below.

In another embodiment, the tip structure may comprise a filter, which at least partially surrounds the tip of the interface or which may be positioned inside the conduit at the distal end of the conduit, or which may positioned inside the tip. The filter may be substantially porous to allow exhaled and/or expired gases to pass through the filter and enter the tip of the interface. Additionally and/or alternatively, the filter may comprise openings (additional to the porous openings) to allow the passages of exhaled and/or expired gases. The filter may also absorb moisture, saliva or other bodily fluid that may be present, such as blood, preventing or at least substantially inhibiting an obstruction or blockage of the conduit. In one form, the filter may comprise a substantially absorbent porous sponge, foam or other suitably porous material. In another form, the filter may comprise a substantially hydrophobic material, such as a hydrophobic foam for example, that repels fluid/moisture while allowing expired or exhaled gases to pass through the filter and into the sampling tip. Suitable hydrophobic foams for use in such a filter include, but are not limited to, open-cell polyurethane foams (which may be of varying densities) with a hydrophobic coating, and microporous sintered polytetrafluoroethylene. Another suitable material for use as a hydrophobic filter is a hydrophobic textile, such as WrapPel, which is made from a 100% filament polyester that is coated in a hydrophobic fluorocarbon. Other possible materials for hydrophobic filters may be WrapPel and Gore-Tex. In one form, the filter may form the sampling tip, such that the sampling tip consists of a filter. In another form, the filter may substantially surround or partially surround the sampling tip. In yet another form, the filter may be placed inside the sampling tip or inside the sampling conduit to prevent fluid, such as moisture from expired or exhaled gases or bodily fluids entering the gas sampling conduit or from moving up the gas sampling conduit once the fluid has entered the conduit.

Alternatively or additionally, a filter to separate fluid from gas may be placed at any location along the length of the gas sampling conduit to help protect the respiratory gas monitor by preventing fluid from moving up along the sampling conduit and into the respiratory gas monitor.

In another embodiment, the tip structure may comprise a shield, cage, drum, or spacer that surrounds the tip of the interface. In use, the shield, cage, drum, or spacer abuts the interior cheek of the patient to displace the tip of the interface away from the interior cheek of the patient in order to reduce the likelihood of saliva or other bodily liquid reaching the exhaled and/or expired gas-receiving tip. The cage, drum, or spacer may be formed integrally with, or separately from, the conduit.

With reference to FIGS. 10 to 13, further examples of the conduit and gas sampling interface will now be described.

Figure 10:
FIG. 10 shows a spline representative of the series of curves applied to the conduit of an alternative embodiment of a gas sampling interface.
Figure 11:
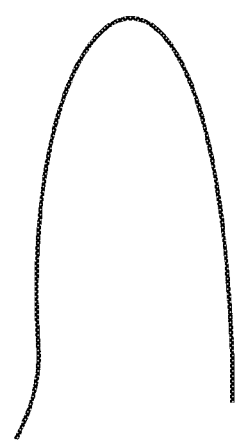
FIG. 11 shows a spline representative of the series of curves applied to the conduit of an alternative embodiment of a gas sampling interface.

FIG. 10 shows a spline for one example of a hook shape. The shape of the interface on the outside of the patient's cheek is preferably curved to follow the shape of the patient's cheek. This reduces the distance from the patient's face to the interface, reducing the torque and improving stability. The shape also reduces or eliminates the chance of the end of the interface poking into the patient's face, improving comfort. FIGS. 10 and 11 depict example splines or shapes. The lines shown are the centre line of any conduit cross section profile. The hook shape is a smooth curve to prevent kinks in the conduit, which can interfere with gas flow and may lead to blockages.

The insertion depth of the conduit into the patient's mouth or nose is selectable by the clinician. Typically, the insertion depth is greater than 10 mm, preferably greater than 20 mm. An insertion depth of 10 mm or less may allow the interface to roll out the patient's mouth, especially when the patient is sitting upright or semi-upright. The gap formed at the end of the hook (i.e. the space between the distal end of the conduit and the substantially straight portion of the body of the conduit) is preferably about 5 mm to provide a clamp onto the patient's cheek. A longer insertion depth also allows the conduit to extend beyond where the tip of the patient's tongue would naturally lie. This means the patient is less likely to block the end with their tongue, or push the interface out of their mouth. This could be a problem as the patient is unused to a foreign object in their mouth and may try to remove it with their tongue.

With reference to FIGS. 14 to 25, alternative embodiments of conduits having shields will now be described. As described above, the conduit may have several small inlets/openings or one larger inlet/opening 1427 near the tip of the conduit to provide alternative gas paths, if an inlet at the distal end of the conduit is blocked. The shields shown and described in relation to FIGS. 14 to 25 prevent or at least substantially inhibit the opening(s) from being blocked. The shield may have an extended portion that curves around the hook portion to prevent or at least substantially inhibit the outlet of the shield from being inserted into the mouth past the patient's lips. The shield may be non-circular to prevent or at least substantially inhibit the patient's cheeks from fully encapsulated and/or sealing around the shield. The shield may include cut outs to allow gases to enter. The shield may include one or more protrusions that prevent the patient's cheeks or lips sealing over the opening(s). The one or more protrusions allow saliva/blood to drain away from the tube opening(s). In one form, the shield may form a separate component that is attached to the conduit. Optionally, the shield may have a triangular shape. In one form, the shield may only partially cover the inlet(s)/opening(s) so that the shield does not fully cover the opening(s). In one form, the shield may cover only some inlets/openings of the conduit.

Figure 14:
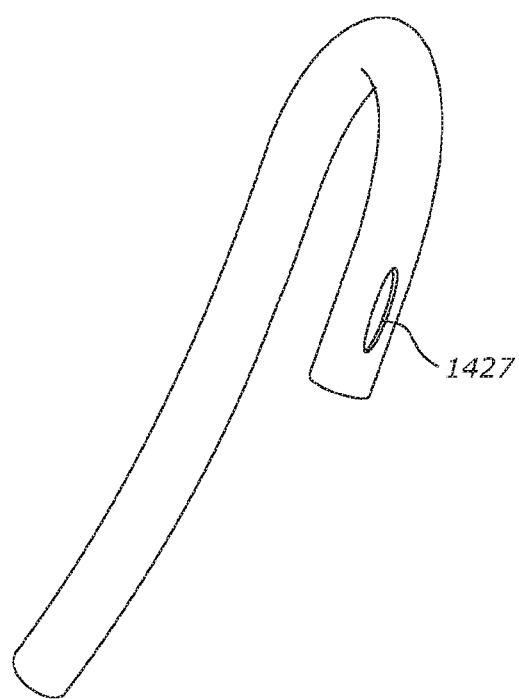
FIG. 14 shows an alternative embodiment of a gas sampling interface.
Figure 15:
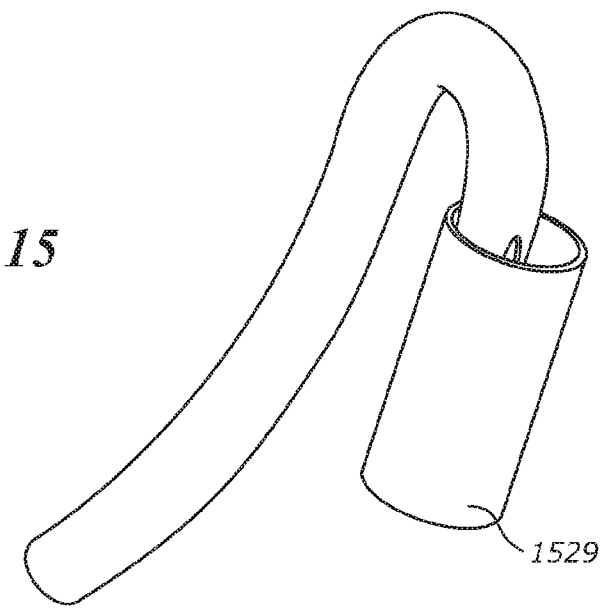
FIG. 15 shows an alternative embodiment of a gas sampling interface.

The inlet(s)/opening(s) of a conduit having multiple openings may be sized to provide a similar resistance to flow as a single inlet formed in the distal end of the conduit so that gas is drawn in evenly through the opening(s). The opening(s) may also be sized to minimise the maximum velocity through the conduit to reduce the risk of saliva or other bodily liquid that may be present, such as blood, being drawn into the conduit. For example, for a conduit comprising a single lumen having a 1.2 mm internal diameter, the elliptical hole may be 1 mm×5 mm. FIG. 14 shows an elliptical opening without a shield. FIG. 15 shows that embodiment with a shield.

FIG. 15 shows the gas sampling interface or conduit having a shield 1529 around the conduit to cover an opening in the conduit to prevent the opening from being partially or fully occluded. The shield of FIG. 15 is in the form of a substantially cylindrical component.

The shield may have a non-flat area to increase the surface area and angles over which the inside of the patient's cheeks has to seal to create a blockage.

Figure 16:
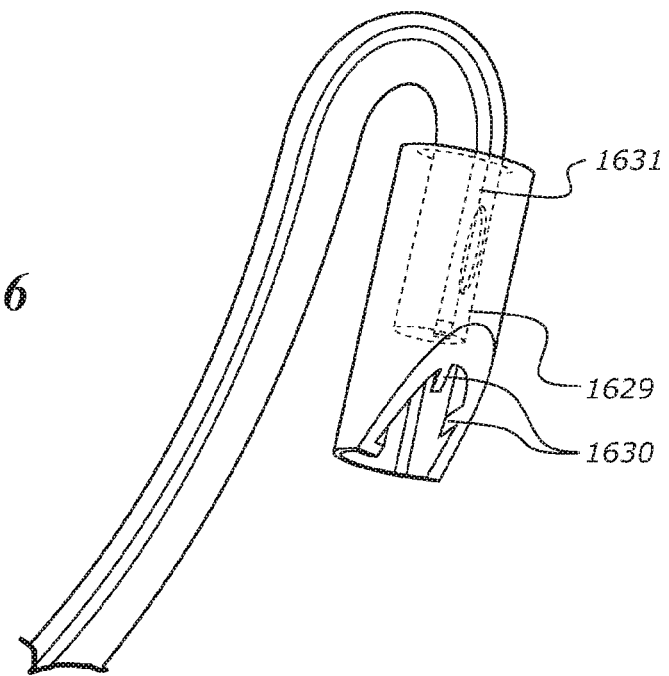
FIG. 16 shows an alternative embodiment of a gas sampling interface.

FIG. 16 shows a shield having internal ribs 1630 to space the shield 1629 away from the exterior of the conduit and the opening that is protected by the shield.

Figure 17:
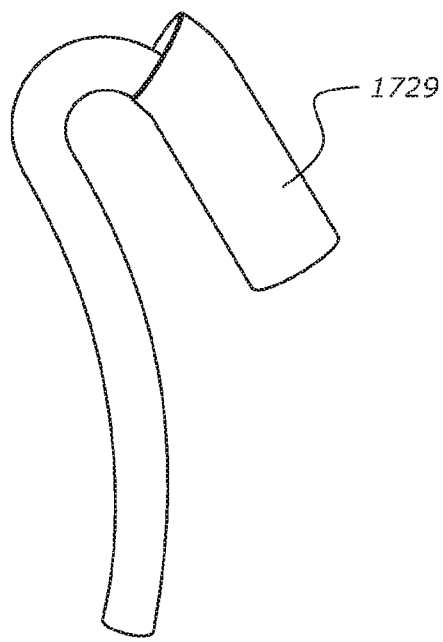
FIG. 17 shows an alternative embodiment of a gas sampling interface.
Figure 18:
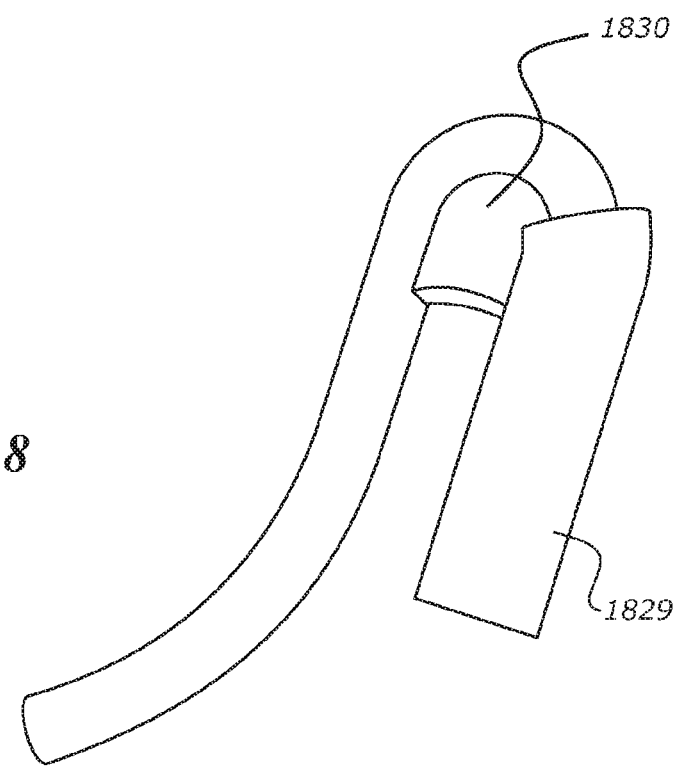
FIG. 18 shows an alternative embodiment of a gas sampling interface.

In one form, as shown in FIG. 17, the shield 1729 may extend past the patient's lips in use such that if the patient's lips seal around the interface, gas may still be entrained from the outside air, preventing partial or full occlusion and a subsequent machine alarm.

Alternatively, the conduit may comprise a barrier 1830 (shown in FIG. 18) located at the curved portion of the hook portion to prevent the distal end of the shield 1829 from being inserted into the patient's mouth past their lips or too deeply into the nare. In other words, the barrier may form a depth limit that prevents the gas sampling conduit from being inserted too deeply into a patient's mouth or nare.

The shield may be open down the full length of one side so that if the patient's lips are shut, gas from their mouth may still enter the gas sampling conduit through the opening.

Figure 19:
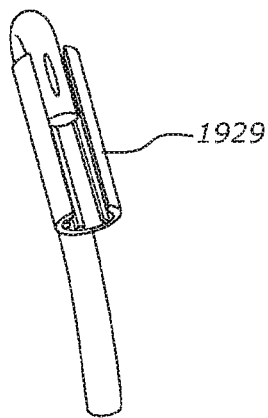
FIG. 19 shows an alternative embodiment of a gas sampling interface.

FIG. 19 shows a shield 1929 in the form of an elongate component having a generally C-shaped cross-section.

Figures 20, 21:
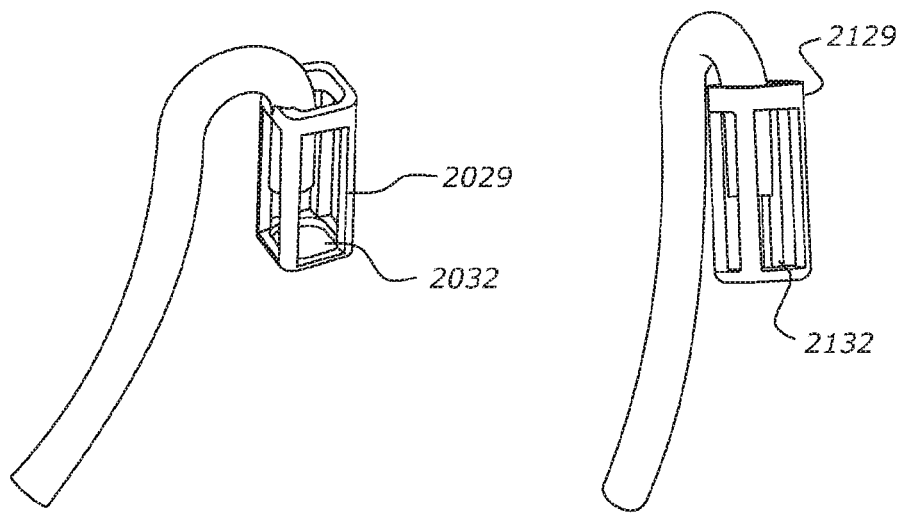
FIG. 20 shows an alternative embodiment of a gas sampling interface.
FIG. 21 shows an alternative embodiment of a gas sampling interface.

The shield may be non-circular to at least substantially inhibit the patient's cheeks from fully encapsulating and/or sealing around the shield. For example FIGS. 20 and 21 show square shields 2029/2129 having a generally square cross-section. The shields have cut-outs 2032/2132 or openings to allow gas to enter the sampling conduit through the shield when the patient's lips are shut.

Figure 22:
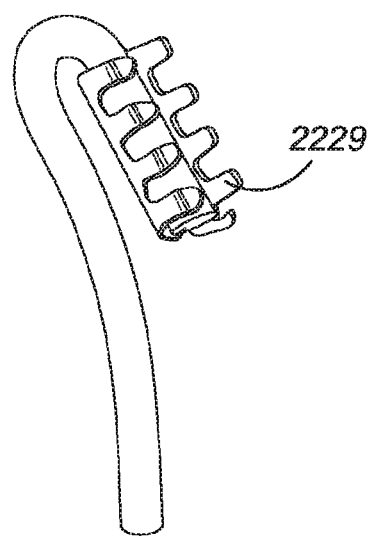
FIG. 22 shows an alternative embodiment of a gas sampling interface.
Figure 23:
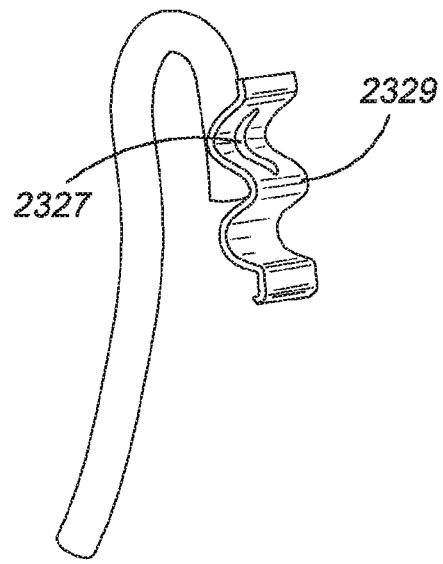
FIG. 23 shows an alternative embodiment of a gas sampling interface.

FIGS. 22 and 23 show forms of shields having protrusions that prevent the patient's cheeks or lips sealing over the gas sampling conduit inlet. FIG. 22 shows a shield having a number of protrusions in the form of prongs to form a castellated component 2229. FIG. 23 shows a shield comprising corrugated protrusions to form of a sinuous component 2329. Each arrangement of protrusions forms a shield that allows saliva and/or other bodily liquid that may be present, such as blood, to drain away from the conduit inlet, reducing the risk of the inlet becoming occluded.

A shield may be integral with the conduit or attached to the conduit as a separate component. Alternatively, a shield may be attached to, or fed through, a part of the conduit that extends out of the patients' mouth and attaches to the patient's mouth to reduce the risk of parts of the shield breaking off inside the patient's airway.

Figure 24:
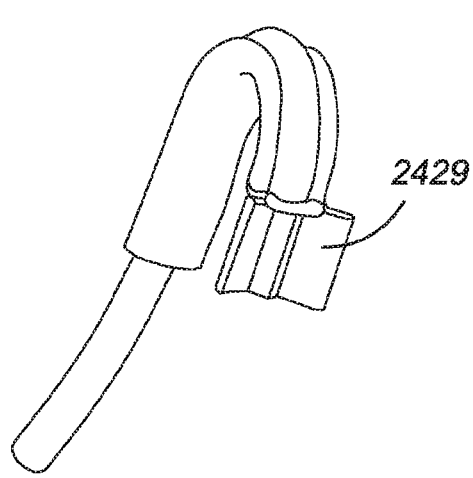
FIG. 24 shows an alternative embodiment of a gas sampling interface.
Figure 25:
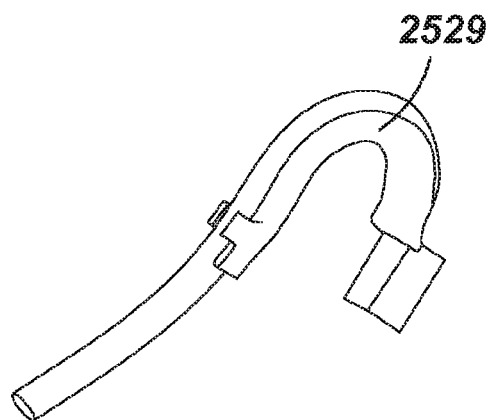
FIG. 25 shows an alternative embodiment of a gas sampling interface.

FIG. 24 shows an example of shield 2429 with alternative protrusions comprising outwardly extending arms that create a substantially triangular shape or V-shaped component around the conduit inlet. FIG. 25 shows a shield in the form of a planar component having arms that project from sides of the conduit.

In one form, the gas sampling interface may be attached to a breathing apparatus via an attachment member that may be a separate component that is attachable to both the breathing apparatus and the sampling interface, or an attachment member that forms part of (is integral with) the breathing apparatus, or an attachment member that forms part of (is integral with) the sampling interface.

The sampling interface may be attached to the breathing apparatus at any suitable location. For example, where the breathing apparatus is a nasal cannula, the sampling interface may be attached to a manifold of the cannula or to a strap of the headgear or to the breathing gas delivery tube. Where the breathing apparatus is a mask, the sampling interface may be attached to the frame of the mask, the seal of the mask or to a strap of the mask headgear or to the breathing gas delivery tube.

Figure 26:
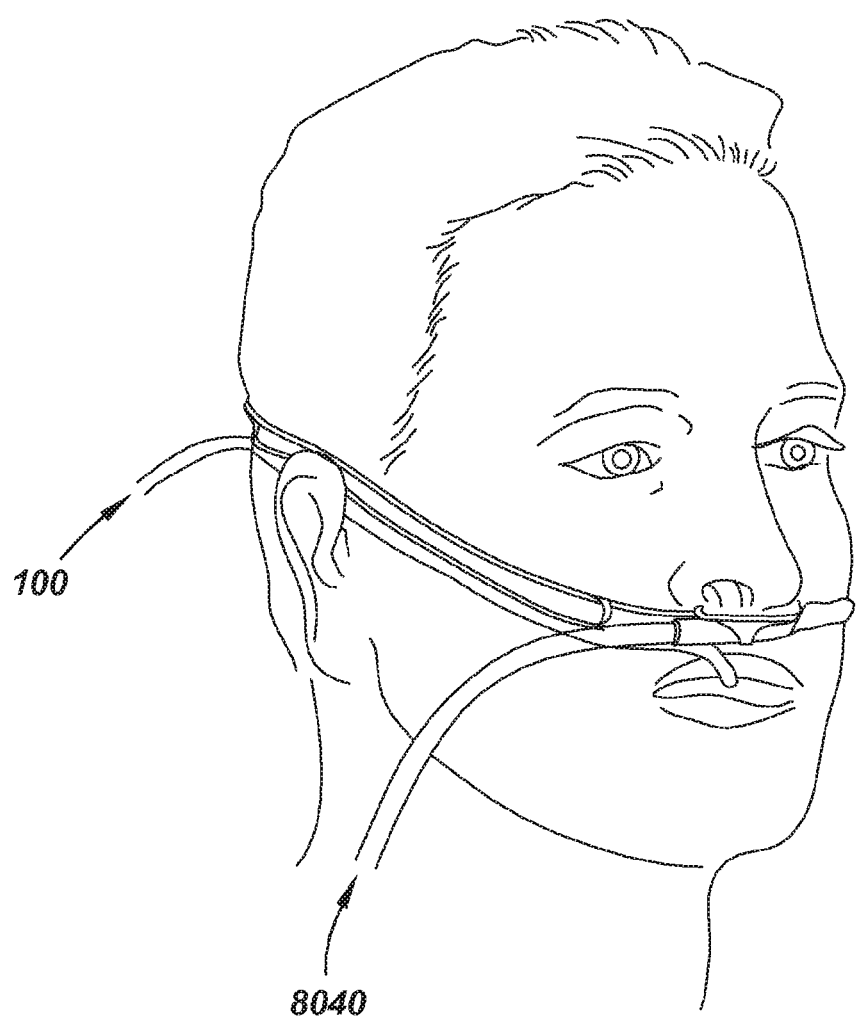
FIG. 26 shows an alternative embodiment of a gas sampling interface.

FIG. 26 shows one form of breathing apparatus comprising one form of gas sampling interface of the invention that is attached to or integral with the breathing apparatus. The breathing apparatus comprises a nasal cannula to which is attached a gas sampling interface. The nasal cannula comprises a manifold and at least one nasal prong or outlet extending from the manifold to be received in a user's nare. The nasal cannula also comprises an attachment member for securing a gas sampling conduit relative to the nasal cannula such that the inlet(s) of the gas sampling conduit receives gases exhaled and/or expired by the patient. In alternative embodiments, the breathing apparatus may comprise a different form of patient interface such as a mask, a nasal interface, or a full face mask, and an attachment member for securing a gas sampling conduit relative to the patient interface such that the inlet(s) of the conduit receives gases exhaled and/or expired by the patient. The breathing apparatus may provide high flow breathing gas to a patient.

The attachment member may comprise any suitable attachment system to attach the gas sampling conduit to a nasal cannula or other form of patient interface. For example, the attachment member may comprise a clip, a pair of clips, or a band. The attachment member may comprise an elastomeric material.

Where the patient interface is a nasal cannula, the attachment member may be integral with the manifold of the cannula and/or at least one nasal prong or outlet. Alternatively, the attachment member may be a separate component that is attachable to the manifold and/or at least one nasal prong or outlet or to another suitable portion of the breathing apparatus, such as the breathing gas delivery tube.

FIGS. 27 to 34 show various embodiments of attachment members that are configured to attach a conduit of a breath sampling interface 100 to a manifold of a cannula or headgear strap of a breathing apparatus (both being indicated in FIGS. 28, 30, 32, and 34 by 4000).

Figure 35:
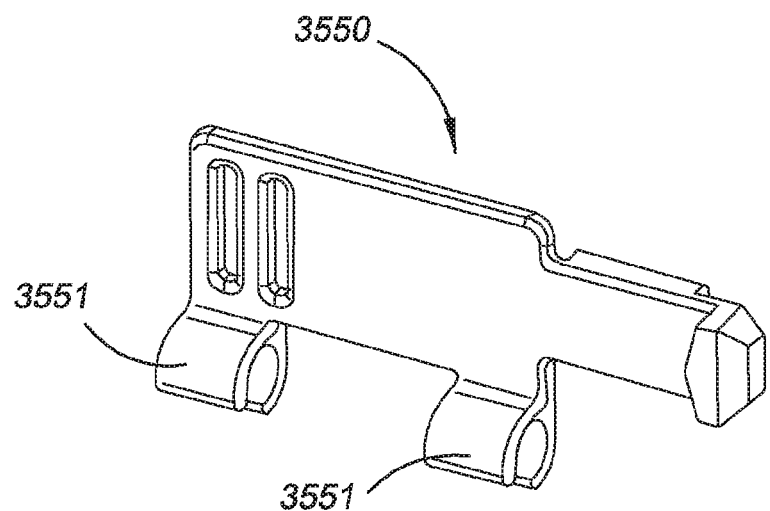
FIG. 35 shows a connector of a gas sampling interface.

The position of the gas sampling conduit may be adjustable relative to the attachment member. For example, FIG. 35 shows an attachment member/connector for a patient interface in which the attachment member comprises a headgear clip 3550 that comprises a clip 3551 suitable for securing a conduit to a breathing apparatus, such as a nasal cannula. The headgear clip connects a headgear strap to the side arms of the nasal cannula. A side arm of the nasal cannula includes complementary clip receivers.

Figure 36:
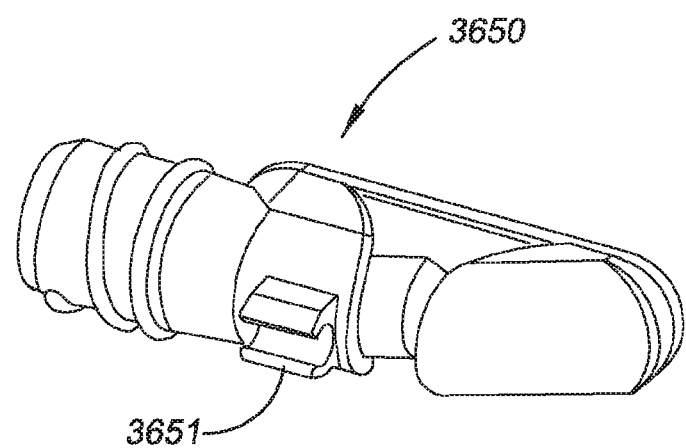
FIG. 36 shows a connector of a gas sampling interface.

FIG. 36 shows another form of attachment member/connector for a nasal cannula. The connector in the form of a manifold section 3650 that is insertable into the nasal cannula. The manifold section is connected to a gases supply tube at a threaded end. The opposing end is inserted into a complementary aperture in a nasal cannula to supply gases to the prongs of the nasal cannula. The manifold section includes clips 3651 for securing a gas sampling conduit.

Figure 37:
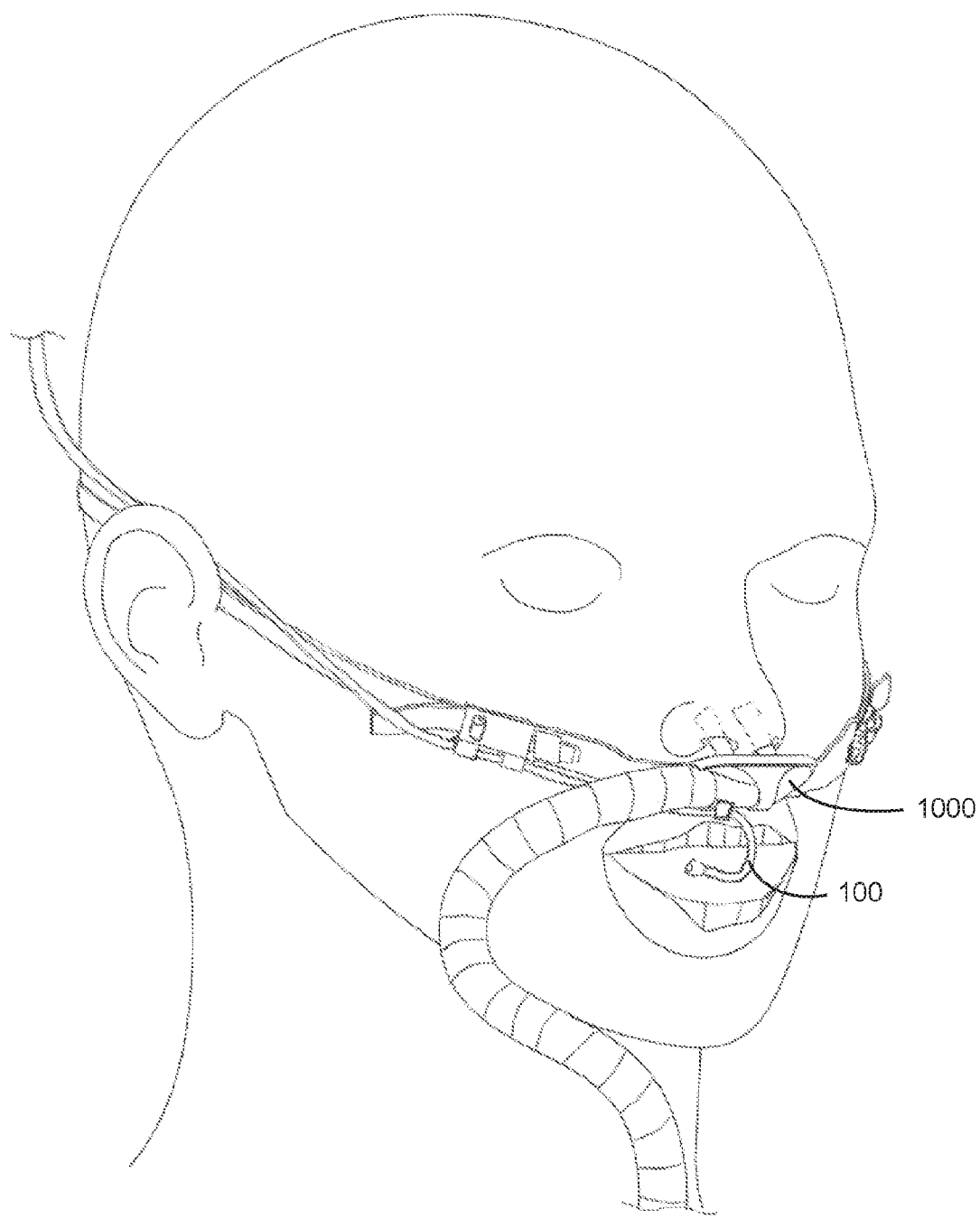
FIG. 37 shows an alternative embodiment of a gas sampling interface including the connector of FIG. 35 and the connector of FIG. 36.

FIG. 37 shows a breathing apparatus incorporating the connectors/attachment members of FIGS. 35 and 36 connected to the nasal cannula and also shows the relative position of the breathing apparatus on a patient's face. A gas sampling conduit is attached to the cannula with clips similar to those in FIGS. 35 and 36.

A breathing apparatus incorporating either or both of the connectors/attachment members of FIGS. 35 and 36 allows the retention method by which the gas sampling conduit is attached to the breathing apparatus to be independent of the patient's face shape and/or size.

The gas sampling conduit is typically held in place slightly in or near the patient's mouth, or just inside or near one of the patient's nares, to reduce the chance of a blockage occurring from fluid being sucked into the conduit or from the conduit suctioning onto the patient, such as onto the patient's cheek or lip. Positioning the conduit in this way is less invasive and less obstructive than known sampling systems that require the inlet of the gas sampling interface to be positioned at the rear of a patient's mouth. By positioning the conduit just inside the oral or nasal cavity or proximate to the oral or nasal cavity, it is possible to reduce the risk of the sampling conduit creating pressure points or agitation to the patient.

In one form, the gas sampling interface or conduit may be integral with the cannula and moulded or extruded to create one part having two gas lumens; one gas lumen being in fluid communication with a respiratory gas monitor and one gas lumen/tube being in fluid communication with the gas flow source of the cannula. For example, the gas sampling interface or conduit may be partially co-extruded or co-moulded alongside the gas delivery tube of the cannula.

In one form, the gas sampling conduit may be clipped onto a breathing apparatus, such as a nasal cannula. The sampling conduit may be clipped onto the cannula during manufacturing, or by the end user to give flexibility of use. In one form, only one clip may be used to attach the sampling conduit. Alternatively, multiple clips may be used across at least a portion of the length of the cannula to give additional stability and positioning control of the sampling conduit in relation to the cannula. The clips could be placed on one side of the patient's face to leave the other side of the face free of equipment. Alternatively, the clips could be placed on either side of the nasal prongs of the cannula.

In one form, the nasal cannula and gas sampling conduit may be configured to connect the gas sampling conduit to a gas sampling tube of a respiratory gas monitor and to connect the cannula to a gas delivery source simultaneously and with a single connection comprising two connectors and/or with a single connecting motion.

As described above, the sampling conduit may be a single lumen conduit. Alternatively, the sampling conduit may be a double lumen conduit having a wire located within at least one of the lumens to provide for positional control of the sampling conduit so that the conduit can be selectively positioned at or near the patient's mouth or one of the nares of the patient's nose.

Figure 27:
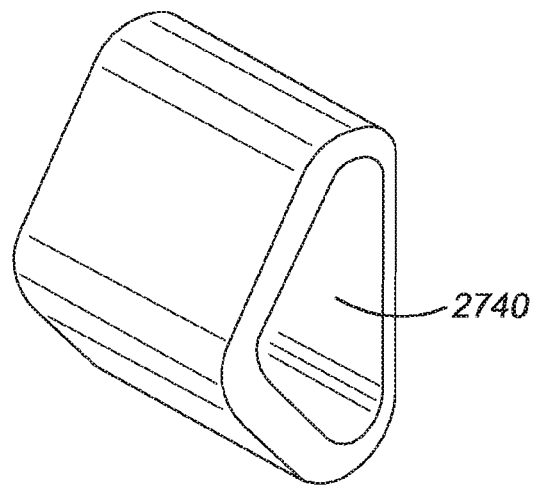
FIG. 27 shows an embodiment of an attachment member of gas sampling interface.
Figure 28:
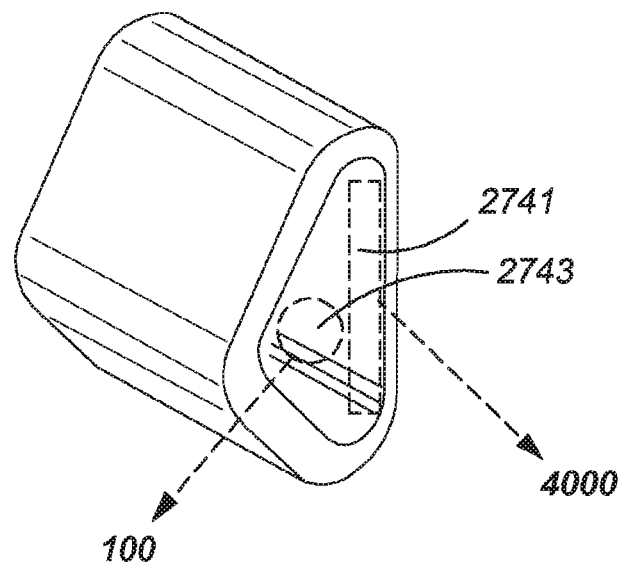
FIG. 28 shows the attachment member of FIG. 27 with details of the relative position of a cannula and a gas sampling conduit.

Other forms of attachment members may be used to attach a gas sampling conduit to a breathing apparatus. For example, FIGS. 27 and 28 show one embodiment of an attachment member in the form of a band or loop 2740. The band or loop may comprise an elastic or elastomeric material such as TPE or silicone. The band or loop 2740 may stretch and slide over the cannula and gas sampling conduit. The position of the cannula is indicated by 2741 and the position of the gas sampling conduit is indicated by 2743. The cannula side of the band 2740 may have a thinner wall section (e.g. 0.5-1 mm) to ensure it is low profile on the patient's face and has sufficient stretch. The conduit side of the band 2740 may have a thicker wall section (e.g. 1.5 mm-2 mm) to ensure the conduit doesn't adhere to the band when it is pulled through and/or repositioned and ensures the clip doesn't move with the conduit. The cross section of the band may be circular, triangular or irregular, and/or dependent on the cannula cross section.

FIGS. 29 to 34 show embodiments of attachment members in the form of clips 2940, 3140, and 3340 that can slide over the cannula. The position of the cannula is indicated by

Figure 29:
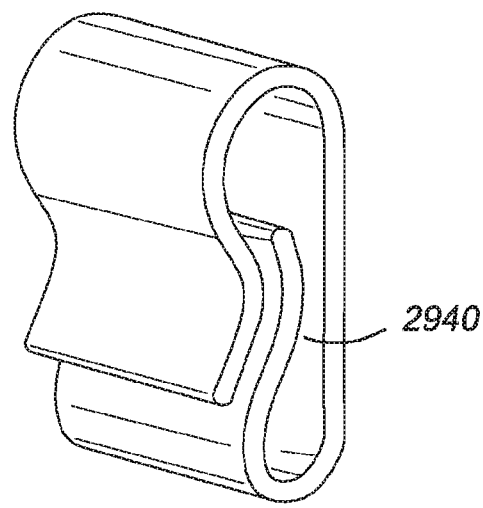
FIG. 29 shows an alternative embodiment of an attachment member of gas sampling interface.
Figure 30:
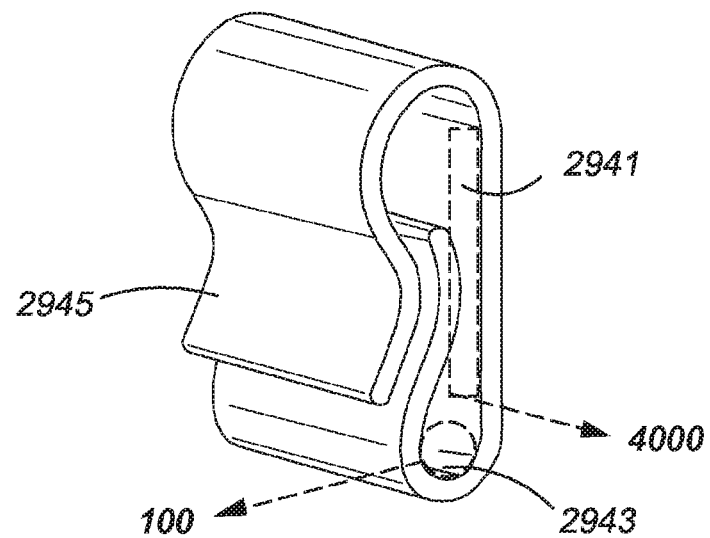
FIG. 30 shows the attachment member of FIG. 29 with details of the relative position of a cannula and a gas sampling conduit.
Figure 31:
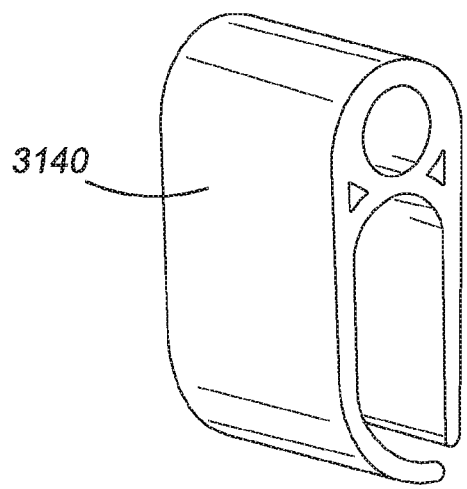
FIG. 31 shows an alternative embodiment of an attachment member of gas sampling interface.
Figure 32:
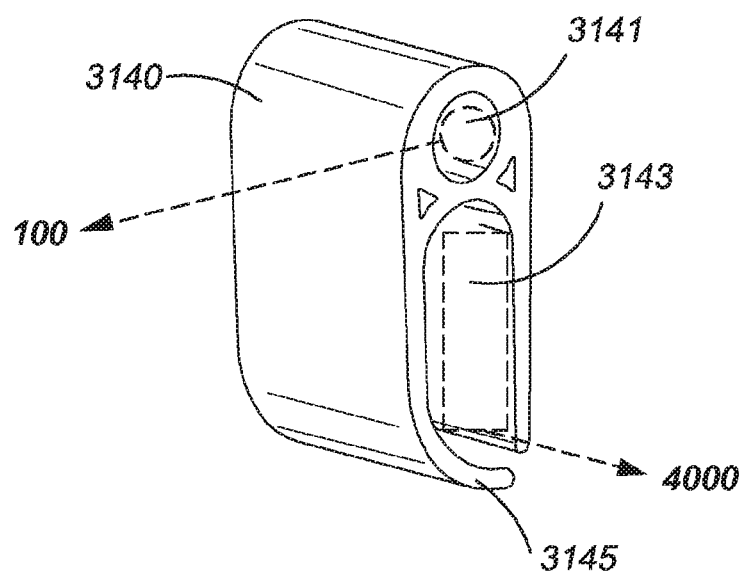
FIG. 32 shows the attachment member of FIG. 31 with details of the relative position of a cannula and a gas sampling conduit.
Figure 33:
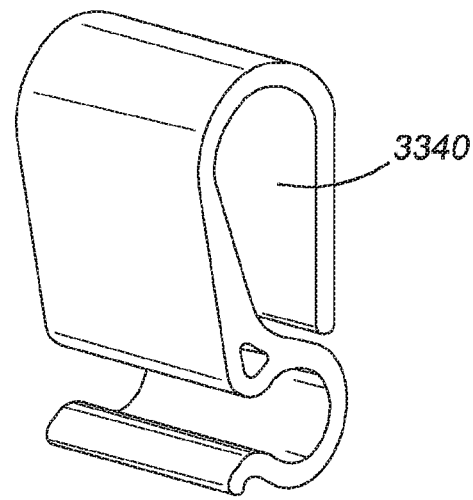
FIG. 33 shows an alternative embodiment of an attachment member of gas sampling interface.
Figure 34:
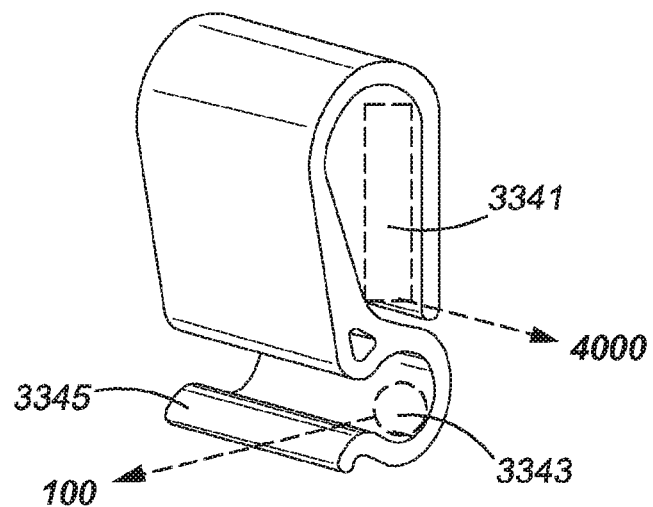
FIG. 34 shows the attachment member of FIG. 33 with details of the relative position of a cannula and a gas sampling conduit.

2941/3141/3341 and the position of the gas sampling conduit is indicated by 2943/3143/3343. FIGS. 29 and 30 show a clip with an overlapping portion 2945. FIGS. 31 to 34 show a clip with a tongue 3145/3340/3341 extending from a body of the clip to provide a space for inserting and holding the cannula therein. The tongue may flex or bend to allow that insertion. The clips of FIGS. 33 and 34 also show a curved tongue 3345 that provides a space for inserting the gas sampling conduit and holding the conduit therein. Each tongue may flex or bend to allow that insertion. For example, the gap between the tongue and the body of the clip may be smaller than the external diameter of the gas sampling conduit or portion of the cannula that is to be attached to the clip, as the case may be. In this arrangement, the flexible nature of the tongue allows the cannula or conduit to be pushed into the gap, causing the tongue to move away from the clip body to allow the cannula or conduit to be located between the clip body and the tongue. Once the cannula or conduit is in position within the clip, the pressure on the tongue may be removed so that the tongue returns to its natural rest position and the cannula or conduit is unable to be removed from the clip without sufficient force to force the tongue away from the clip body again. The tongue may be biased toward the clip body. In some forms, the gap between the tongue and clip body may be slightly smaller than the portion of the cannula held by the clip or smaller than the external diameter of the conduit so that the cannula or conduit is gently clamped between the tongue and clip body. These embodiments may comprise a polymeric material such as polypropylene. In one form, the clip may have a cross section with a break in it that allows space for the cannula to be passed through. The clip may have a separate section that secures the gas sampling conduit and that could be a clip, such as a partial cylinder or cylinder. The cross section design may be dependent on the cannula cross section.

In one embodiment, the gas sampling interface comprises a hook for engaging with part of a patient's face and an attachment system for securing a gas sampling conduit relative to the hook such that an inlet of the conduit receives gases exhaled and/or expired by the patient. The hook may be inserted into a nare of the patient or into the mouth of the patient. For example, the hook may be inserted into the corner of a patient's mouth. The hook provides a system by which to attach the conduit to the patient to locate the conduit in the vicinity of the mouth or nose.

The hook may be rigid. Alternatively, the hook may be flexible. In a further alternative, the hook may be a combination of rigid and flexible materials or features. The rigid or flexible hook may be a moulded polymeric material.

The hook may comprise any suitable attachment system comprising at least one attachment member, such as a channel, a clip, a pair of clips, or a band, for example, to secure a gas sampling conduit to the hook. The attachment member may comprise an elastomeric material.

The attachment member may be integral with the hook or a separate component to the hook. The position of the gas sampling conduit may be adjustable relative to the hook.

The following alternative embodiments of the gas sampling interface comprise a rigid hook, which may be supplied in varying sizes based on patient anthropometric considerations.

Figure 38:
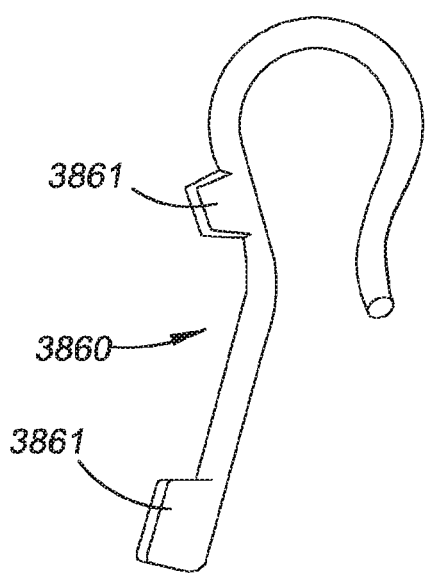
FIG. 38 shows a side view of an alternative embodiment of a hook of a gas sampling interface.

With reference to the embodiment shown in FIG. 38, the gas sampling interface comprises a rigid hook 3860 for supporting a gas sampling conduit. FIG. 38 shows one embodiment of a hook having a narrow region. The hook has a shape similar to the shape of the spline shown and described in relation to FIG. 3. The narrow region advantageously provides some compression of a patient's cheek to secure the hook in position. In the embodiment of FIG. 38, the narrow region is about 8 mm.

A radius at the end of the hook defines a minimum radius of curvature of the gas sampling conduit, thereby preventing kinking of the conduit, and providing clearance around the thicker region of the patient's cheek near their mouth (facial modiolus).

An angled or curved section is provided at the outside of mouth where the hook shapes away from the cheek to allow easy hook attachment and removal.

The following embodiments of the gas sampling interface incorporate a gas sampling conduit that includes a flexible resilient support structure, such as a wire. The wire may be a metal wire or a rod either positioned in a lumen of the gas sampling conduit, integrated into the material (over-moulded or co-moulded) of the gas sampling conduit or otherwise adhered or bonded to outside of the gas sampling conduit. This allows for positional adjustment of the free end of the conduit. Alternatively, the hook may be semi-rigid, but still malleable, such that a wire is not required.

In some forms, the gas sampling conduit may be slid along the hook to vary the length of the free end of the conduit that may extend beyond the free end of the hook. In another form, the conduit may be attached to the hook so that the free end portion of the conduit is at the desired length. When combined with the ability to move the gas sampling conduit relative to the hook, the gas sampling conduit end position is limited only by the length of the conduit tubing, the length of wire within the conduit, and physical constraints imposed by the patient or necessary surgical or procedural equipment.

FIGS. 38 to 46 show embodiments of rigid and semi-rigid hooks with different features and/or methods of attaching a gas sampling conduit to a rigid or semi-rigid hook.

Figure 39:
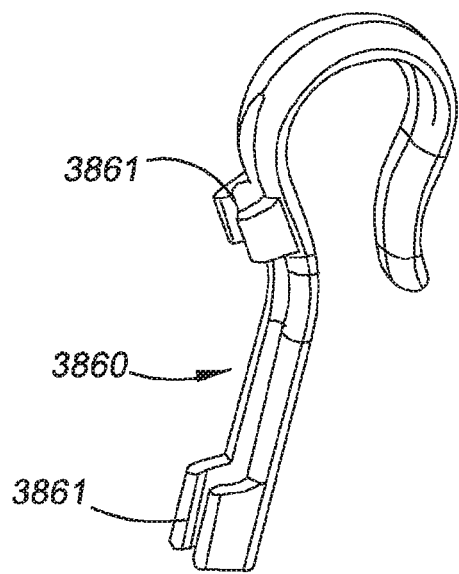
FIG. 39 shows a perspective view of the hook of FIG. 38.
Figure 40:
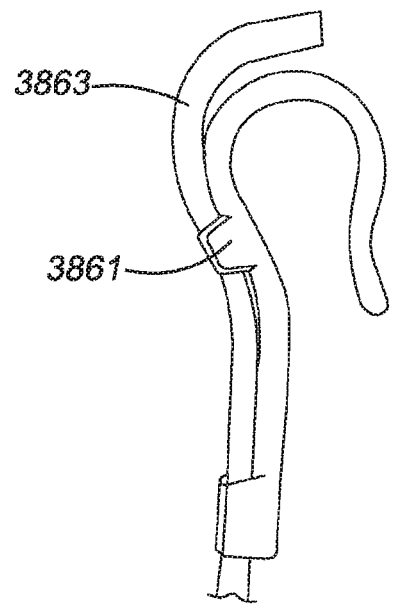
FIG. 40 shows a side view of the gas sampling interface of FIG. 38 together with a gas sampling conduit.

The embodiment shown in FIGS. 38 to 40 includes attachment members comprising integral clips 3861 on the outside of the rigid hook. The clips 3861 allow the sampling conduit 3863 to be pressed into the clips either through flexing the clips or flexing of the gas sampling conduit or both. The clips also allow the sampling conduit to be pulled or pushed axially through the clip to adjust the length of the free end portion of the gas sampling conduit. Once adjusted, the clips retain the sampling conduit in position relative to the hook.

Figure 41:
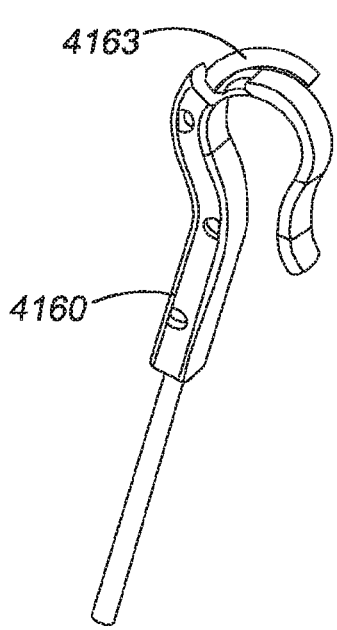
FIG. 41 shows a perspective view from one side of an alternative embodiment of a gas sampling interface.
Figure 42:
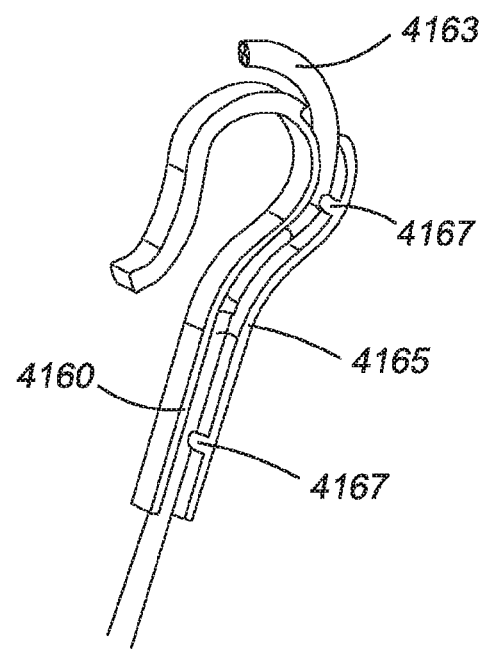
FIG. 42 shows a perspective view from another side of the gas sampling interface of FIG. 41.

FIGS. 41 and 42 show a hook having a conduit attachment system with attachment members comprising clips 4167 integral with an internal channel 4165 of a hook 4160. This embodiment allows the gas sampling conduit 4163 to be pressed into the clips either through flexing the clip or flexing of the gas sampling conduit. This embodiment also allows the gas sampling conduit 4163 to be pulled or pushed axially through the clips 4167 and channel 4165 so the tube free length can be adjusted. Further, this embodiment retains the gas sampling conduit 4163 in a secure position relative to the hook 4160.

Figure 43:
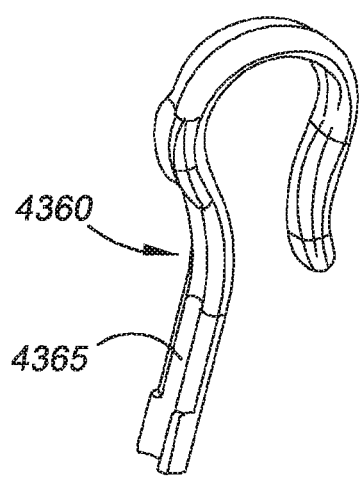
FIG. 43 shows a perspective view of an alternative embodiment of a hook of a gas sampling interface.

FIG. 43 shows a perspective view of an alternative embodiment of a rigid hook of a gas sampling interface 4360. This embodiment incorporates rigid end stops for the location and restraint of a flexible component for attaching the sampling tube to the rigid hook.

Figure 44:
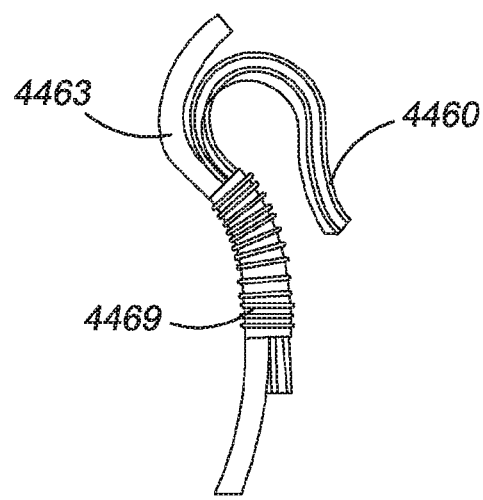
FIG. 44 shows an alternative embodiment of a gas sampling interface, incorporating the rigid hook of FIG. 43.

FIG. 44 shows an embodiment having the rigid hook of FIG. 43 and a flexible component 4469 that forms a sleeve, which is used to hold the gas sampling conduit 4463 while allowing the length of the free end portion of the gas sampling conduit to be adjusted. The sleeve may be ribbed to provide additional grip on the outside of the patient's cheek.

Figure 45:
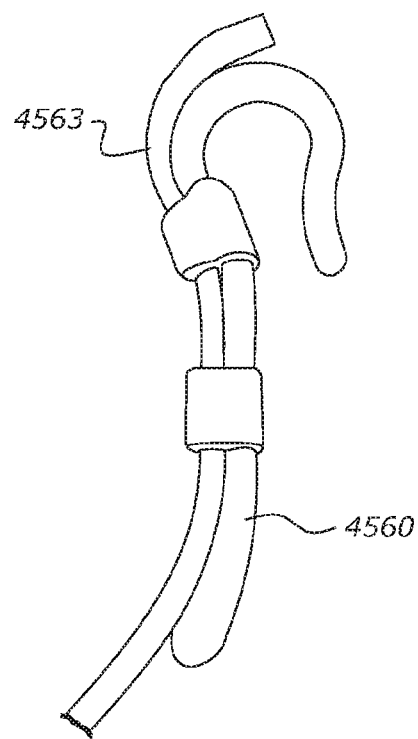
FIG. 45 shows a side view of an alternative embodiment of a gas sampling interface.
Figure 46:
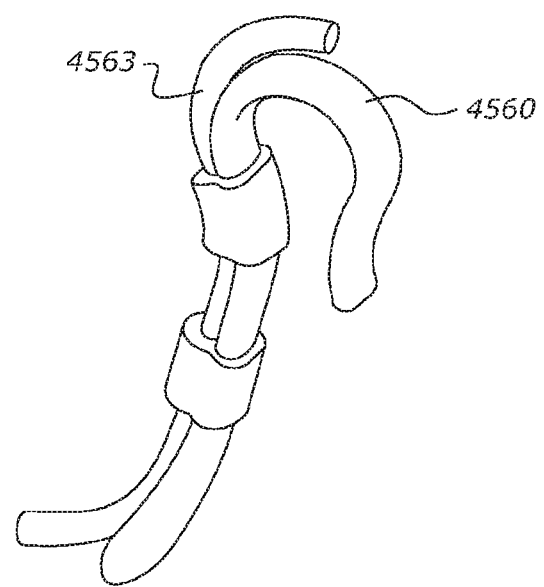
FIG. 46 shows a perspective view of the gas sampling interface of FIG. 45.

FIGS. 45 and 46 show embodiments of hooks having attachment systems that have been over-moulded over the hook. These embodiments includes a rigid polymer hook 4560 and one or more over-moulded sleeves that each form an attachment member. A gas sampling conduit is threaded through the sleeve(s) to attach the gas sampling conduit 4563 to the hook. The length of the free end portion of the gas sampling conduit may be adjusted by pulling the conduit through the sleeve/over-mould material until a desired length extends beyond the sleeve. That is the sleeves/over-mould sections or components are fixed to the rigid hook with a mechanical and/or chemical lock, but are not fixed to the gas sampling conduit. These embodiments may incorporate bend relief and other features such as a soft grip handle.

As mentioned above, the hook may be flexible. The flexible pre-formed hook is inserted into the corner of a patient's mouth and provides an attachment for fixing the gas sampling conduit in the vicinity of the patient's mouth or nose. One advantage of the flexible hook is that the hook shape can be modified, for example by flexing, to fit the size of patient's mouth.

Figure 47:
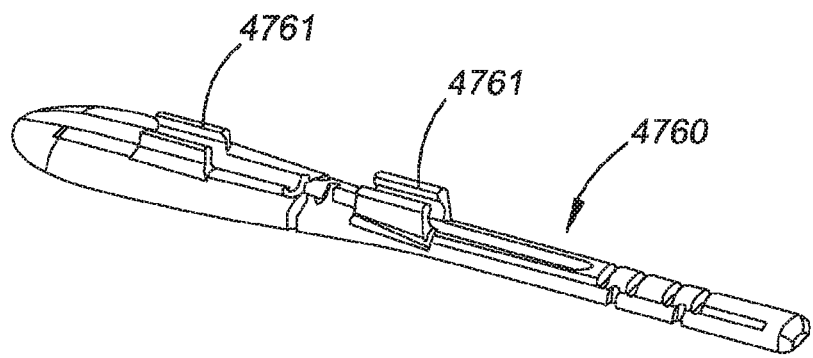
FIG. 47 shows an alternative embodiment of a hook of a gas sampling interface in a before-use configuration.
Figure 48:
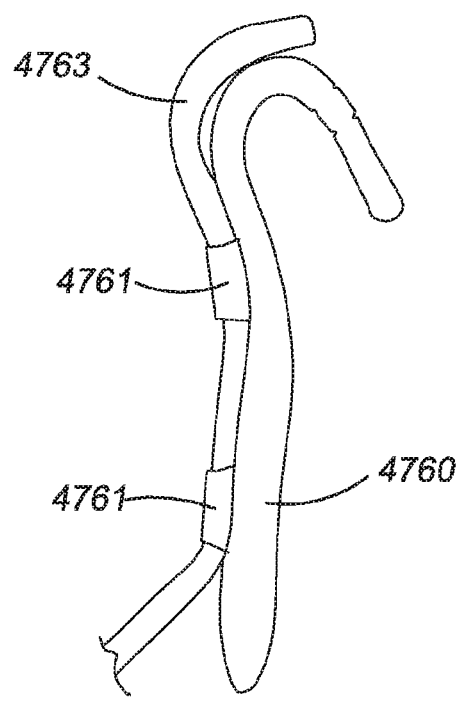
FIG. 48 shows the hook of FIG. 47 in an in-use configuration together with a gas sampling conduit.

The embodiment shown in FIGS. 47 and 48 incorporates a wire in the form of a flexible wire, rod or strip (metallic or polymer) that is over-moulded or co-moulded (in a flat position) with a suitable flexible polymer, such as TPE or silicone, and then shaped into a hook prior to dispatch to customers. This embodiment includes attachment members comprising clips 4761 for external attachment of a gas sampling conduit 4763. In this embodiment, the over-mould material is bonded to a wire such as an internal flexible wire, rod or strip (metallic or polymer) to allow the hook size and shape to be easily modified to fit individual patients. The over-mould design includes one or more attachment members (clips) for attaching to a gas sampling conduit. The over-mould design may include features for bend relief at suitable locations to enable bending of the over-moulded wire into a hook shape. In this embodiment, there may be bend relief features in the mould tooling for location of the wire. The hook may be pre-formed prior to dispatch.

With reference to FIGS. 49 to 53, alternative embodiments of attachment members having dual flexible tubes or sleeves are shown for attaching to two tubular members. The tubular members may comprise a gas delivery conduit and a gas sampling conduit, or the tubes may comprise a gas sampling lumen and a support lumen, or the tubes may comprise a pair of gas sampling lumens, for example. In these embodiments, the gas sampling interface may incorporate a gas sampling conduit with a wire, such as a metal wire or rod or strip located within a wire lumen, integrated into the tubing material (such as by being over-moulded or co-moulded) of the conduit or adhered or bonded to the outside of the conduit. The gas sampling conduit is preferably formed into a hook shape for attachment to patient's mouth. These embodiments also incorporate a gas sampling conduit with a wire such as a metal wire or rod or strip located within one of two or more lumens within the gas sampling conduit. The wire may be integrated into the tubing material of the conduit (such as by being over-moulded or co-moulded) or adhered or bonded to the outside of the tubing to allow for positional adjustment of the conduit by providing the conduit with a semi-flexible and resilient end portion that can be bent to a desired shape to engage with a patient's mouth or nare during gas sampling.

Figure 49:
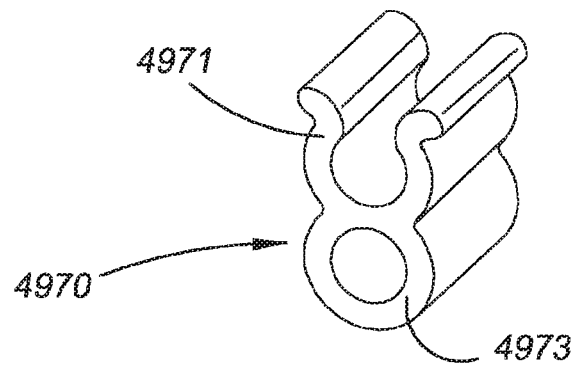
FIG. 49 shows an embodiment of a clip for a gas sampling interface.
Figure 50:
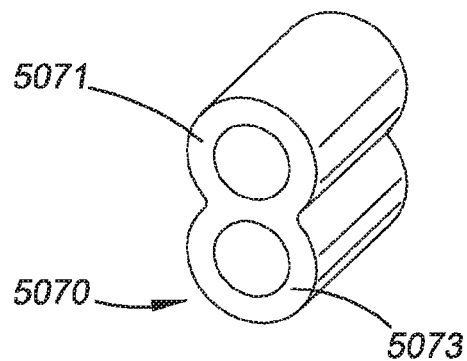
FIG. 50 shows an alternative embodiment of a clip for a gas sampling interface.
Figure 51:
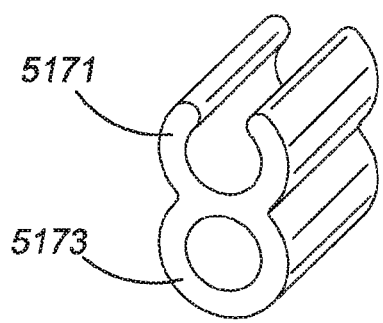
FIG. 51 shows an alternative embodiment of a clip for a gas sampling interface.

Attachment of two conduits could be via one or more attachment members comprising clips with limited or no movement relative to the hooked conduit (4973/5073/5173) while allowing the sampling conduit to be moved axially through the clip (4971/5071/5171) so that the free length of the conduit can be adjusted. Multiple clips may be required. FIGS. 49 to 51 show various embodiments of clips 4970/5070/5170. The clips may be moulded or extruded components. FIG. 52 shows a gas sampling conduit 5263 attached by clips 5270 to a hook 5260.

FIG. 53 shows a clip 5270 that is moulded around a pair of lumens of a dual lumen conduit. The clip 5270 may be over-moulded over the lumens and or co-moulded with the lumens. This form of clip holds the lumens substantially equidistant from each other, but also allows the lumens of the conduit to be pulled or pushed axially through the over-moulded or co-moulded material of the clip so that the free length of the conduit can be adjusted. Multiple over-moulded or co-moulded clips may be used along the length of the conduit.

FIG. 54 shows a cross section of a zip-cord conduit where a first cord is for gas sampling and a second cord is configured to be formed into a hook shape. The cords of the conduit can be unzipped and cut so that the second zip cord may be shaped to form a hook that is substantially shorter than the first zip cord that is used for gas sampling. The gas sampling cord may also be formed into a suitable hook shape to best sample expired or exhaled gas from a patient. FIG. 54 shows a gas sampling conduit comprising a first zip cord comprising a gas sampling lumen 5481 and a wire lumen 5483, and a second zip cord having a second wire lumen 5485 for forming into a hook shape.

Figure 55:
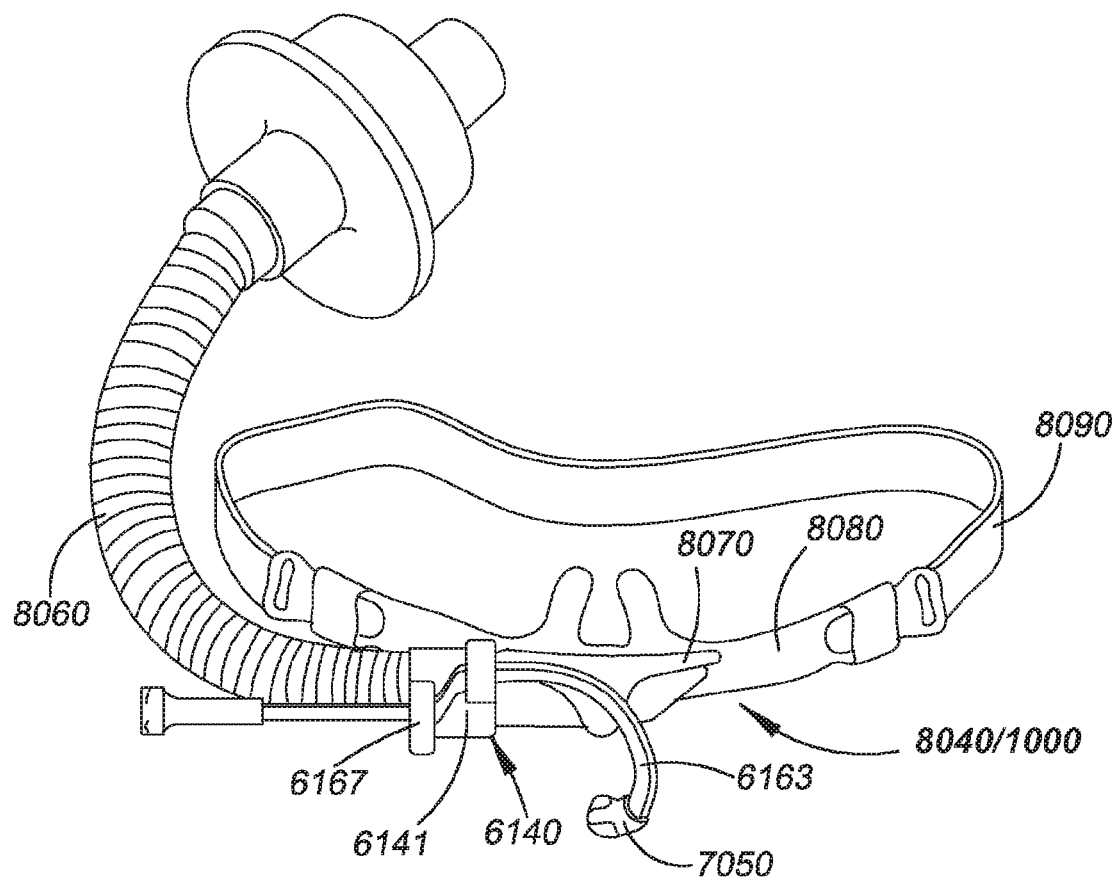
FIG. 55 shows a schematic drawing of another embodiment of a gas sampling interface attached to a nasal cannula.

In one embodiment, as shown in FIG. 55, a gas sampling interface comprises a gas sampling conduit 6163 and an attachment member 6140, for securing the gas sampling conduit to a breathing apparatus 1000 that delivers breathing gas to a patient, such as a mask or nasal cannula 8040. In one form, the gas sampling conduit is removably attached to the attachment member. The attachment member may be configured to be removably attachable to the breathing apparatus or the attachment member may be integral with (form part of) the breathing apparatus. For example, the attachment member may be built into the design of a nasal cannula, mask or other breathing apparatus to removably attach the gas sampling conduit to the breathing apparatus.

Figure 56:
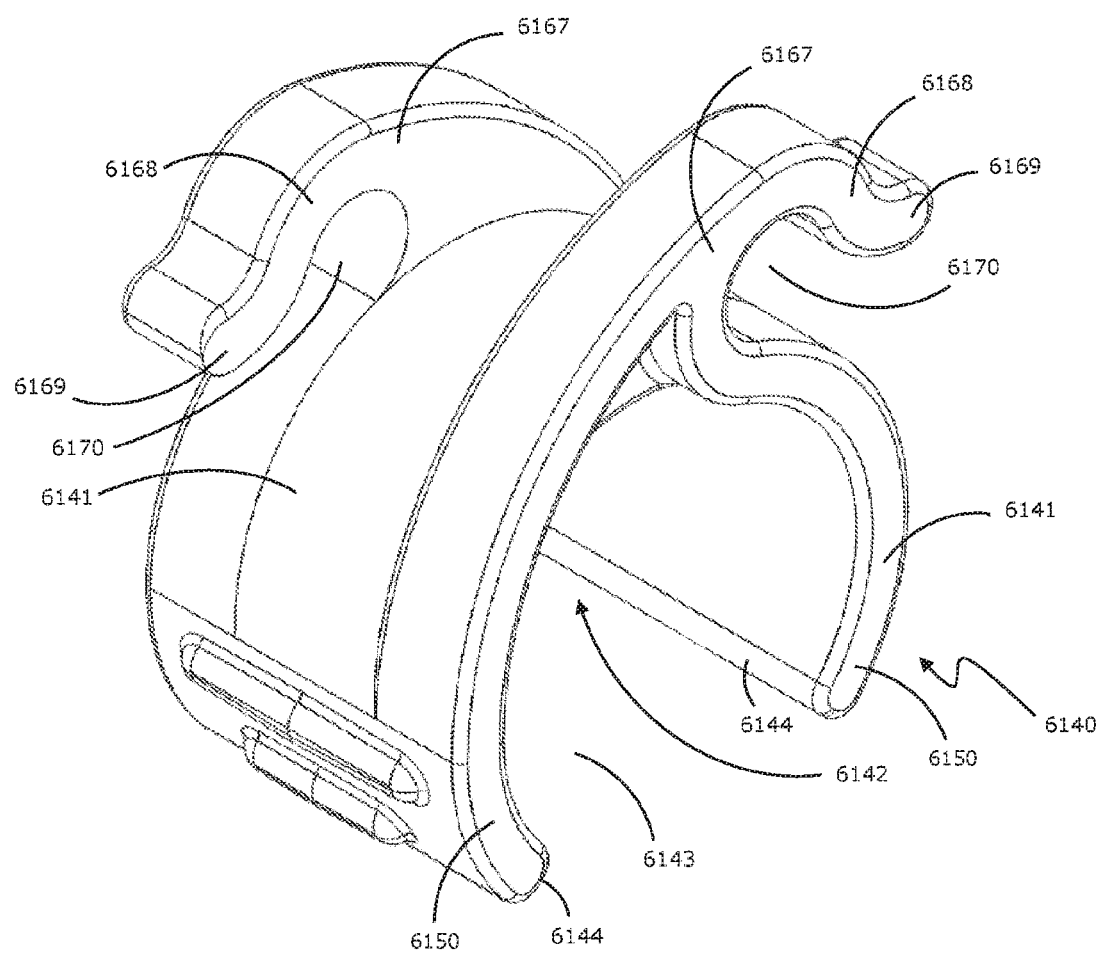
FIG. 56 shows a perspective view of one form of attachment member for attaching a gas sampling conduit to a breathing apparatus.
Figure 57:
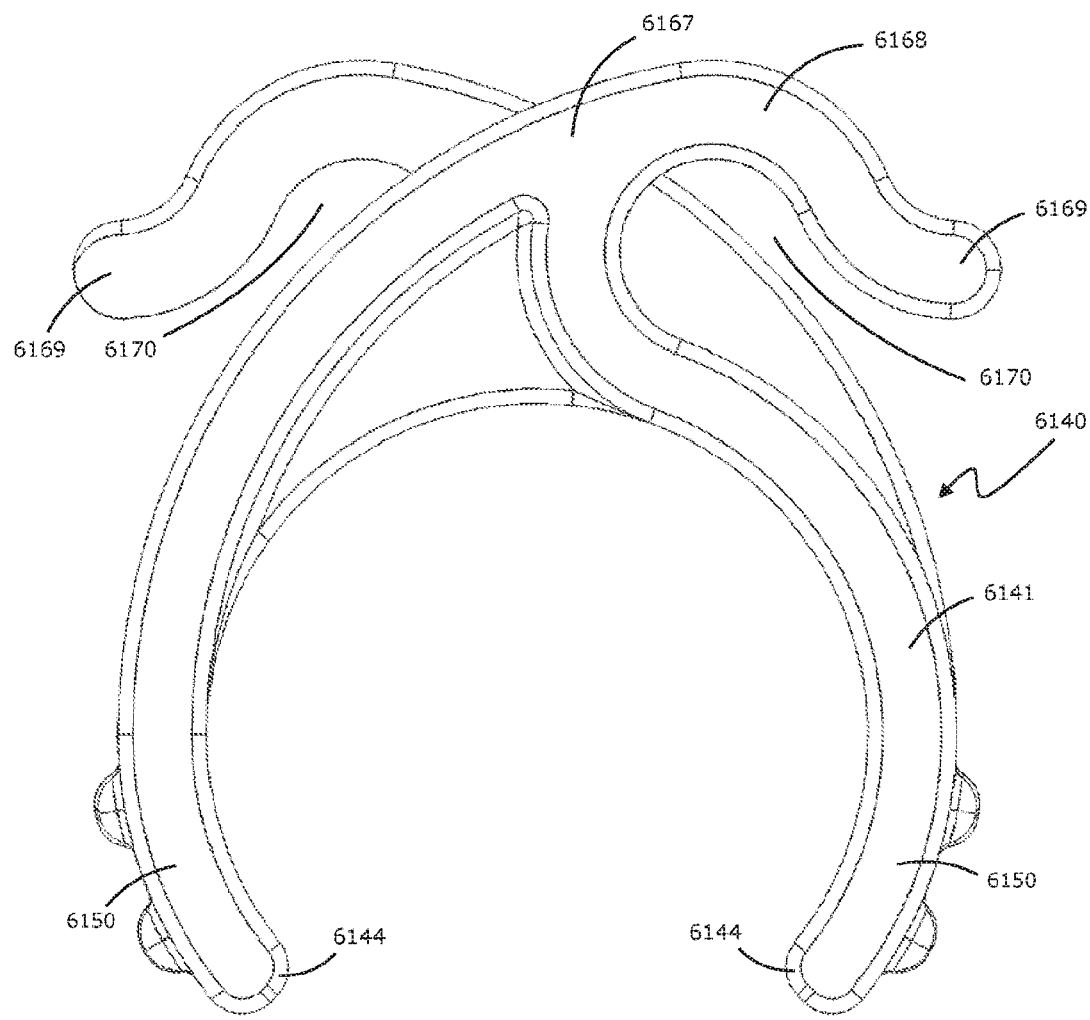
FIG. 57 shows an end view of the attachment member shown in FIG. 56.
Figure 58:
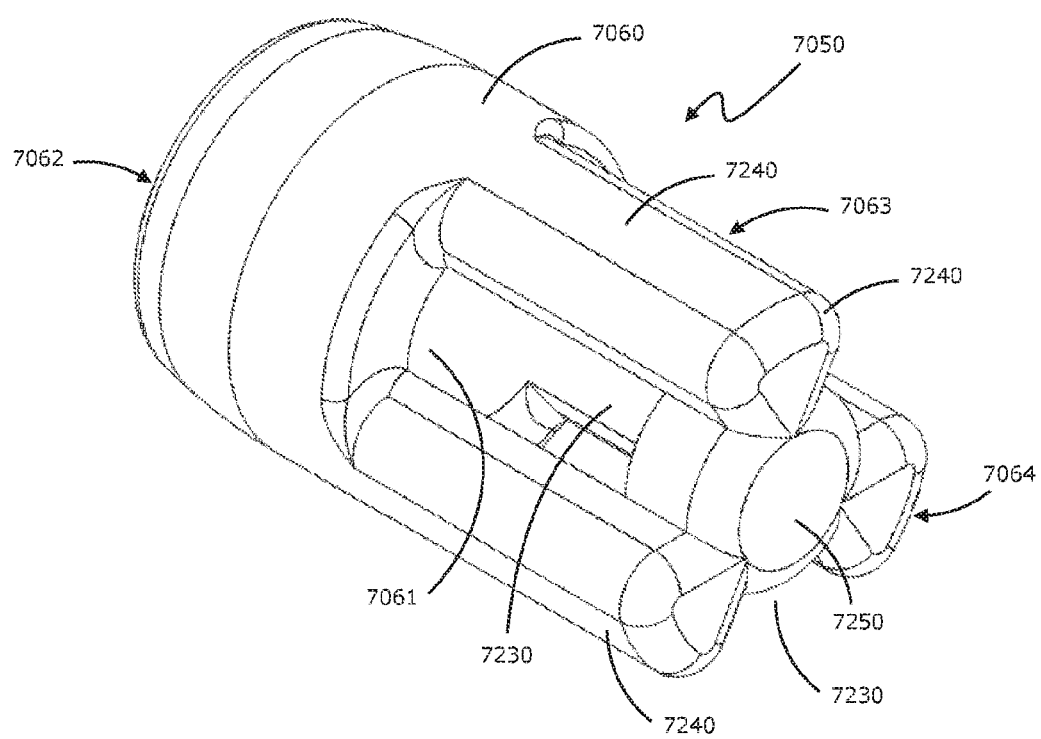
FIG. 58 shows a perspective view of one embodiment of a gas sampling tip.
Figure 59:
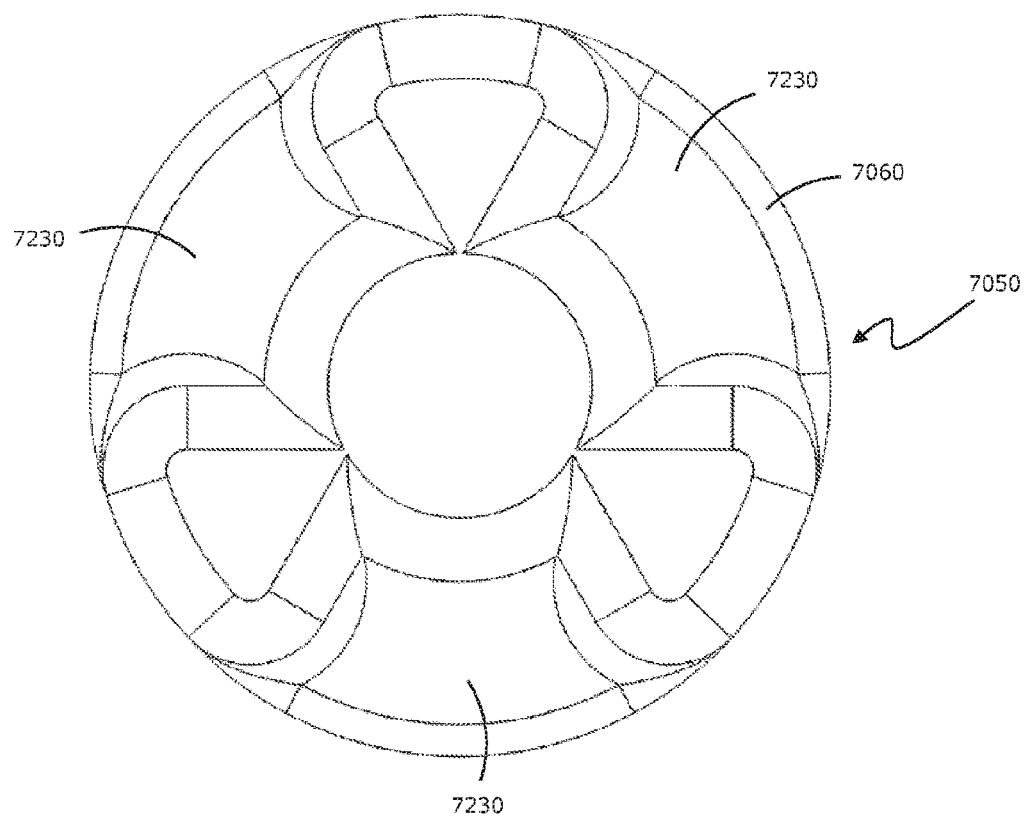
FIG. 59 shows an end view of the distal end of the gas sampling tip of FIG. 58.
Figure 60:
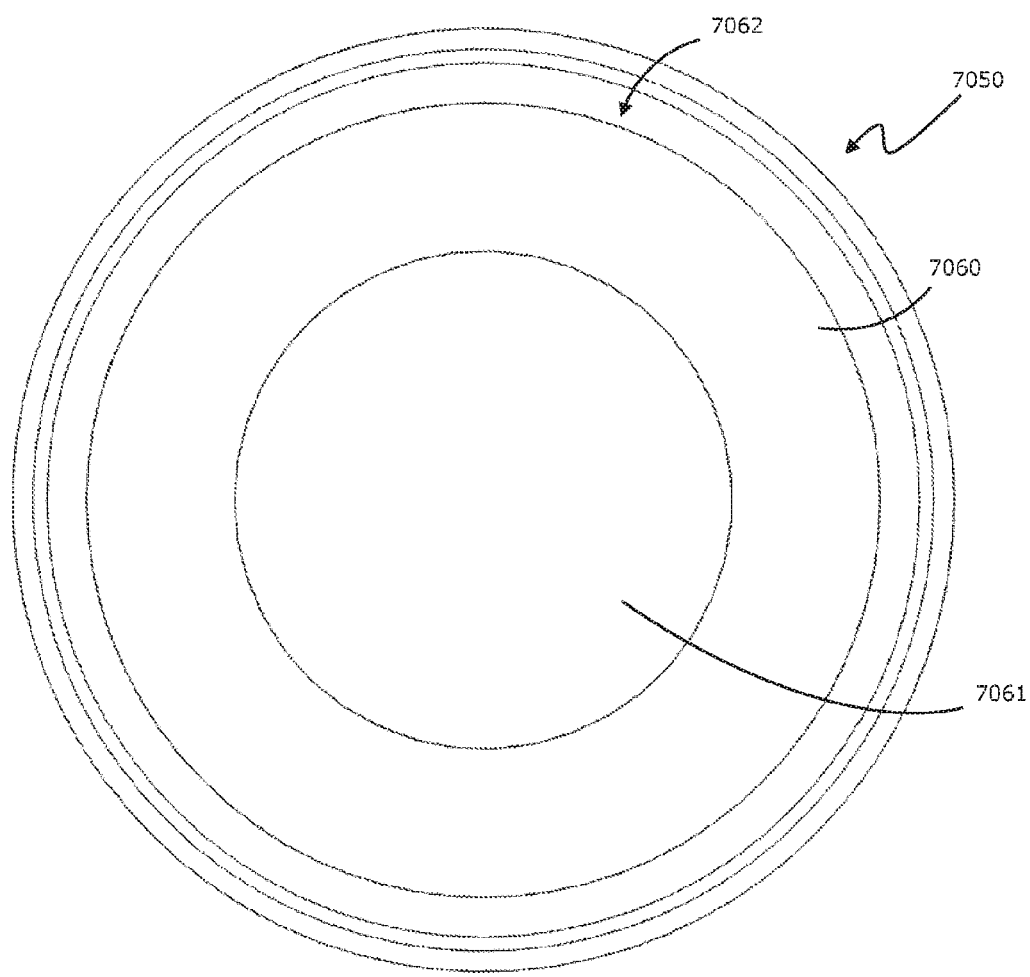
FIG. 60 shows an end view of the connection end of the gas sampling tip of FIG. 58.

In one embodiment, as shown in FIGS. 55 to 57, the attachment member 6140 comprises a body 6141 that is attachable to the breathing apparatus 1000. The body 6141 may clamp onto a portion of the breathing apparatus. In one form, the body 6141 of the attachment member 6140 may form a substantially or partially enclosed sleeve that wraps around a portion of the breathing apparatus 1000.

Where the sleeve is partially enclosed, as shown in FIGS. 55 to 57, the body/sleeve 6141 comprises a pair of spaced apart, projecting resilient arms 6150. Each projecting arm terminates in a side edge 6144. The sleeve 6141 comprises an interior region 6142 and an opening 6143 to the interior region 6142. The arms 6150 may curve toward each other so that the area between the body 6141 and projecting arms 6150 forms the interior region 6142 of the sleeve. The opening 6143 is defined by the arms and side edges 6144 of the sleeve and extends along the length of the sleeve. The interior region 6142 is defined by an inner surface of the attachment member and is shaped and dimensioned to receive a portion of a breathing apparatus 1000, such as a portion of a nasal cannula. The arms 6150 may be configured to be biased toward each other, but may be sufficiently flexible to be pushed apart, such as by pushing a portion of a breathing apparatus 1000 between the arms 6150. The material and dimensions of the sleeve-like body 6141 may be such that at least a portion of the breathing apparatus is held within the interior region 6142 of the sleeve 6141, such as by the arms 6150 clamping onto the breathing apparatus. Other forms of attachment may also be suitable. Typically, the attachment member 6140 is configured to attach to an air or gas delivery tube 8060 of the breathing apparatus 1000, but it is envisaged that the attachment member may be configured to attach to another portion of the breathing apparatus, such as a head strap of the breathing apparatus. For example, if the breathing apparatus comprises a nasal cannula 8040, the attachment member may be configured to attach to the air or gas delivery tube 8060, a manifold 8070 of the cannula, side arms 8080 of the cannula, or a head strap 8090 of the cannula.

In the embodiment shown in FIGS. 55 to 57, the body 6141 of the attachment member 6140 is configured to attach to a substantially curved portion of a breathing apparatus, such as a breathing air or gas delivery tube 8060. In this form, the attachment member 6140 comprises a substantially curved sleeve having curved arms 6150 or arms that at least comprise curved inner surfaces, as shown, so that the arms are configured to clamp against or at least partially wrap around the outer curved surface of the breathing gas delivery tube. In other words, the interior region 6142 is shaped to substantially correspond with the exterior profile of an air or gas delivery tube 8060 of the nasal cannula. For example, the interior region 6142 of the sleeve may be substantially curved to provide the interior region with a substantially arcuate inner surface and to provide the sleeve with a substantially C-shaped cross section so that the sleeve can at least partially wrap around a portion of the air or gas delivery tube 8060 or other suitable curved portion of the breathing apparatus, such as a curved portion of a manifold of a nasal cannula. In another form, the sleeve may form a substantially U-shaped cross section to at least partially wrap around a portion of the air or gas delivery tube 8060 or other suitable curved portion of the breathing apparatus, such as a curved manifold. In yet another form, at least the substantially arcuate inner surface of the sleeve may be formed from a plurality of substantially planar regions/surfaces arranged in series to form a substantially enclosed or fully enclosed sleeve. Where the sleeve is substantially enclosed, the substantially planar surfaces may be arranged to form a sleeve having a substantially C-shaped cross-section or to form a sleeve having a substantially U-shaped cross-section. In any form, at least the inner surface of the sleeve may be shaped to substantially match the external shape of the portion of the breathing apparatus to which the sleeve will be attached. For example, if the sleeve will be attached to a side arm of a nasal cannula that has a substantially thin rectangular profile, the inner surface of the sleeve may be formed of three substantially planar regions joined at right angles to provide the sleeve with a substantially angular U-shaped profile.

The sleeve may be formed from a substantially flexible, resilient material, such as a metal or polymeric material that allows the spaced apart side edges 6144 or arms of the sleeve to be biased toward each other in a rest position and to move apart from each other, as the sleeve is pushed over a portion of the nasal cannula, and to substantially return to or towards the original rest position. Typically, the width of the opening between the side edges 6144 is less than the diameter of the portion of the air or gas delivery tube 8060 (or other part of the breathing apparatus) that is held within the sleeve so that the breathing apparatus is held securely within the sleeve.

In one embodiment, the inner surface of the sleeve 6141 may comprise a plurality of ribs to engage or interlock with rib-like formations on an outer surface of a corrugated breathing air or gas delivery tube 8060.In one embodiment, the attachment member 6140 is removably attachable to one of the side arms 8080 of a nasal cannula 8040 (or the side arm of a mask) by any suitable form of attachment. For example, the attachment member 6140 may comprise a pair of spaced apart, projecting arms 6150 that are biased toward each other and that are configured to fit over opposing side surfaces of a side arm of the cannula or mask to clamp the attachment member to the side arm. To fit the attachment member 6140 to the side arm, the attachment member 6140 may be positioned so that a side edge of the side arm is located at the opening between the projecting arms 6150 of the attachment member 6140. The attachment member is then pushed onto the side arm by sliding the projecting arms 6150 of the sleeve 6141 over opposing front and rear surfaces of the side arm, causing the arms 6150 to spread apart. The biased nature of the arms 6150 causes the arms 6150 to clamp against the side arm.

In another form, the attachment member may comprise a hinged clasp comprising a pair of arms attached together at a closed, hinged end and comprising an opposing receiving end that is configured to open or close by moving the arms of the clasp toward and away from each other to close and open the hinge. The receiving end of the clasp may comprise a locking system configured to releasably lock the two arms of the clasp together. Any suitable locking system may suffice, such as a hook or post located on one arm of the clasp and configured to engage with a hook or aperture located on the other arm of the clasp. To fit the attachment member to the side arm, the receiving end of the clasp is opened to allow one arm of the clasp to be slid beneath the side arm of the nasal cannula or mask. The other arm is then placed on top of the side arm and is locked to the lower arm to clamp onto the side arm and hold the hinged clasp in position. Where the attachment member forms a clamp, the arms or clamping members of the clamp may be shaped to substantially compliment the shape of the side arm to maximise the clamping hold on the side arm and, preferably, to also maximise patient comfort.

In one embodiment, the body or sleeve 6141 of the attachment member 6140 comprises at least two offset clips 6167 (a first clip and a second clip) attachable to the gas sampling conduit 6163. The offset clips may be located on an outer surface of the attachment member. The offset arrangement of the clips 6167 causes the gas sampling conduit 6163, when attached, to follow a tortuous path. This helps to hold the sampling conduit 6163 in position and reduces the risk that the sampling conduit may be accidentally pulled out of the patient's oral or nasal cavity or accidentally pushed too far into the patient's oral or nasal cavity.

Each clip 6167 comprises a tube receiving region 6170 within which a portion of the gas sampling conduit 6163 may be held.

In one embodiment, each clip 6167 forms a hook comprising an arm 6168 extending from the clip body 6141 and terminating in a distal end 6169 suspended at a distance from the outer surface of the attachment member body 6141. The space between the distal end 6169 of the clip and the outer surface of the attachment member 6140 forms a clip opening. The arm 6168 may be curved. For example, the arm 6168 may comprise an inner surface that forms a substantially curved or concave tube receiving region 6170. The curved profile of the tube receiving region 6170 may be dimensioned to substantially correspond with the curved exterior profile of the gas sampling conduit 6163. In one form, the diameter of the curved tube receiving region 6170 may be at least as large as the diameter of the gas sampling conduit 6163. In another form, the diameter of the curved tube receiving region 6170 may be slightly smaller than the gas sampling conduit diameter to press against the gas sampling conduit and help maintain the position of the gas sampling conduit within the clips 6167. In one form, the hooked clips may face in opposing directions. For example, a first hook may face toward one side of the gas delivery tube (when located on the tube) and the second hook may face toward the opposing side.

To fit the gas sampling conduit 6163 to the attachment member 6140, the conduit 6163 is pushed through the opening of one clip 6167 and then through the opening of the other clip 6167 to follow a tortuous path that holds the conduit in position within the clip. The length of the free end portion of the conduit can be readily adjusted by unhooking/removing the conduit from a first clip and then pulling the conduit in the desired direction so that the conduit slides through the second clip until the free end portion is at the desired length. The conduit may then be hooked into the first clip again to secure the conduit in position.

The gas sampling conduit 6163 may be removably installable within the clips 6167 of the attachment member 6140 so that the conduit can be replaced if needed. Therefore, the gas sampling conduit may be removed from the attachment member, by pulling the sampling conduit out of the clip openings. Alternatively, the gas sampling conduit may be permanently retained in the attachment member.

Each clip 6167 is typically formed from a flexible, resilient material that allows at least a portion of the hook to move away from the body 6141 as the gas sampling conduit 6163 is pushed into the tube receiving region 6170 and to substantially return to the original state once the gas sampling conduit 6163 is located within the tube receiving region 6170. In this embodiment, the distance between a distal end portion of each hooked arm 6168 and the body 6141 (the clip opening) may be less than the diameter of the gas sampling conduit 6163 to help prevent the gas sampling conduit 6163 from inadvertently detaching from the clip 6167.

The clips 6167 may be configured to loosely hold the gas sampling conduit 6163 in position within the clips 6167 or to firmly hold the conduit 6163 in position, depending on the shape and dimensions of the tube receiving region 6170 in each clip 6167 and the gas sampling conduit 6163.

In one embodiment, each clip 6167 may be configured to clamp onto at least a portion of the gas sampling conduit 6163 with sufficient force to attach the conduit 6163 to the clip 6167 without blocking the gas flow path within the sampling conduit 6163.

Figure 65:
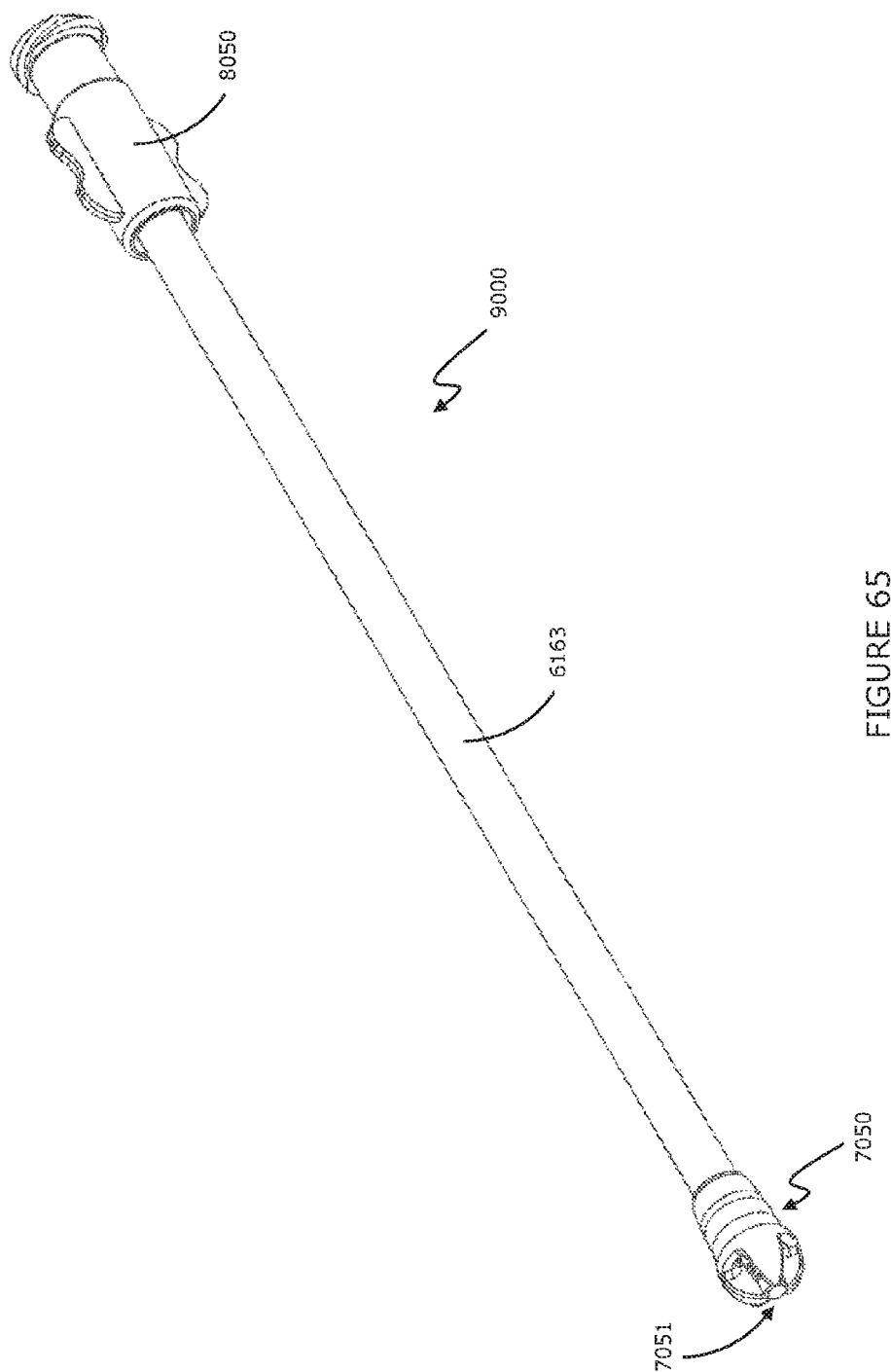
FIG. 65 shows a perspective view of one form of gas sampling assembly comprising a gas sampling tip connected to a gas sampling tube that is connected to a connector in the form of a luer.
Figure 66:
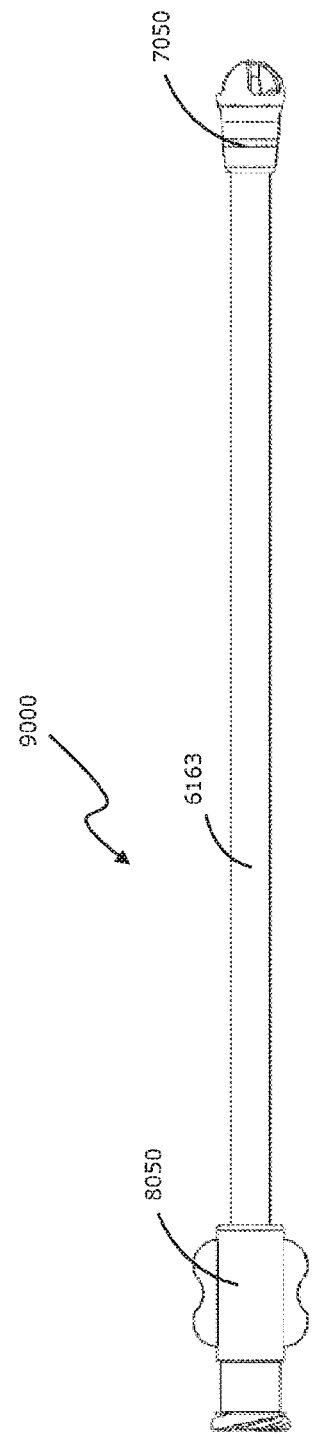
FIG. 66 shows a side view of the assembly of FIG. 65.
Figure 67:
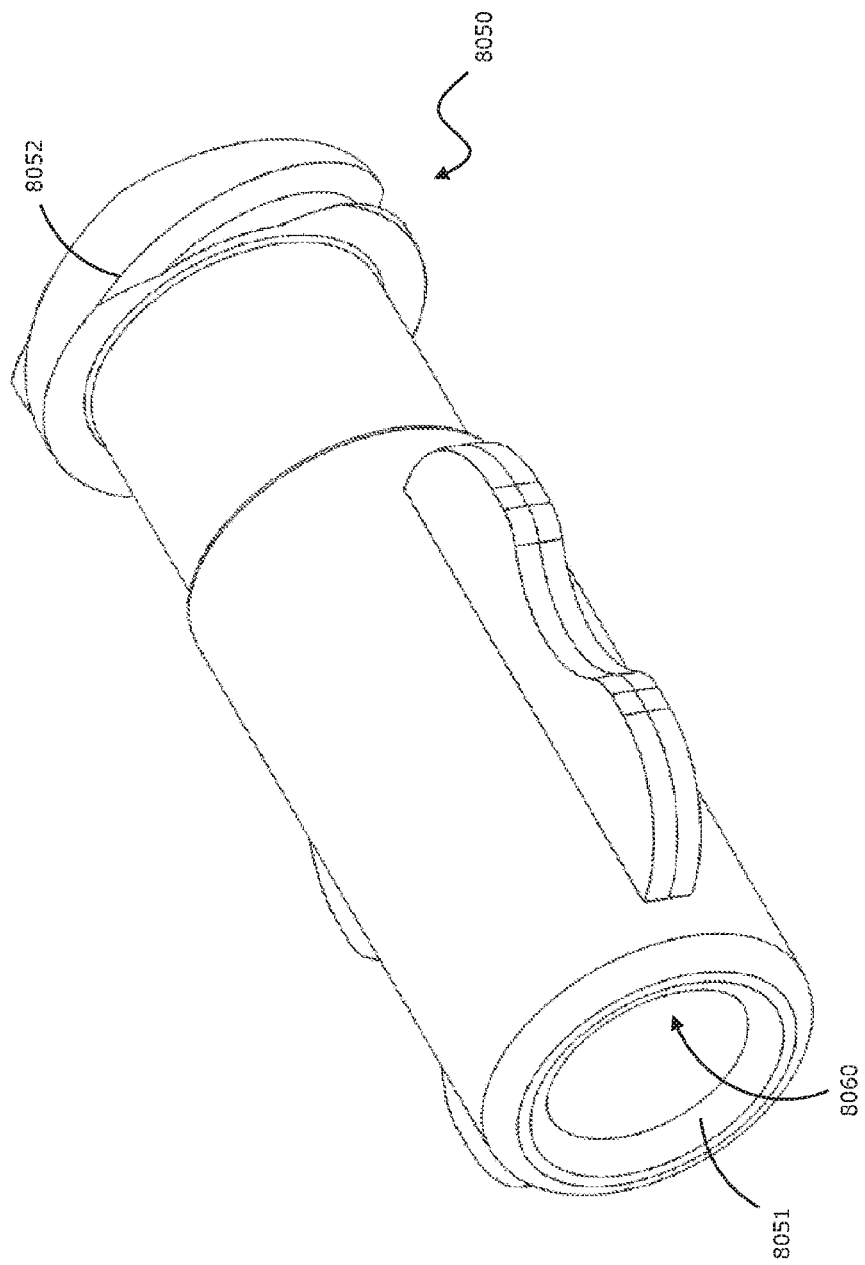
FIG. 67 shows a perspective view of one form of connector (in this case a luer) that may be used to connect a gas sampling conduit to a respiratory gas monitor.

A connection or attachment member 8050, such as a luer connection as shown in FIGS. 65 to 67, may be provided at or near the outlet 109 of the gas sampling conduit 101 of a gas sampling interface 100 to fluidly connect the sampling conduit 101 and interface 100 to the gas sampling tube of a respiratory gas monitor. It will be appreciated that any other means of connection may alternatively be employed between the interface and the gas sampling tube. In another form, the outlet of the gas sampling conduit may be directly connected to an inlet of a respiratory gas monitor.

Figure 70:
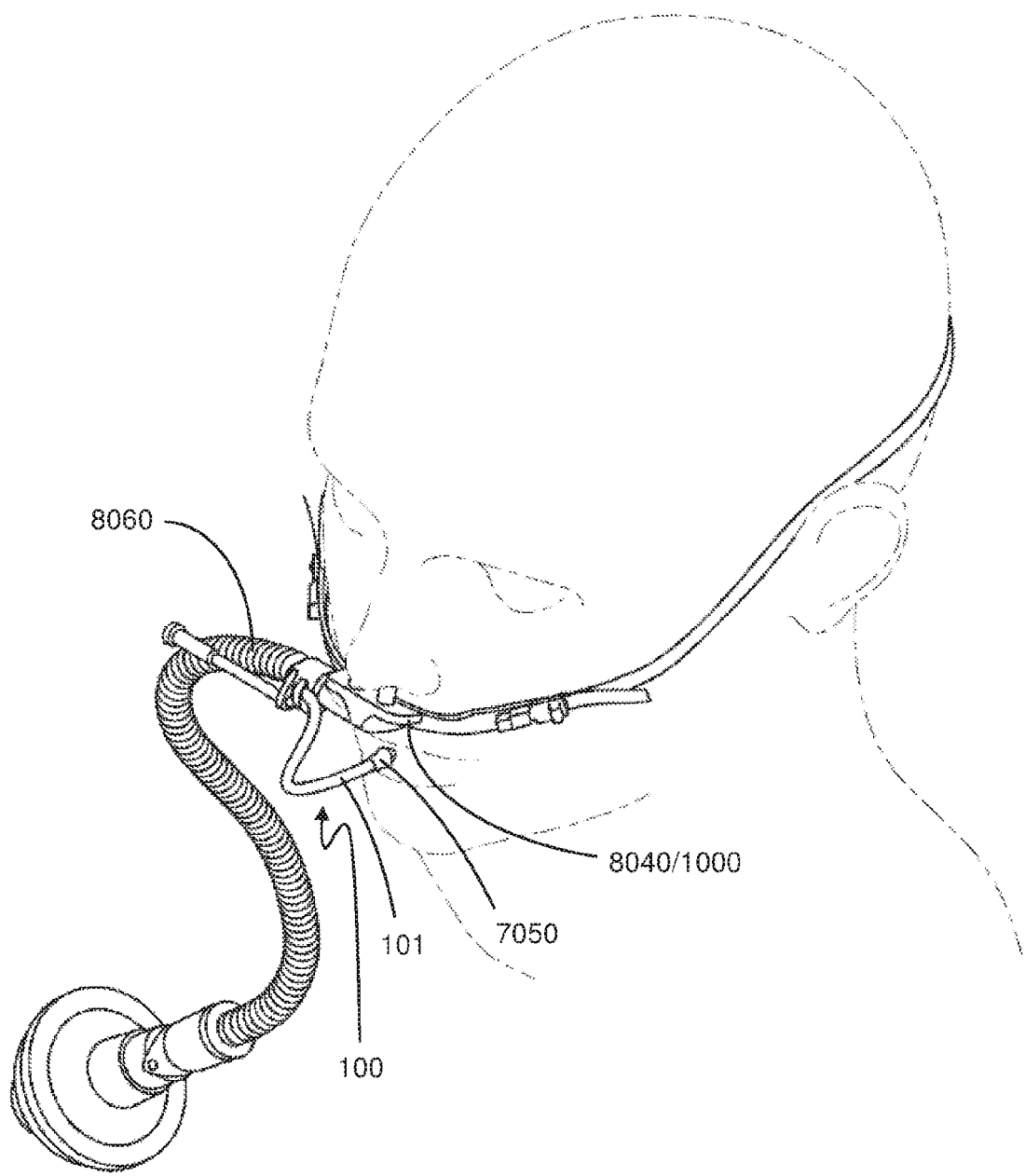
FIG. 70 is a schematic view of a patient wearing one form of gas delivery system and one form of gas sampling interface in which the tip of the gas sampling interface is positioned proximate to the patient's mouth to sample exhaled and/or expired gases from the mouth.
Figure 71:
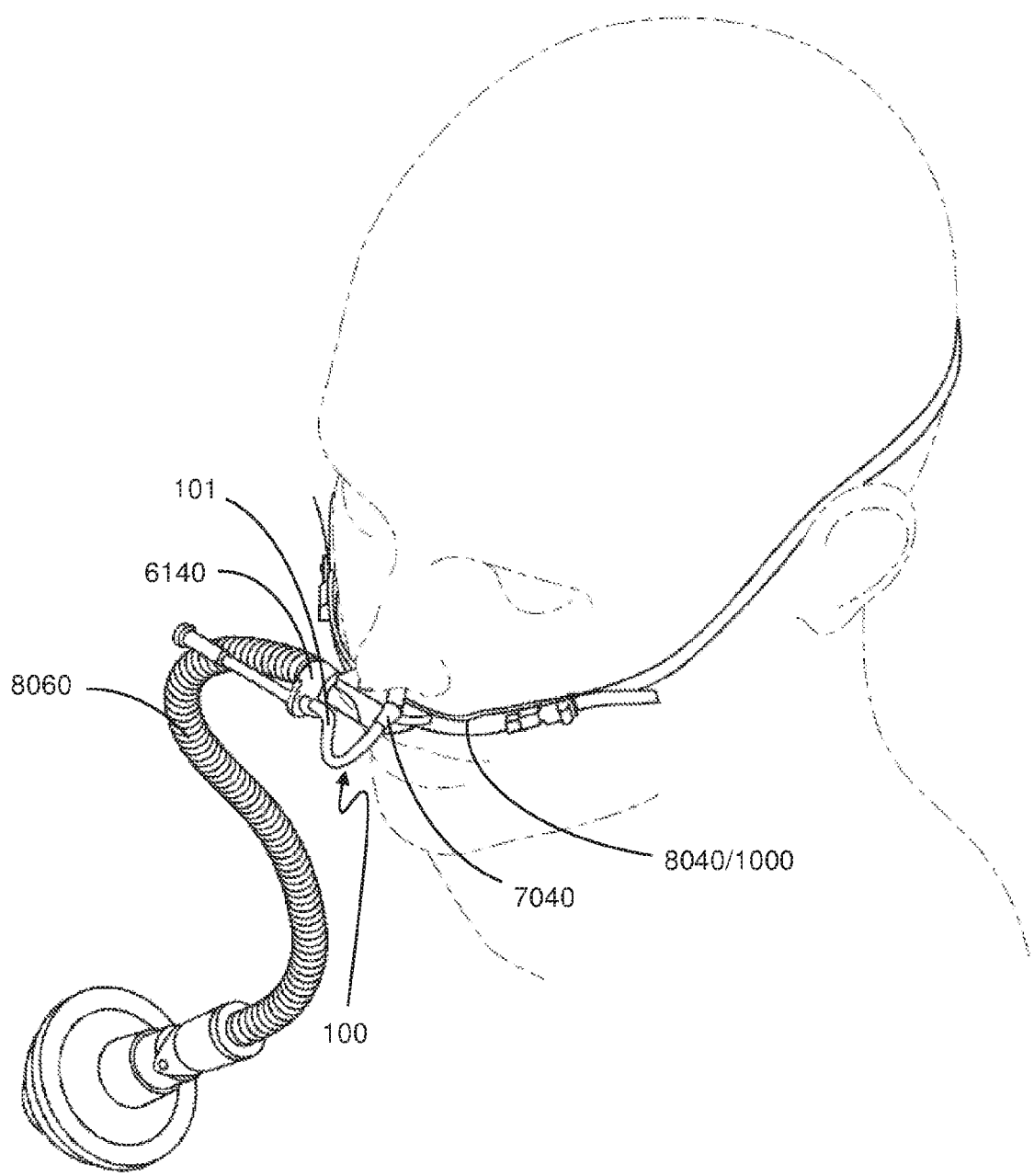
FIG. 71 is schematic view of a patient wearing another form of gas delivery system and also wearing the gas sampling interface of FIG. 70 in which the tip of the gas sampling interface is positioned proximate to a nare of the patient's nose to sample exhaled and/or expired gases from the nose.

Using a flexibly resilient sampling conduit having a support structure, such as a wire, as described above, and attaching the conduit to a breathing apparatus using an attachment member, as described above, that allows the length of the free end portion of the conduit to be adjusted is a particularly advantageous embodiment because the conduit and therefore the sampling interface is selectively positionable (resiliently bendable/formable) to be placed near mouth or nare, as shown in FIGS. 70 and 71. The distal end of sampling interface may be placed in the mouth at about the position of the teeth, near the mouth, or near one of the patient's nares or inside of the nare. If a nasal cannula is used as a breathing apparatus, it may be difficult to fit both a prong of the cannula and the sampling interface into a nare of the patient, but depending on the size of the end portion or tip of the sampling interface and how anesthetized the patient is, the sampling interface and cannula prong could both be inserted into the nare. Alternatively, the sampling interface could be located just outside of the nare. Therefore, the versatility of the sampling interface due to its positioning ability means that it can be used for patients that exhale and/or expire gas through the mouth or nose (or, for an apnoeic patient, for patients whose respiratory gases exit their bodies primarily or solely through either the mouth or the nose). The interface can be easily repositioned as necessary to suit the patient. The interface may also be repositioned to suit the needs of the clinician and the constraints of the medical procedure. For example, many times during surgery the patient's mouth may be held open by other medical devices or equipment, which would make it likely that a good respiratory gas trace of expired and/or exhaled breath could be picked up at the patient's mouth by a gas sampling interface/device as disclosed herein. Alternatively, if the patient's mouth is closed, the sampling interface may be easily moved to be located proximate the nare, or the distal end or tip of the sampling interface may be located between the patient's lips, such as against their teeth. Taking a trace of exhaled and/or expired breath from a patient's mouth when the patient is receiving high flow therapy through a nasal cannula has been found to be particularly effective. This is because placing the sampling interface at the mouth enables a trace to be found because the resistance to the flow of gas into the sampling interface is generally less through the mouth than the resistance created by the high flow of breathing gas being provided to the nares.

FIGS. 58 to 64 show further embodiments of gas sampling tips 7050 that may be connected to a gas sampling conduit to receive gases exiting from a patient. The sampling tips 7050 may be integrally formed with the gas sampling conduit 6163 or formed separately and then attached to the free end/gas inlet end of the sampling conduit 6163. The sampling tips 7050 may each be attached to the free end of the sampling conduit 6163 using any suitable form of attachment. For example, a sampling tip may be welded to the sampling conduit; screwed to a threaded free end of the sampling conduit; glued or otherwise adhered to the free end of the sampling conduit; or the sampling tip and sampling conduit may be attached together in a snap fit arrangement, friction fit arrangement, or the like.

In preferred embodiments, the gas sampling tip 7050 is formed of a soft or semi-soft compressible material. Sampling tips that are formed from a rigid or hard material could cause an injury to a patient or could damage the patient's teeth, especially if the tip is placed between the teeth and the patient inadvertently bites down on the tip. These risks are avoided or at least mitigated by providing a sampling tip that may comprise a compressible material that is less likely to cause injury or harm to the patient.

In one embodiment, the sampling tip 7050 comprises a body 7060 comprising a substantially hollow interior region 7061 configured to be in fluid communication with the inlet of a gas sampling conduit 6163 when the sampling tip 7050 is connected to the sampling conduit 6163. The body 7060 comprises one or more side walls forming an outer side surface of the body, a proximal connection end 7062 for connecting to the free end of the gas sampling conduit such that the hollow interior region is in fluid communication with the gas sampling conduit and a distal end portion 7063 that terminates in a distal end 7064 of the sampling tip 7050.

In one form, the connection end 7062 may be glued onto the gas sampling conduit 6163. In another form, the connection end 7062 may be threaded for connecting to a threaded end of the gas sampling conduit 6163 so that the sampling tip may be screwed onto and off the free end of the sampling conduit. In yet another form, the connection end may comprise a lip configured to fit onto a collar of inlet end of the sampling conduit to connect the sampling tip and conduit in a snap fit arrangement. Alternatively, the inlet end of the sampling conduit may comprise a lip that fits onto a collar of the connection end of the sampling tip.

The sampling tip 7050 comprises at least one inlet/gas receiving aperture 7230. Gases exhaled or expired by a patient may be received by the inlet/gas receiving aperture 7230, which is in fluid communication with the substantially hollow interior region 7061 of the body 7060, so that the received gases can pass through the body 7060 of the sampling tip and into inlet of the gas sampling conduit. Each inlet/gas receiving aperture forms an opening to the hollow interior region of the body of the tip.

In one form, the gas receiving aperture 7230 may extend from the distal end 7064 of the sampling tip along a side of the sampling tip body 7060. Preferably, the gas receiving aperture 7230 forms an elongate opening in the distal end portion 7063 of the gas sampling tip.

Figure 68C:
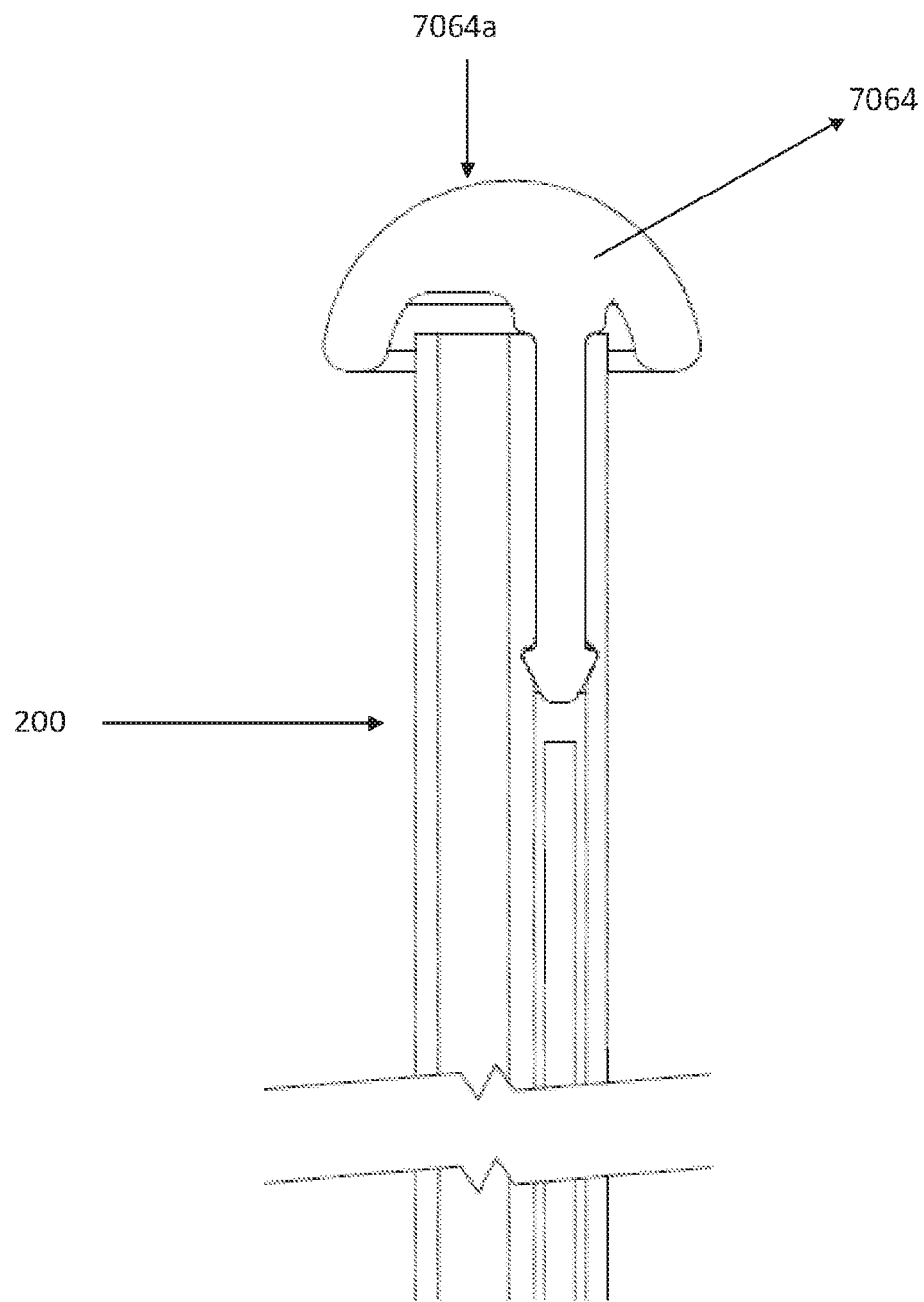
FIG. 68C is a cross-sectional side view of the gas sampling tip of FIGS. 68A and 68B.

In one form, the sampling tip 7050 comprises an end wall at its distal end 7064 and one or more gas receiving apertures located on one or more side walls of the sampling tip. In one form, the gas receiving aperture 7230 may extend around substantially the entire outer periphery of the sampling tip, such as around the entire outer periphery of the outer side surface. Where the sampling tip has a substantially round/circular cross-section, the gas receiving aperture 7230 may extend around the circumferential outer surface of the sampling tip to form an annular ring-like aperture, as shown in FIGS. 68A to 68C. In another form, the gas receiving aperture 7230 may extend around the circumferential outer surface of the sampling tip in a substantially helical arrangement, similar to the helical thread of a corkscrew.

The end wall may be substantially transverse to, and offset from, the gas receiving aperture(s). In one form, the end wall may be longitudinally offset at a distance equal to, or greater than, the width of the gas inlet(s).

The cross-sectional area of the end wall may be less than, substantially equal to, or greater than the cross-sectional area of the hollow interior region of the sampling tip body.

In one form, the cross-section of the end wall is the same as, or greater than, the cross-section of the gas receiving aperture(s)/inlet(s).

In some embodiments, as shown in FIGS. 58 to 66, the gas sampling tip 7050 may comprise multiple inlets/gas receiving apertures 7230. For example, the sampling tip 7050 may comprise a pair of gas receiving apertures 7230 extending from the distal end of the sampling tip and along the sides of the distal end portion 7063 of the gas sampling tip body 7060. The apertures 7230 may or may not be evenly spaced from each other. For example, the apertures 7230 may be located on substantially opposing sides of the body 7060 or the apertures 7230 may be located closer to each other in at least one direction. In other embodiments, the gas sampling tip 7050 may comprise two, three, four or more gas receiving apertures 7230. The apertures 7230 may or may not be evenly spaced from each other.

In the embodiments shown in FIGS. 58 to 66, the gas sampling tip 7050 comprises three gas receiving apertures 7230 that are evenly spaced around the distal end and sides of the sampling tip 7050. The spacing of the apertures 7230 can be seen best in FIGS. 58, 59, 61 and 63.

Each portion of the sampling tip body 7060 located between the gas receiving apertures 7230 forms a flute 7240 that terminates at the distal end of the sampling tip 7050. A central support 7250 may be located at the distal end of the sampling tip 7050 and may be connected to the flutes 7240. The central support 7250 provides the flutes 6240 with additional strength and positional integrity to prevent the flutes 7240 from crushing together and at least partially blocking the gas receiving apertures 7230. The central support 7250, flutes 7240, and body 7060 of the sampling tip 7050 together define edges of the gas receiving apertures 7230.

The body 7060 of the gas sampling tip 7050 may have a substantially cylindrical form and the flutes 7240 may be substantially evenly spaced around the circumference of the distal end portion 7063 of the gas sampling tip 7050. In one form, an inner portion of each flute may comprise a cut out region to form an enlarged opening within the tip.

In one form, as shown in FIGS. 68A to 68C, the distal end 7064 of the sampling tip may be supported by a support member comprising a core/strut/arm/elongate extension 7070 connected to the end wall and the body 7060. The support member 7070 may be located substantially centrally along a longitudinal axis of the sampling tip or the support member may be substantially laterally offset from the centre of the longitudinal axis of the sampling tip. For example, the support member 7070 may be connected to at least one interior wall of the body or to the outer side surface of the body of the sampling tip. In one form, as shown in FIG. 68C, the body 7060 of the sampling tip may form a plug having a projecting support member 7070 comprising a strut connected to a distal end 7064 of the sampling tip. The plug-like body 7060 may be configured to be located within a lumen or subsidiary channel in the gas sampling conduit 201, so as to attach the tip to the conduit without blocking the gas receiving inlet of the sampling conduit. For example, the subsidiary channel may be the first, support lumen 211 of a gas sampling conduit 201, such as the conduit shown in FIG. 2. The support member/strut may be offset from the body of the tip 7060 and/or from the longitudinal centre line of the gas sampling conduit 201, as shown in FIGS. 68A to 68C. This arrangement is particularly advantageous where the body of the tip is configured to engage with an offset body receiving lumen or aperture that lies adjacent to and at one side of the inlet of a gas sampling conduit.

In another form, the sampling tip body 7060 may be configured to be received within the inlet located at the distal end of a gas sampling conduit. In this form, the sampling tip comprises a body 7060 that is shaped and dimensioned to be received within the gas inlet of the sampling conduit. A support member comprising a core/strut/arm/elongate extension or the like 7070 projects from the body 7060 and connects to a distal end portion 7064 of the sampling tip 7050 to hold the distal end portion 7064 at a distance from the body 7060. For example, the support member or strut

Figure 69C:
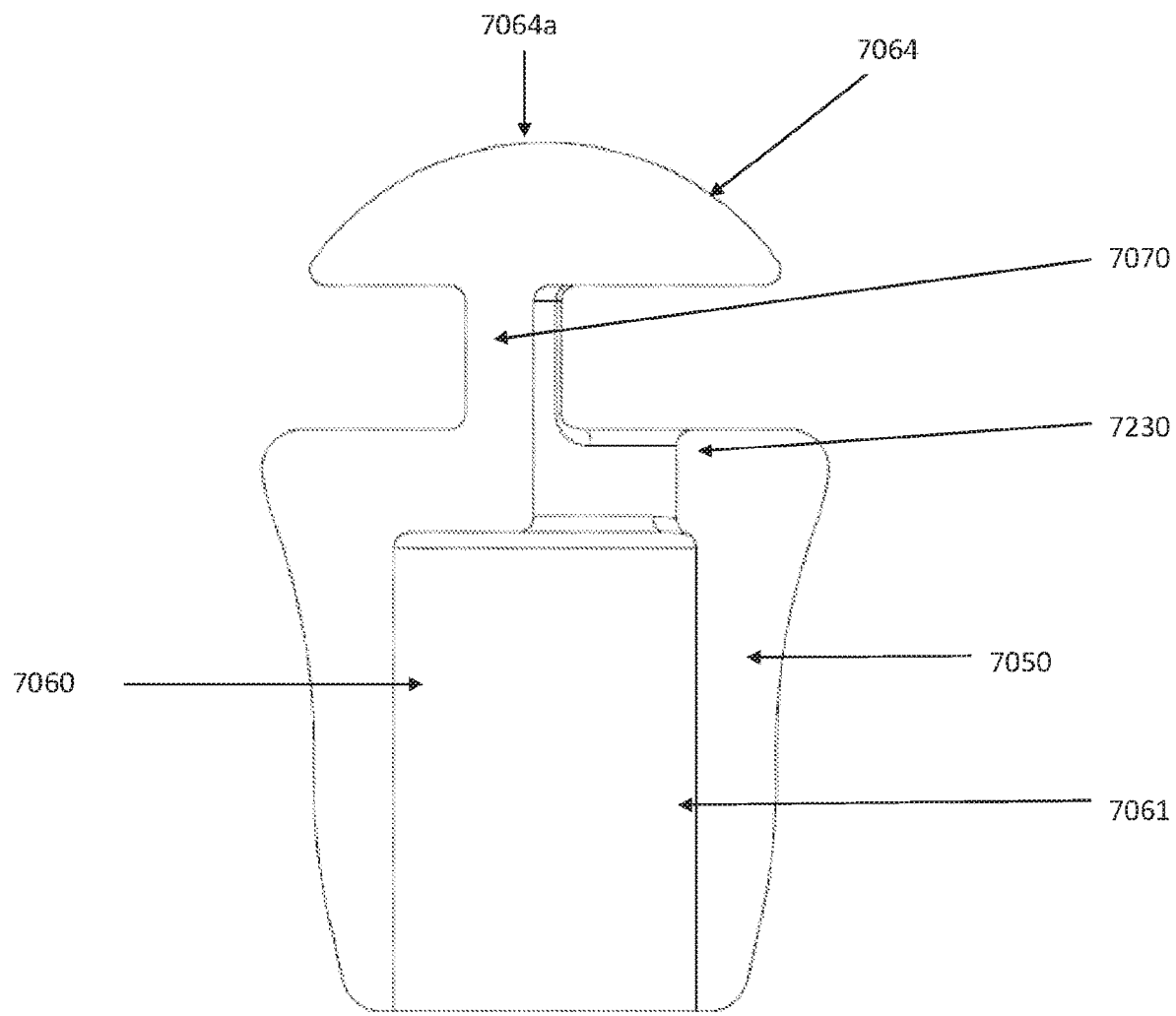
FIG. 69C is a cross-sectional side view of the gas sampling tip of FIGS. 69A and 69B.

7070 may project from an upper surface of the sampling tip body 7060. The support member/strut 7070 may project substantially centrally from the upper surface of the body 7060 or the strut 7070 may be offset from the centre of the body 7060. The strut 7070 and distal end portion 7064 of the sampling tip 7050 may be configured so that the distal end portion 7064 is cantilevered from the strut 7070 or at least projects beyond the periphery of the strut 7070. The arrangement of the distal end portion and support member form a shield over the inlet(s)/gas receiving aperture(s) of the gas sampling tip. Because the sampling tip body 7060 is placed within the gas inlet of the gas sampling lumen, in a plug-like arrangement, at least one gas receiving aperture 7230 is formed in the sampling tip 7050 to allow gas to pass through the sampling tip 7050 by passing through the gas receiving aperture(s) 7230 and through the hollow body 7060 of the tip and into the gas sampling conduit. In one form, at least one gas receiving aperture 7230 is formed in the upper surface of the body 7060 and is in fluid communication with a substantially hollow interior 7061 of the body that opens at its proximal end to form fluid flow path with the gas sampling conduit, as shown in FIGS. 69A to 69C. In another form, at least one gas receiving aperture 7230 may be formed in the support member/strut 7070 and the support member/strut 7070 may comprise a substantially hollow body in fluid communication with the gas receiving aperture 7230 and with a substantially hollow interior of the sampling tip body 7060 so that gas can flow through the gas receiving aperture(s) 7230, through the hollow body 7060 and into the gas sampling conduit.

In another form, the support member/strut 7070 may extend from at least one side wall of the gas sampling tip body 7060 so that the distal end 7064 is cantilevered from the strut 7070. For example, a support member/strut 7070 may extend from the body (so that the outer surface of the body extends along the outer surface of the strut) and the distal end may be cantilevered from the strut. In one form, the end wall is integrally formed with the body 7060.

In one form, as shown in FIGS. 68A to 69C, the distal end portion 7064 of the sampling tip may comprise a curved or dome shaped end wall 7064a that forms a shield to protect the inlet(s)/gas receiving aperture(s) of the gas sampling tip from suctioning against the patient's cheek, mouth, lip, or nare. The end wall also advantageously prevents saliva entering directly into the hollow interior region of the body—particularly from the longitudinal direction. This is important in preventing blockages in the sampling tip and gas sampling conduit.

Figure 61:
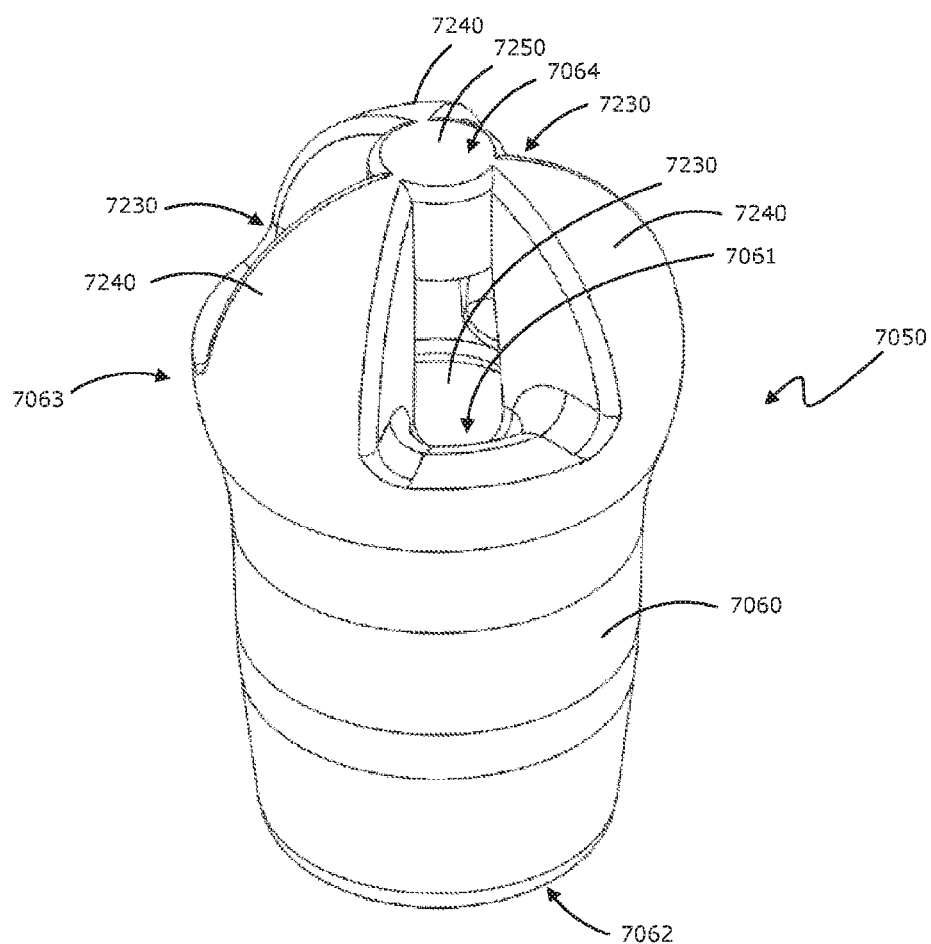
FIG. 61 shows a perspective view of another embodiment of gas sampling tip.
Figure 62:
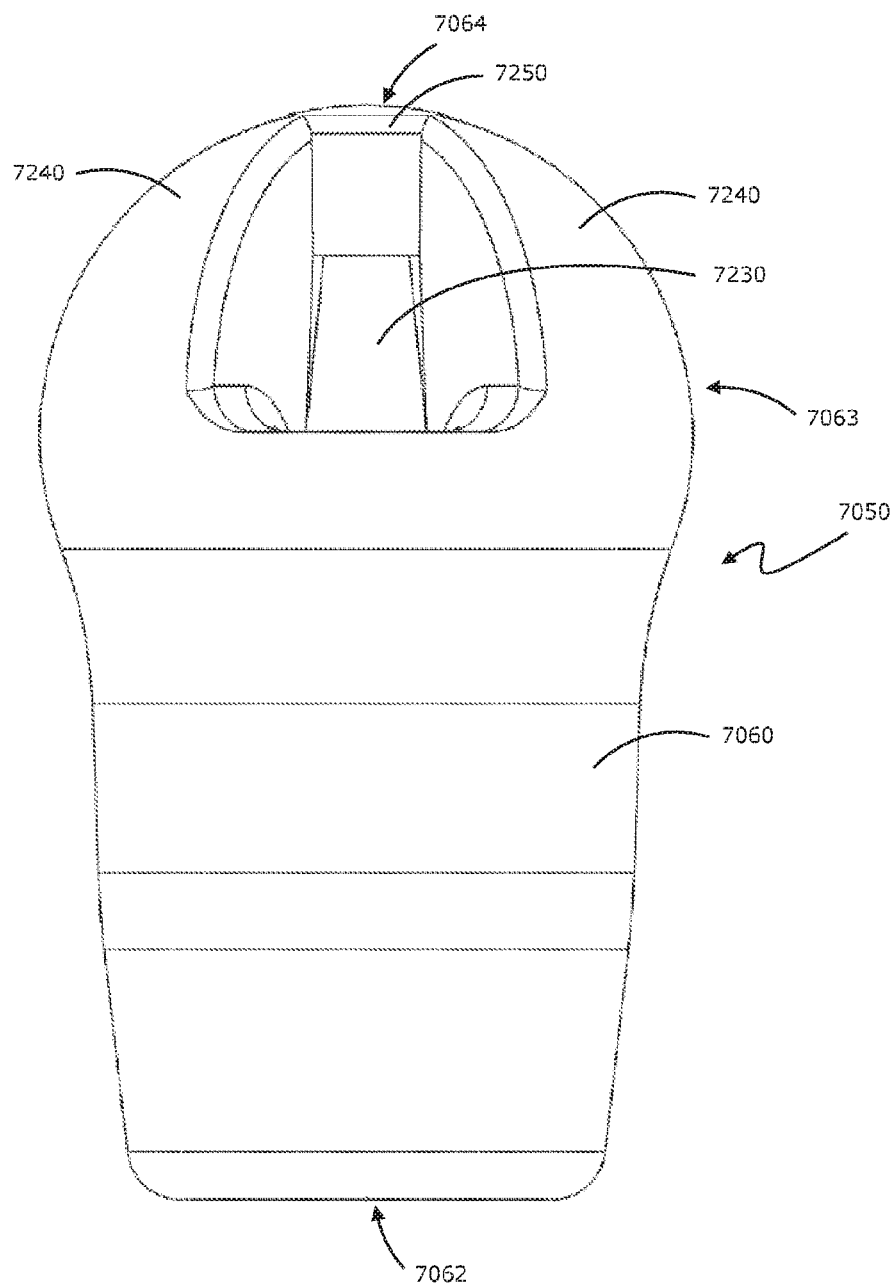
FIG. 62 shows a side view of the gas sampling tip of FIG. 61.
Figure 63:
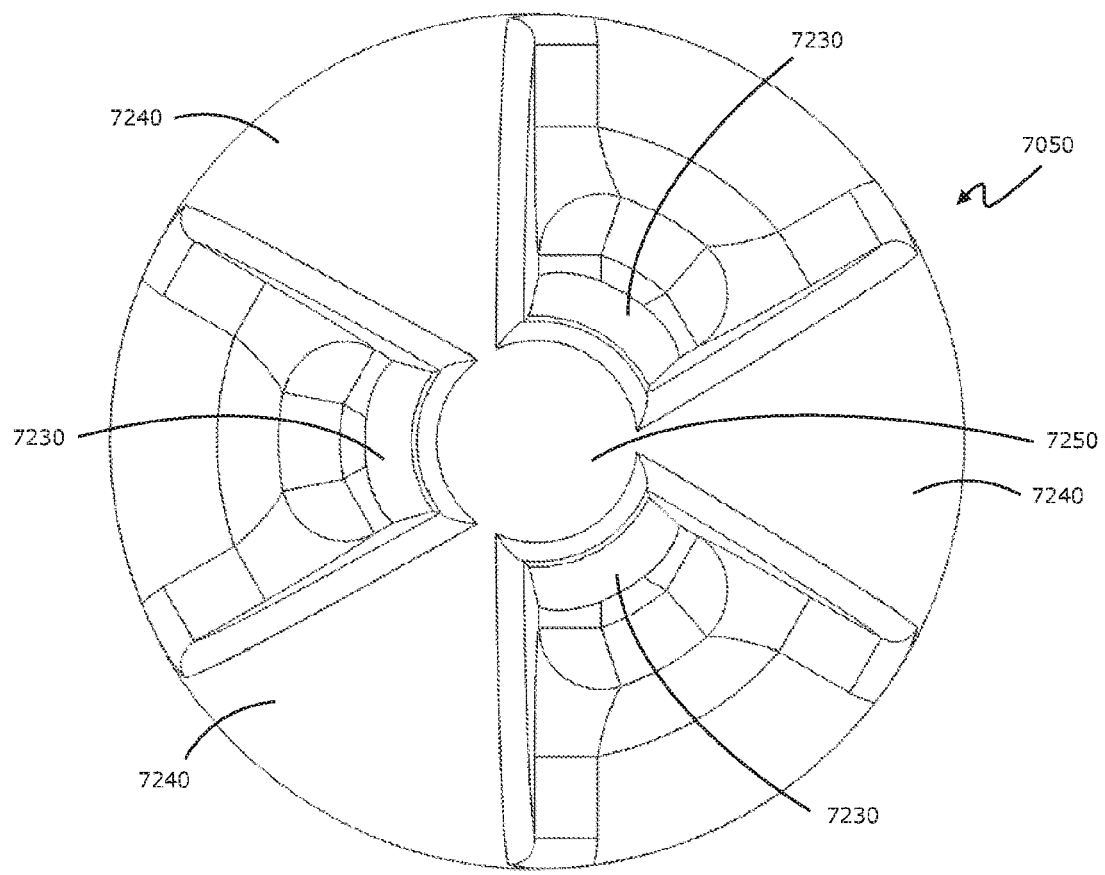
FIG. 63 shows an end view of the distal end of the gas sampling tip of FIG. 61.
Figure 64:
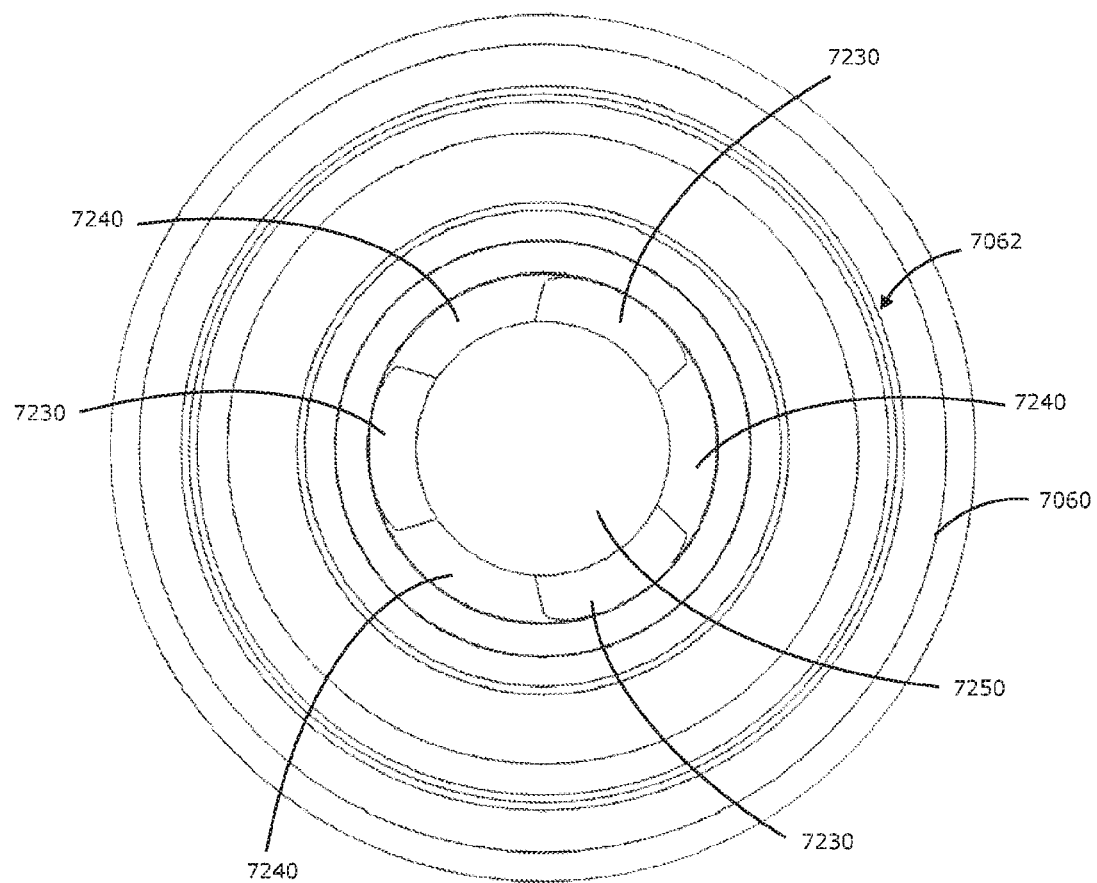
FIG. 64 shows an end view of the connection end of the gas sampling tip of FIG. 61.

In the embodiment shown in FIG. 61, the distal end 7064 of the gas sampling tip 7050 (comprising the central support and distal ends of the flutes) is outwardly curved or convex to form a protruding shield that prevents the end opening of the gas receiving apertures 7230 from suctioning against the patient's cheek, mouth, lip, or nare. The side surfaces of the flutes 7240 at the distal end portion of the sampling tip 7050 may also be outwardly curved to form a substantially bulbous distal end.

The sampling tip and/or sampling tube and/or attachment member may be single use products for use by a single patient on a single occasion, or may be configured to be re-usable by being made from material that is suitable for cleaning using sterilisation processes or autoclaving to reduce any infection risk.

Any of the embodiments described herein may be used in combination with a breathing apparatus, such as a nasal cannula, to locate the sampling interface on a patient. The nasal cannula may provide high flow breathing gases through the nasal cannula to the airways of the patient. The gases are generally oxygen or an air/oxygen mixture. The gases are humidified by a humidifier before delivery to the patient. The high flow gases cause turbulence and flushes the pharynx and also pushes oxygen/breathing gas into the airways of a patient. The cannula continuously provides gases to the patient's upper airways. The gas sampling interface is used to sample gases that are expired and/or exhaled by the patient. The versatile nature of the interface allows the interface to be optionally located away from the gases supply such that gas sampling measurements are not diluted as much as they would be were the gas sampling and gas delivery to occur at the same physical location in/on the patient.

The interface may be mounted to or engaged with a portion of a user's face' such as the cheek, lip or nare. Where the interface comprises a hook-like free end portion or may be manipulated to provide a hook-like portion (such as in the embodiments shown in FIGS. 1 to 6, 9 to 26, 37 to 48, 52 to 55, 70, and 71), the interface may be hooked around a portion of the patient's face, such as around the mouth or nare to engage with the patient's face and locate the interface proximate to the patient's airway.

The sampling interface may be attached to, such as clipped to, a portion of the cannula/breathing apparatus to retain the gas sampling interface in an operational position. For example, the breathing apparatus or nasal cannula may optionally be used as a mounting element for attaching the sampling interface to the breathing apparatus rather than taping the interface to a patient's face. Optionally, the interface may be attached to a breathing apparatus using any of the embodiments of attachment members shown in FIGS. 26 to 37 and 49 to 57 that suitably attaches to the breathing apparatus.

Combining the gas sampling interface with a breathing apparatus in the form of a nasal cannula reduces the need for additional headgear or tape etc. Further, attaching or clipping the gas sampling interface to a nasal cannula reduces forces on a user's cheeks or nostrils.

It will further be appreciated that any combination of the embodiments of the tip structure may also be employed in any of the embodiments described herein. For example, the gas sampling interface may comprise any of the embodiments of gas sampling lip shown in FIGS. 4 to 8, 14 to 25, 55, 58 to 66, and 68A to 71.

The nasal cannula and expired and/or exhaled gases sampling interface may be used with apnoeic patients as well as spontaneously breathing patients. Because there is no active exhalation in an apnoeic patient, there is not much $CO_2$, if any, exiting from the patient. Moreover, low flow respiratory gas delivery systems cannot set up the required turbulence model to flush the $CO_2$ from the physical dead space in the lungs of an apnoeic patient, which again means that there is not much $CO_2$ exiting from the patient. Furthermore, the small amount of $CO_2$ that exits will be diluted by the flow of gas from the breathing apparatus/gas delivery system. This dilution makes it even harder to identify whether $CO_2$ is exiting the patient's lungs or how much $CO_2$ is exiting. In the apnoeic case, $CO_2$ is usually unable to be detected in the nose or mouth because there is no patient ventilation to expel the $CO_2$ that far. The turbulent flow created in the lungs by high flow respiratory therapy has been found to flush $CO_2$ from the lungs to the nose and/or mouth to potentially allow for breath/gas sampling. Oscillating high flow therapy can amplify this response, allowing for a greater chance of being able to detect $CO_2$ in the nose or mouth. It has been found that combining cardiogenic oscillations with high flow respiratory therapy allows some amount of ventilation as the breathing gas moves with the patient's heartbeat and is expelled by cardiogenic pulses. The gas sampling interface of the present invention is particularly suitable for measuring expired and/or exhaled gas in apnoeic patients, especially when used with a respiratory gas monitor with a resolution low enough and/or with specific algorithms to cope with the very low magnitude $CO_2$ (which may be at least as low as a tenth of the normal range or lower). As a result, the gas sampling interface of the invention may be used to determine whether there is a patent airway in an apnoeic patient, whether the high flow respiratory therapy is working, and to measure the levels of $CO_2$ exhaled and/or expelled by a patient.

The foregoing description of the invention includes preferred forms thereof. Modifications may be made thereto without departing from the scope of the invention.

The term 'comprising' as used in this specification means 'consisting at least in part of'. When interpreting each statement in this specification that includes the term 'comprising', features other than that or those prefaced by the term may also be present. Related terms such as 'comprise' and 'comprises' are to be interpreted in the same manner.

Where, in the foregoing description reference has been made to integers or components having known equivalents thereof, those integers or components are herein incorporated as if individually set forth.

The disclosed methods, apparatus and systems may also be said broadly to comprise the parts, elements and features referred to or indicated in the disclosure, individually or collectively, in any or all combinations of two or more of said parts, elements or features.

Recitation of ranges herein is merely intended to serve as a shorthand method of referring individually to each separate sub-range or value falling within the range, unless otherwise indicated herein, and each separate sub-range or value is incorporated into the specification as if it were individually recited herein.

Reference to any prior art in this specification is not, and should not be taken as, an acknowledgement or any form of suggestion that that prior art forms part of the common general knowledge in the field of endeavour in any country in the world.

Certain features, aspects and advantages of some configurations of the present disclosure have been described with reference to use of the gas humidification system with a respiratory therapy system. However, certain features, aspects and advantages of the use of the gas humidification system as described may be advantageously be used with other therapeutic or non-therapeutic systems requiring the humidification of gases. Certain features, aspects and advantages of the methods and apparatus of the present disclosure may be equally applied to usage with other systems.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

The invention claimed is:

1. A respiratory therapy system for delivery of high flow respiratory therapy to a patient and sampling exhaled or expired gases from the patient, wherein the respiratory therapy system comprises:
   a breathing apparatus comprising a patient interface and a breathing gas delivery tube connected to a gas source to deliver high flow breathing gas from the gas source via the breathing gas delivery tube to the patient through the patient interface, wherein the patient interface comprises a nasal cannula comprising first and second prongs that are at least partially received within nares of the patient during use to deliver the high flow breathing gas to the patient; and
   a gas sampling interface comprising a conduit comprising a first end portion in fluid communication with a respiratory gas monitor and a second, distal end portion comprising at least one inlet for receiving exhaled or expired breathing gases from the patient, the second, distal end portion of the conduit of the gas sampling interface being configured to be selectively interchangeably positioned at or in each of a mouth and at least one of the nares of the patient while the first and second prongs are at least partially received within the nares of the patient such that the high flow breathing gas can be provided to the nares of the patient through the first and second prongs while the second, distal end portion of the conduit of the gas sampling interface is selectively repositioned.

2. The respiratory therapy system according to claim 1, wherein the breathing apparatus provides breathing gas to the patient at a flow rate of between about 15 to about 150 L/min or, if the patient is a neonatal infant patient, at a flow rate of about 2 L/min/kg.

3. The respiratory therapy system according to claim 1, wherein the conduit comprises a flexible resilient support structure that allows the second, distal end portion to be manipulated to a desired shape and to be selectively directed toward the mouth or the nare of the patient independent of the patient interface.

4. The respiratory therapy system according to claim 3, wherein the flexible resilient support structure comprises a wire located within the conduit that allows at least a portion of the conduit to be bent to form a hook-like shape.

5. The respiratory therapy system according to claim 4, wherein the wire has a smaller diameter than an internal diameter of the conduit and wherein a gap is formed between the wire and an internal wall of the conduit to allow gas to flow along the conduit.

6. The respiratory therapy system according to claim 4, wherein the conduit comprises a first, gas receiving lumen and a second, support lumen, and wherein the wire is located in at least a portion of the second, support lumen.

7. The respiratory therapy system according to claim 3, wherein the flexible resilient support structure is shape retaining such that the second, distal end portion of the conduit maintains the desired shape after manipulation.

8. The respiratory therapy system according to claim 1, further comprising an attachment member to attach the gas sampling interface to the breathing apparatus, wherein the attachment member is integral with or attached to the breathing gas delivery tube and comprises:
   a sleeve that at least partially encloses a portion of the breathing gas delivery tube;

wherein the sleeve comprises at least one clip located on an outer surface of the sleeve for receiving a portion of the conduit to attach the conduit to the breathing apparatus.

9. The respiratory therapy system according to claim 8, wherein the sleeve comprises a pair of clips that are offset from each other.

10. The respiratory therapy system according to claim 8, wherein each of the at least one clip comprises a hook comprising a tube receiving region within which a portion of the conduit may be located to follow a tortuous path.

11. The respiratory therapy system of claim 10, wherein the hook of each of the at least one clip faces in opposite directions to the hook of an adjacent one of the at least one clip.

12. The respiratory therapy system according to claim 1, wherein the gas sampling interface further comprises a tip located at the second, distal end portion of the conduit, wherein the tip comprises a substantially hollow body comprising at least one gas receiving aperture to receive gases exhaled or expired by a patient, wherein the at least one gas receiving aperture is in fluid communication with the at least one inlet of the conduit, and wherein the substantially hollow body of the tip further comprises a distal end portion comprising a distal end surface and an outer side surface.

13. The respiratory therapy system of claim 12, wherein the at least one gas receiving aperture is formed both in the distal end surface and an outer circumferential side surface such that the at least one gas receiving aperture extends from the distal end surface and along the outer side surface.

14. The respiratory therapy system according to claim 12, wherein the tip comprises at least three gas receiving apertures evenly spaced around the distal end portion of the substantially hollow body of the tip.

15. The respiratory therapy system according to claim 14, wherein each portion of the substantially hollow body located between the at least one gas receiving aperture forms a flute, wherein a plurality of flutes are substantially evenly spaced around a circumference of the distal end portion of the tip.

16. The respiratory therapy system according to claim 1, wherein the patient receiving therapy from the breathing apparatus is apnoeic.

17. The respiratory therapy system according to claim 1, wherein the breathing apparatus comprises a manifold that receives the high flow breathing gas laterally from a side and directs the high flow breathing gas to airways of the patient, wherein the gas sampling interface is removably attachable to the manifold.

18. The respiratory therapy system according to claim 17, wherein the gas sampling interface is removably attachable to a rigid portion of the manifold.

19. The respiratory therapy system according to claim 1, wherein a manifold section is insertable into the nasal cannula, and wherein the gas sampling interface is removably attachable to the manifold section.

20. A respiratory therapy system for delivery of high flow respiratory therapy to a patient and sampling exhaled or expired gases from the patient, wherein the respiratory therapy system comprises:
a breathing apparatus comprising a patient interface and a breathing gas delivery tube connected to a gas source to deliver high flow breathing gas from the gas source via the breathing gas delivery tube to the patient through the patient interface;
a gas sampling interface comprising a conduit comprising a first end portion in fluid communication with a respiratory gas monitor and a second, distal end portion comprising at least one inlet for receiving exhaled or expired breathing gases from the patient, and the second, distal end portion of the conduit of the gas sampling interface being configured to be selectively moveably positionable above and below the patient interface while the high flow breathing gas is provided to the patient; and
an attachment member to attach the gas sampling interface to the breathing apparatus, wherein the attachment member is integral with or attached to the breathing gas delivery tube and comprises a sleeve that at least partially encloses a portion of the breathing gas delivery tube.

21. The respiratory therapy system according to claim 20, wherein the breathing apparatus provides breathing gas to the patient at a flow rate of between about 15 to about 150 L/min or, if the patient is a neonatal infant patient, at a flow rate of about 2 L/min/kg.

22. The respiratory therapy system according to claim 20 further comprising a flexible resilient support structure that comprises a wire located within the conduit that allows at least a portion of the conduit to be bent to form a hook-like shape.

23. The respiratory therapy system according to claim 20, wherein the sleeve comprises at least one clip located on an outer surface of the sleeve for receiving a portion of the conduit to attach the conduit to the breathing apparatus.

24. The respiratory therapy system according to claim 23, wherein the sleeve comprises a pair of clips that are offset from each other.

25. The respiratory therapy system according to claim 23, wherein each of the at least one clip comprises a hook comprising a tube receiving region within which a portion of the conduit may be located to follow a tortuous path.

26. The respiratory therapy system of claim 25, wherein the hook of each of the at least one clip faces in an opposite direction to the hook of an adjacent one of the at least one clip.

27. The respiratory therapy system according to claim 20, wherein the breathing apparatus is a nasal cannula.

28. The respiratory therapy system according to claim 20, wherein the breathing apparatus comprises a manifold that receives the high flow breathing gas laterally from a side and directs the high flow breathing gas to an airway of the patient, wherein the gas sampling interface is removably attachable to the manifold.

29. The respiratory therapy system according to claim 28, wherein the gas sampling interface is removably attachable to a rigid portion of the manifold.

30. The respiratory therapy system according to claim 20, wherein the breathing apparatus comprises a nasal cannula and a manifold section, wherein the manifold section is insertable into the nasal cannula, and wherein the gas sampling interface is removably attachable to the manifold section.

31. A respiratory therapy system for delivery of high flow respiratory therapy to a patient and sampling exhaled or expired gases from the patient, wherein the respiratory therapy system comprises a breathing apparatus comprising a patient interface and a breathing gas delivery tube connected to a gas source to deliver high flow breathing gas from the gas source via the breathing gas delivery tube to the patient through the patient interface, a gas sampling interface comprising a conduit comprising a first end portion in fluid communication with a respiratory gas monitor and a second, distal end portion comprising at least one inlet for receiving exhaled or expired breathing gases from the patient, the conduit comprising a flexible resilient support structure that allows the second, distal end portion to be manipulated to a desired shape and to be selectively directed toward a nose or a mouth of the patient, the flexible resilient support structure comprising a wire located within the conduit that allows at least a portion of the conduit to be bent to form a hook-like shape, the wire having a smaller diameter than an internal diameter of the conduit, and a gap being formed between the wire and an internal wall of the conduit to allow gas to flow along the conduit.

* * * * *